(12) United States Patent
Williams et al.

(10) Patent No.: US 8,664,218 B2
(45) Date of Patent: *Mar. 4, 2014

(54) PHARMACEUTICAL COMPOUNDS

(71) Applicant: Astex Therapeutics Limited, Cambridge (GB)

(72) Inventors: Brian John Williams, Cambridge (GB); Martyn Frederickson, Cambridge (GB)

(73) Assignee: Astex Therapeutics Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/753,904

(22) Filed: Jan. 30, 2013

(65) Prior Publication Data

US 2013/0210820 A1    Aug. 15, 2013

Related U.S. Application Data

(63) Continuation of application No. 12/902,658, filed on Oct. 12, 2010, now Pat. No. 8,383,619, which is a continuation-in-part of application No. PCT/GB2009/050358, filed on Apr. 9, 2009.

(60) Provisional application No. 61/044,256, filed on Apr. 11, 2008.

(30) Foreign Application Priority Data

Apr. 11, 2008  (GB) .................................. 0806527.8

(51) Int. Cl.
  *A61K 31/5377* (2006.01)
  *C07D 209/44* (2006.01)

(52) U.S. Cl.
  USPC ............... 514/232.5; 514/235.2; 514/254.08; 544/107; 544/121; 544/373

(58) Field of Classification Search
  None
  See application file for complete search history.

(56) References Cited

U.S. PATENT DOCUMENTS

| | | | |
|---|---|---|---|
| 4,582,909 A | 4/1986 | Butler et al. | |
| 4,760,064 A | 7/1988 | Tominaga et al. | |
| 5,310,951 A | 5/1994 | Djuric et al. | |
| 5,332,735 A | 7/1994 | Rault et al. | |
| 6,469,024 B2 | 10/2002 | Li et al. | |
| 6,649,606 B1 | 11/2003 | Hermsmeier et al. | |
| 7,208,630 B2 | 4/2007 | Blagg et al. | |
| 7,229,986 B2 | 6/2007 | Ishihara et al. | |
| 7,385,059 B2 | 6/2008 | Berdini et al. | |
| 7,425,633 B2 | 9/2008 | Jiaang | |
| 7,577,114 B2 | 8/2009 | Hsieh | |
| 7,700,625 B2 | 4/2010 | Chessari et al. | |
| 7,754,725 B2 | 7/2010 | Chessari et al. | |
| 8,101,648 B2 | 1/2012 | Chessari | |
| 8,106,057 B2 | 1/2012 | Chessari et al. | |
| 8,277,807 B2 | 10/2012 | Gallagher | |
| 2003/0158177 A1 | 8/2003 | Ishihara et al. | |
| 2003/0203898 A1 | 10/2003 | Haning et al. | |
| 2004/0039038 A1 | 2/2004 | Bernardon et al. | |
| 2004/0253228 A1 | 12/2004 | Srivastava et al. | |
| 2004/0259877 A1 | 12/2004 | Muto et al. | |
| 2005/0037922 A1 | 2/2005 | Bickers et al. | |
| 2006/0019958 A1 | 1/2006 | Muto et al. | |
| 2006/0019961 A1 | 1/2006 | Mahaney | |
| 2006/0084647 A1 | 4/2006 | Wang et al. | |
| 2006/0089495 A1 | 4/2006 | Blagg et al. | |
| 2006/0100257 A1 | 5/2006 | Muto et al. | |
| 2006/0111409 A1 | 5/2006 | Muto et al. | |
| 2006/0122243 A1 | 6/2006 | Muto et al. | |
| 2006/0173188 A1 | 8/2006 | Seki et al. | |
| 2006/0178381 A1 | 8/2006 | Jolidon et al. | |
| 2006/0183902 A1 | 8/2006 | Baxter et al. | |
| 2007/0042997 A1 | 2/2007 | Ital et al. | |

(Continued)

FOREIGN PATENT DOCUMENTS

DE       19955283        5/2001
DE    10 2004 049 078    4/2006

(Continued)

OTHER PUBLICATIONS

Golub et al. Science (1999), vol. 286, pp. 531-536.*
Huff, Joel R. HIV Protease: A novel chemotherapeutic target for AIDS. Journal of Medicinal Chemistry, 34(8) (1991), 2305-2314.*
Lala et al. Cancer and Metastasis Reviews (1998), 17(1), 91-106.*
Brown, Michael E. "Chapter 5: Thermoptometry", *Introduction to Thermal Analysis: Techniques and Applications, Second Edition*, Netherlands, 2001.
Bryn et al., Solid State Chemistry of Drugs, 2nd edition, 1999, pp. 233-247.
Chemical Abstracts, Accession No. 81:120448 (Abstract of JP 49010506, Mar. 11, 1994).
Y. Otani et al., "An Evaluation of Amide Group Planarity in 7-azabicyclo[2.2.1]Heptane Amids. Low Amide Bond Barrier in Solution." *J. Amer. Chem. Soc.*, 125(49), 15191-15199, 1983.
Stephen M. Berg, et al., Pharmaceutical Salts, Pharmaceutical Sciences (1977) vol. 66, No. 1, p. 1-19.

(Continued)

Primary Examiner — Alicia L Otton
(74) *Attorney, Agent, or Firm* — Vedder Price P.C.; Thomas J. Kowalski; Samuel H. Megerditchian

(57) ABSTRACT

The invention provides a compound of the formula (1):

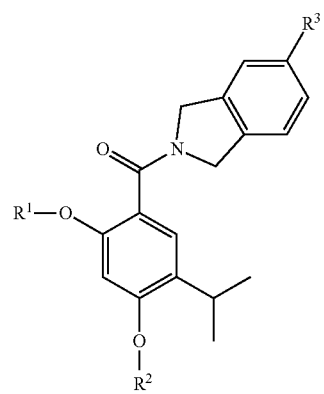

or a salt, solvate, N-oxide or tautomer thereof.

12 Claims, No Drawings

(56) References Cited

U.S. PATENT DOCUMENTS

| | | |
|---|---|---|
| 2007/0184516 A1 | 8/2007 | Marahiel et al. |
| 2007/0185059 A1 | 8/2007 | Muto et al. |
| 2007/0259871 A1 | 11/2007 | Chessari et al. |
| 2007/0265268 A1 | 11/2007 | Kitamura et al. |
| 2008/0090880 A1 | 4/2008 | Eggenweiler et al. |
| 2008/0306054 A1 | 12/2008 | Chessari |
| 2009/0215742 A1 | 8/2009 | Funk et al. |
| 2009/0215772 A1 | 8/2009 | Chessari et al. |
| 2009/0298818 A1 | 12/2009 | Lyons |
| 2010/0092474 A1 | 4/2010 | Gallagher |
| 2010/0152184 A1* | 6/2010 | Congreve et al. ......... 514/235.2 |
| 2010/0179145 A1 | 7/2010 | Gallagher et al. |
| 2011/0046155 A1 | 2/2011 | Frederickson |
| 2011/0105501 A1 | 5/2011 | Gallagher et al. |
| 2012/0251545 A1 | 10/2012 | Chessari |

FOREIGN PATENT DOCUMENTS

| | | |
|---|---|---|
| EP | 347168 | 12/1989 |
| EP | 353753 | 2/1990 |
| EP | 0474403 | 3/1992 |
| EP | 0486386 | 5/1992 |
| EP | 0500336 | 8/1992 |
| EP | 0722723 | 7/1996 |
| EP | 1283199 | 2/2003 |
| EP | 1352650 | 10/2003 |
| EP | 1510207 | 3/2005 |
| EP | 1510210 | 3/2005 |
| EP | 1512396 | 3/2005 |
| EP | 1514544 | 3/2005 |
| EP | 1642880 | 4/2006 |
| EP | 1704856 | 9/2006 |
| EP | 1852112 | 11/2007 |
| JP | 49010506 | 1/1974 |
| JP | 09194450 | 7/1997 |
| WO | WO 91/08205 | 6/1991 |
| WO | WO 92/17467 | 10/1992 |
| WO | WO 97/26884 | 7/1997 |
| WO | WO 97/35999 | 10/1997 |
| WO | WO 97/36876 | 10/1997 |
| WO | WO 97/39750 | 10/1997 |
| WO | WO 97/47270 | 12/1997 |
| WO | WO 98/40385 | 9/1998 |
| WO | WO 98/45255 | 10/1998 |
| WO | WO 98/47885 | 10/1998 |
| WO | WO 98/50036 | 11/1998 |
| WO | WO 99/21422 | 5/1999 |
| WO | WO 99/29705 | 6/1999 |
| WO | WO 00/59867 | 10/2000 |
| WO | WO 01/36351 | 5/2001 |
| WO | WO 01/60369 | 8/2001 |
| WO | WO 01/87834 | 11/2001 |
| WO | WO 01/87887 | 11/2001 |
| WO | WO 01/90053 | 11/2001 |
| WO | WO 02/12210 | 2/2002 |
| WO | WO 02/18319 | 3/2002 |
| WO | WO 03/051877 | 6/2003 |
| WO | WO 03/053366 | 7/2003 |
| WO | WO 03/055860 | 7/2003 |
| WO | WO 03/086282 | 10/2003 |
| WO | WO 03/103665 | 12/2003 |
| WO | WO 2004/005295 | 1/2004 |
| WO | WO 2004/007501 | 1/2004 |
| WO | WO 2004/035571 | 4/2004 |
| WO | WO 2004/072051 | 8/2004 |
| WO | WO 2004/074283 | 9/2004 |
| WO | WO 2004/096757 | 11/2004 |
| WO | WO 2005/000300 | 1/2005 |
| WO | WO 2005/000839 | 1/2005 |
| WO | WO 2005/007151 | 1/2005 |
| WO | WO 2005/009940 | 2/2005 |
| WO | WO 2005/012256 | 2/2005 |
| WO | WO 2005/012297 | 2/2005 |
| WO | WO 2005/012541 | 2/2005 |
| WO | WO 2005/016889 | 2/2005 |
| WO | WO 2005/023818 | 3/2005 |
| WO | WO 2005/037214 | 4/2005 |
| WO | WO 2005/047249 | 5/2005 |
| WO | WO 2005/000778 | 6/2005 |
| WO | WO 2005/063222 | 7/2005 |
| WO | WO 2006/015123 | 2/2006 |
| WO | WO 2006/023778 | 3/2006 |
| WO | WO 2006/047740 | 5/2006 |
| WO | WO 2006/051808 | 5/2006 |
| WO | WO 2006/055760 | 5/2006 |
| WO | WO 2006/070195 | 7/2006 |
| WO | WO 2006/077426 | 7/2006 |
| WO | WO 2006/082001 | 8/2006 |
| WO | WO 2006/088193 | 8/2006 |
| WO | WO 2006/109085 | * 10/2006 ........... C07D 209/44 |
| WO | WO 2006/117669 | 11/2006 |
| WO | WO 2006/125119 | 11/2006 |
| WO | WO 2007/050124 | 5/2007 |
| WO | WO 2008/044027 | * 4/2008 ........... C07D 209/08 |
| WO | WO 2008/044029 | 4/2008 |
| WO | WO 2008/044034 | 4/2008 |
| WO | WO 2008/044041 | 4/2008 |
| WO | WO 2008/044045 | 4/2008 |
| WO | WO 2008/044054 | 4/2008 |
| WO | WO 2008/053319 | 5/2008 |

OTHER PUBLICATIONS

Mahaney et al., Synthesis and Activity of a New Class of Pathway-Selective Estrogen Receptor Ligands: Hydroxybenzoyl-3,4-dihydroquinoxalin-2(1H)-ones. Bioorg Med Chem. May 15, 2006;14(10):3455-66.

Madsen et al., Glucose-6-Phosphatase Catalytic Enzyme Inhibitors: Synthesis and in Vitro Evaluation of Novel 4,5,6,7-tetrahydrothieno[3,2-c]-and -[2,3c]pyridines. Bioorg Med Chem. Sep. 2000;8(9):2277-89.

Vippagunta et al., Adv. Drug Delivery Reviews (2001) vol. 48, p. 3-26.

Dymock, et al., Expert Opin. Ther. Patents (2004) vol. 14, p. 837-847.

Bohonowych et al., Journal of Oncology, vol. 2010, pp. 1-17 (2010).

Stephen Neidle Ed,. Cancer Drug Design and Discovery, Elsevier/Academic Press, 2008, pp. 427-431.

Gura, Science, Nov. 7, 1997, vol. 278, No. 5340, pp. 1041-1042.

Roberts et al, JAMA, 292(17): 2130-2140 (2004).

Ju huai-qiang et al: "Synthesis and in vitro anti-HSV-1 activity of a novel Hsp90 inhibitor BJ-B11.", Bioorganic & Medicinal Chemistry Letters Mar. 15, 2011, vol. 21, No. 6, p. 1675-1677.

Hunter, et al., Cdc37: A Protein Kinase Chaperone? Trends in Cell Biology (1997) vol. 7, Issue 4, p. 157-161.

Connor, et al., Antiviral Activity and RNA Polymerase Degradation Following Hsp90 Inhibition in a Range of Negative Strand Viruses, Virology (2007) vol. 362, p. 109-119.

Ernst Mutschler, et al., Drug Actions: Basic Principles and Therapeutic Aspects, CRC Press 1995, p. 515-580.

Shin-ichiro Nakagawa, et al., Hsp90 Inhibitors Suppress HCV Replication in Replicon Cells and Humanized Liver Mice, Biochemical and Biophysical Research Communications (2007) vol. 353, p. 882-888.

Lloyd Waxman, et al., Host Cell Factor Requirement for Hepatitis C Virus Enzyme Maturation, PNAS (2001) vol. 98, No. 24, p. 13931-13935.

Galam, et al. Bioog. Med. Chem. (2007) vol. 15, p. 1939-1946.

Wermuth, The Practice of Medicinal Chemistry, 2d ed. (2003) 768 pages, Chapters 9-10 provided.

* cited by examiner

PHARMACEUTICAL COMPOUNDS

INCORPORATION BY REFERENCE

This application is a continuation of U.S. application Ser. No. 12/902,658, filed Oct. 12, 2010, now U.S. Pat. No. 8,383,619, which in turn is a continuation-in-part application of international patent application Serial No. PCT/GB2009/050358, filed Apr. 9, 2009, which claims benefit of U.S. Provisional Application Ser. No. 61/044,256, filed Apr. 11, 2008, and United Kingdom Patent Application No. 0806527.8, filed Apr. 11, 2008, the contents of all of which are incorporated herein by reference in their entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

TECHNICAL FIELD

This invention relates to pro-drugs of compounds that inhibit or modulate the activity of the heat shock protein 90 (Hsp90), to the use of the pro-drugs in the treatment or prophylaxis of disease states or conditions mediated by Hsp90, and to novel pro-drugs that break down in vivo to give compounds having Hsp90 inhibitory or modulating activity. Also provided are pharmaceutical compositions containing the pro-drugs.

BACKGROUND OF THE INVENTION

In response to cellular stresses including, but not limited to heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major inducible form Hsp90α and minor constitutively expressed form Hsp90β and two other closely related chaperones which are restricted in their intracellular location (Endoplasmic reticulum GP96/GRP94; mitochondrial TRAP1). The term HSP90 as used here includes all these analogues unless stated. Hsp90 binds proteins at a late stage of folding and is distinguished from other Hsps in that most of its protein substrates are involved in signal transduction. Hsp90 has a distinct ATP binding site, including a Bergerat fold characteristic of bacterial gyrase, topoisomerases and histidine kinases. It has been shown that ATP bound at the N-terminal pocket of Hsp90 is hydrolysed. This ATPase activity results in a conformational change in Hsp90 that is required to enable conformational changes in the client protein.

A dimerization domain and a second ATP binding site, which may regulate ATPase activity, is found near the c-terminus of Hsp90. Dimerization of HSP90 appears critical for ATP hydrolysis. Activation of Hsp90 is further regulated through interactions with a variety of other chaperone proteins and can be isolated in complex with other chaperones including, but not limited to Hsp70, Hip, Hop, p23, and p50cdc37. Many other co-chaperone proteins have also been demonstrated to bind HSP90. A simplified model has emerged in which ATP binding to the amino terminal pocket alters Hsp90 conformation to allow association with a multichaperone complex. First the client protein is bound to an Hsp70/Hsp40 complex. This complex then associates with Hsp90 via Hop. When ADP is replaced by ATP, the conformation of Hsp90 is altered, Hop and Hsp70 are released and a different set of co-chaperones is recruited including p50cdc37 and p23. ATP hydrolysis results in the release of these co-chaperones and the client protein from the mature complex. Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et. al., 1997. J Biol. Chem., 272:23834-23850).

Despite Hsp90 being ubiquitously expressed, GA has a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec J. Med. Chem. 2004, 47, 3865-3873). Furthermore the ATP-ase activity of Hsp90 is elevated in cancer cells and is an indication of the increased level of stress in these cells. Hsp90 gene amplification has also been reported to occur in the later stages of cancer (Jolly and Morimoto JNCI Vol. 92, No. 19, 1564-1572, 2000).

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

There is some evidence that Hsp90 is found primarily within "activated" multichaperone complexes in the tumour cells as opposed to "latent" complexes in normal cells. One component of the multichaperone complex is the cdc37 co-chaperone. Cdc37 binds Hsp90 at the base of the ATP binding site and could affect the off rates of inhibitors bound to Hsp90 in the "activated" state (Roe et. al., Cell 116, (2004), pp. 87-98). The client protein bound to the Hsp90-Hsp70 form of the chaperone complex is believed to be more susceptible to ubiquitination and targeting to the proteasome for degradation. E3 ubiquitin ligases have been identified with chaperone interacting motifs and one of these (CHIP) was shown to promote the ubiquitination and degradation of Hsp90 client proteins (Connell et al., 2001. Xu et al., 2002).

Hsp90 Client Proteins

The number of reported Hsp90 client proteins now exceeds 100. Since many of its client proteins are involved in cell signalling proliferation and survival, Hsp90 has received major interest as an oncology target. Two groups of client proteins, cell signalling protein kinases and transcription factors, in particular suggest Hsp90 regulation may have potential benefit as an anticancer therapy.

Hsp90 protein kinase client proteins implicated in cell proliferation and survival include the following:

c-Src

Cellular Src (c-Src) is a receptor tyrosine kinase, required for mitogenesis initiated by multiple growth factor receptors, including, but not limited to the receptors for epidermal growth factor receptor (EGFR), platelet-derived growth factor receptor (PDGFR), colony stimulating factor-1 (CSF-1R), and the basic fibroblast growth factor (bFGFR). C-Src is also overexpressed and activated in many of the same human carcinomas that overexpress EGFR and ErbB2. Src is also required for the maintenance of normal bone homeostasis through its regulation of osteoclast function.

p185erbB2

ErbB2 (Her2/neu) is a receptor tyrosine kinase overexpressed in a variety of malignancies including, but not limited to breast, ovarian, prostate, and gastric cancers. ErbB2 was originally identified as an oncogene and inhibition of Hsp90 results in the polyubiquitination and degradation of erbB2.

Polo Mitotic Kinase

Polo-like kinases (Plks) are important regulators of cell cycle progression during M-phase. Plks are involved in the assembly of the mitotic spindle apparatus and in the activation of CDK/cyclin complexes. Plk1 regulates tyrosine dephosphorylation of CDKs through phosphorylation and activation of Cdc25C. CDK1 activation in turn leads to spindle formation and entry into M phase.

Akt (PKB)

Akt is involved in pathways that regulate cell growth by stimulating cell proliferation and suppressing apoptosis. Hsp90 inhibition by ansamycins results in a reduction in the Akt half life through ubiquitination and proteasomal degradation. Binding of cdc37 to Hsp90 is also required for the down-regulation of Akt. Following ansamycin treatment cancer cells arrest in the G2/M phase of the cell cycle 24 hours after treatment and proceed to apoptosis 24-48 hours later. Normal cells also arrest 24 hours after ansamycin treatment, but do not proceed on to apoptosis.

c-Raf, B-RAF, Mek

The RAS-RAF-MEK-ERK-MAP kinase pathway mediates cellular responses to growth signals. RAS is mutated to an oncogenic form in approximately 15% of human cancers. The three RAF genes are serine/threonine kinases that are regulated by binding RAS.

EGFR

The epidermal growth factor receptor (EGFR) is implicated in cell growth, differentiation, proliferation, survival, apoptosis, and migration. Overexpression of EGFR has been found in many different cancers and activating mutations of its kinase domain appear to be pathogenic in a subset of adenocarcinoams of the lung.

Flt3

FMS-like tyrosine kinase 3 (FLT3) is a receptor tyrosine kinase involved in cell proliferation, differentiation and apoptosis. Flt3 activation also leads to the activation of phosphatidylinositol 3-kinase (PI3K) and RAS signal-transduction cascades.

c-Met c-met is a receptor tyrosine kinase which binds hepatocyte growth factor (HGF) and regulates both cell motility and cell growth. c-met is overexpressed in tumours, including, but not limited to thyroid, stomach, pancreatic and colon cancer. HGF is also detected around the tumours, including liver metastases. This suggests that c-met and HGF play an important role in invasion and metastasis.

Cdk1, Cdk2, Cdk4, Cdk6

Cdk1, Cdk2, Cdk4, and Cdk6 drive the cell cycle. The activity of CDKs is regulated by their binding to specific subunits such as cyclins, inhibitory and assembly factors. The substrate specificity and timing of CDK activities is dictated by their interaction with specific cyclins. Cdk4/cyclin D and Cdk6/cyclin D are active in the G1 phase, Cdk2/cyclin E and Cdk2/cyclin A in S phase, and Cdc2/cyclin A and Cdc2/cyclin B in G2/M phase.

Cyclin-dependent kinase type 4 (CDK4), plays a key role in allowing cells to traverse G1 to S-phase transition of the cell cycle and is constitutively activated in many human cancers. The CDK4 activator, cyclin D1, is overexpressed and a CDK4 inhibitor, p16, is deleted in a variety of human tumours.

Cdk1/Cdk2 inhibitors have been developed which reversibly block normal cells in either the G1/S-phase or at the G2/M border. G2/M arrest is generally less well tolerated by the cells and consequently, they undergo apoptotic cell death. Since Hsp90 also is known to affect cell survival pathways this effect may be further amplified with an Hsp90 inhibitor.

Wee-1

The Wee-1 protein kinase carries out the inhibitory phosphorylation of CDC2 on tyrosine 15 (Tyr15). This is required for activation of the G2-phase checkpoint in response to DNA damage.

Hsp90 transcription factors implicated in cell proliferation and survival include the following:

Mutant p53

P53 is a tumour suppressor protein that causes cell cycle arrest and induces apoptosis. P53 is mutated in approximately half of all cancers. Mutant p53 associates with Hsp90 and is down-regulated in cancer lines treated with Hsp90 inhibitors, while wild type p53 levels were unaffected.

Estrogen Receptor/Androgen Receptor

Approximately 70% of post-menopausal women who develop breast cancer have tumours that express the estrogen receptor. The first line treatment of these patients is directed at preventing signalling through this pathway and thus inhibiting tumour growth. This can be done by ovarian ablation, treatment with gonadotrophin releasing hormone agonists, aromatase inhibition or treatment with specific agonists which bind to the estrogen receptor but prevent further signalling. Ultimately patients develop resistance to these interventions often as a consequence of crosstalk between the estrogen receptor and growth factor receptors located on the cell membrane. In the unliganded state estrogen receptors are complexed with Hsp90 which facilitates hormone binding. Following binding to the mature receptor Hsp90 complex the liganded receptor can bind to hormone-response elements (HREs) within the regulatory regions of target genes involved in maintaining cell proliferation Inhibition of Hsp90 initiates proteosomal degradation of the estrogen receptor thus preventing further growth signalling via this pathway. Prostate cancers are hormone-dependent malignancies that respond to therapeutic interventions which reduce circulating levels of testosterone or prevent testosterone binding to the androgen receptor. Although patients initially respond to these treatments most subsequently develop resistance via restoration of signalling via the androgen receptor. Prior to ligand binding the androgen receptor exists in a complex with Hsp90 and other co-chaperones including p23 and immunophilins. This interaction maintains the androgen receptor in a high-affinity ligand binding conformation Inhibition of Hsp90 leads to proteosomal degradation of the androgen receptor and other co-chaperones which may sensitise the tumour to further hormonal therapies.

Mutated steroid hormone receptors that have arisen for example during anti-hormone therapy and which might be resistant to such therapies are likely to have a greater dependence on HSP90 for their stability and hormone binding function.

Hif-1a

Hypoxia inducible factor-1a (HIF-1a) is a transcription factor that controls the expression of genes which play a role in angiogenesis. HIF-1a is expressed in the majority of metastases and is known to associate with Hsp90. Ansamycin treatment of renal carcinoma cell lines leads to the ubiquitination and proteasomal degradation of HIF-1a.

Hsp90 inhibitors are capable of affecting a large number of targets significant to signal transduction in tumour cell proliferation. Signal transduction inhibitors which regulate the activities of a single target, may not be as efficacious due to signalling pathway redundancy and the rapid development of resistance.

By regulating multiple targets involved in cell signalling and cell proliferation HSP90 inhibitors may prove beneficial in the treatment of a wide spectrum of proliferative disorders.

ZAP70

ZAP-70, a member of the Syk-ZAP-70 protein tyrosine kinase family, is normally expressed in T cells and natural killer cells and has a critical role in the initiation of T-cell signaling. However, it is also expressed aberrantly in approximately 50% of cases of CLL, usually in those cases with unmutated B-cell receptor genes. The mutational status of immunoglobulin heavy-chain variable-region ($IgV_H$) genes in the leukemic cells of chronic lymphocytic leukemia (CLL) is an important prognostic factor. The expression of ZAP-70 in CLL cells correlates with $IgV_H$ mutational status, disease progression, and survival. ZAP-70 positive CLL is more aggressive than ZAP-70 negative CLL indicating that ZAP-70 may be a key driver of malignancy in this disease. ZAP-70 is physically associated with HSP90 in B-CLL lymphoblasts thus the inhibition of Hsp90 may sensitise these cells to existing chemotherapy or monoclonal antibody therapy.

HSP90 Inhibitors as Anti-fungal, Anti-protozoal and Anti-parasitic Agents

Fungal infections have become a major cause for concern in recent years because of the widespread use of immunosuppressive therapies and the increasing incidence of species that are resistant to established antifungal agents such as the azoles. The growing population of immunocompromised patients (e.g. patients such as organ transplant patients, cancer patients undergoing chemotherapy, burn patients, AIDS patients, or patients with diabetic ketoacidosis) has given rise to an increase in the incidence of opportunistic fungal infections by fungal agents such as *Candida*, *Cryptoccocus* and *Aspergillus* species and, on occasion, *Fusarium*, *Trichosporon* and *Dreschlera* species. Consequently, there is a need for new anti-fungal agents that can be used to treat the growing numbers of patients with fungal infections and in particular infections due to fungi that have become resistant to existing antifungal drugs.

HSP90 is conserved across evolution being found in bacteria (e.g. HTPG in *E. coli*) and yeast (e.g. HSC82 and HSP82). Although clients have not been formally identified for the *E. coli* form, in yeast and all higher organisms the HSP90 family has been shown to function as a chaperone for many essential proteins as described above.

Infection by a range of pathogens is associated with an antibody response to HSP90. For example in *Candida albicans* infected patients the 47kDa C-terminal fragment of HSP90 is an immunodominant epitope. Furthermore this antibody response is associated with good prognosis suggesting a protective effect against infection. Recombinant antibodies to an epitope in this polypeptide are also protective against infection in mouse models of invasive candidiasis. (See Mathews et al *Antimicrobial Agents and Chemotherapy* 2003 vol 47, 2208-2216 and references therein). Likewise surface expressed HSP90 serves as an antigen in Chagas' disease, ascariasis, leishmaniasis, toxoplamosis and infection due to *Schistosoma mansoni* and it has been postulated that antibodies to HSP90 convey protection against plamodium infection and Malaria.

Mycograb (NeuTec Pharma/Novartis) is a human recombinant monoclonal antibody against heat shock protein 90 that is being developed as a treatment for candida and has shown significant responses in early trials. Furthermore, the natural product HSP90 inhibitors Geldanamycin, Herbimycin and Radicicol were originally identified by their anti-fungal activity. Key essential proteins have been identified as HSP90 clients in several human pathogens (see Cowen and Lindquist, Science. 2005 Sep. 30; 309(5744):2175-6.) Thus HSP90 can play an important role in the growth of pathogens such as *Candida* species, and HSP90 inhibitors can be useful as treatments for a range of infectious diseases including candidiasis.

It has also been found that Hsp90 increases the capacity of fungi to develop antifungal drug resistance (see Cowen L E, Lindquist S. "Hsp90 potentiates the rapid evolution of new traits: drug resistance in diverse fungi". *Science*. 2005 Sep. 30; 309 (5744):2185-9). Therefore, co-administration of an Hsp90 inhibitor with an antifungal drug may enhance the efficacy of the antifungal drug and reduce resistance by preventing the emergence of resistant phenotypes.

HSP90 Inhibitors in the Treatment of Pain, Neuropathic Conditions and Stroke

Cdk5 is a member of the Cdk family of serine/threonine kinases, most of which are key regulators of the cell cycle. Cdk5 activity is regulated through association with its neuron-specific activators, p35 and p39. Recent evidence suggests that CDK5 can phosphorylate tau protein and a number of other neuronal proteins such as NUDE-1, synapsinl, DARPP32 and the Munc18/Syntaxin1A complex. The evidence also suggests that aberrant Cdk5 activity induced by the conversion of p35 to p25 plays a role in the pathogenesis of neurodegenerative diseases such as Alzheimer's disease (AD), amyotrophic lateral sclerosis (ALS) and Niemann's Pick type-C disease (NPD). Abnormal hyperphosphorylation of tau after $A\beta_{1-42}$ treatment destabilizes microtubules, contributing to neurite degeneration and the formation of paired helical filaments (PHFs) containing neurofibrillary tangles (NFTs), one of the principal lesions of AD. It has further been found that cdk5 is necessary for correct neuronal development The p35 protein which acts as a regulator of CDK5 activity has recently been identified as a client protein for HSP90 and therefore the activity of CDK5 can be regulated by changes in the level and activity of HSP90. Thus inhibition of HSP90 can lead to loss of p35, an inhibition of CDK5, a reduction of phosphorylated tau protein in susceptible individuals and may bring benefit to sufferers of Alzheimers Disease.

Additionally inhibition of HSP90 using known agents has been shown to reduce the accumulation of tau protein aggregates in cellular systems in vitro. (Dickey et al Curr Alzheimer Res. 2005 April; 2(2):231-8).

Cdk5 has also been shown to have a role in mediating pain signalling. Both Cdk5 and p35 have been shown to be expressed in nociceptive neurons. In p35 knockout mice, which show substantially reduced Cdk5 activity, the response to painful thermal stimuli is delayed (Pareek, T. K., et al., Proceedings of the National Academy of Sciences., 103:791-796 (2006). Additionally administration of the cyclin-dependent kinase 5 (Cdk5) inhibitor roscovitine has been shown to attenuate formalin-induced nociceptive responses in rats (Wang, Cheng-haung, et al., Acta Pharmacologica Sinica., 26:46-50 (2005). Activation of calpain is calcium dependent and is known to affected by activation of the NMDA receptor calcium channel (Amadoro, G; Proceedings of the National Academy of Sciences of the United States of America, 103, 2892-2897 (2006)). NMDA receptor antagonists are know to be clinically effective against neuropathic pain conditions (Christoph, T; et al., Neuropharmacology, 51, 12-17 (2006)). This efficacy may be linked to the effect of NMDA receptor related calcium influx on calpain activity and its subsequent effect on the activity of Cdk5. As such compounds modulating Cdk5 activity are expected to be useful for the treatment or prevention of pain and thus modulation of the CDK5 regulator p35 by HSP90 inhibition could lead to inhibition of CDK5.

It is desirable to have an agent for the palliative treatment of pain, i.e. the direct relief of pain in addition to the relief of pain as the result of amelioration of the underlying disease or medical condition, which is the cause of the pain.

Various Cdk's (especially Cdk's 4, 5 & 6) have been shown to be involved with or mediate neuronal death following hypoxic or ischemic insult (Rashidan, J.; et al.; Proceedings of the National Academy of Sciences., 102:14080-14085 (2005). Furthermore the Cdk inhibitor flavopiridol has been shown to significantly reduce neuronal death in a rat model of focal cerebral ischemia (Osuga, H.; et al.; Proceedings of the National Academy of Sciences., 97:10254-10259 (2000). Cdk5 inhibitors have been shown to have protective effects in both necrotic and apoptotic paradigms of neuronal cell death (Weishaupt, J.; et al.; Molecular and Cellular Neuroscience., 24:489-502 (2003). Stroke is a cerebrovascular event, which occurs when the normal bloodflow to the brain is disrupted, and the brain receives too much or too little blood. Stroke is one of the leading causes of death worldwide, and is also one of the most common causes of neurologic disability.

Ischemic stroke, which is the most common type of stroke, results from insufficient cerebral circulation of blood caused by obstruction of the inflow of arterial blood. Normally, adequate cerebral blood supply is ensured by a system of arteries within the brain. However, various disorders, including, but not limited to inflammation and atherosclerosis, can cause a thrombus, i.e., a blood clot that forms in a blood vessel. The thrombus may interrupt arterial blood flow, causing brain ischemia and consequent neurologic symptoms. Ischemic stroke may also be caused by the lodging of an embolus (an air bubble) from the heart in an intracranial vessel, causing decreased perfusion pressure or increased blood viscosity with inadequate cerebral blood flow. An embolus may be caused by various disorders, including, but not limited to atrial fibrillation and atherosclerosis.

A second type of stroke, hemorrhagic stroke, involves a hemorrhage or rupture of an artery leading to the brain. Hemorrhagic stroke results in bleeding into brain tissue, including the epidural, subdural, or subarachnoid space of the brain. A hemorrhagic stroke typically results from the rupture of an arteriosclerotic vessel that has been exposed to arterial hypertension or to thrombosis.

One opportunity for intervention in stroke is the prevention or reduction of risk of stroke in patients at risk for stroke. There are many known risk factors for stroke, including, but not limited to vascular inflammation, atherosclerosis, arterial hypertension, diabetes, hyperlipidemia and atrial fibrillation. At risk patients have been treated with agents to control blood pressure or manage blood lipid level, and have been treated with antiplatelet agents (such as clopidrogel) and anticoagulants. A second opportunity is the treatment of acute stroke. However, current pharmacologic therapies for treating acute stroke are limited to restoring blood flow within a narrow therapeutic time window of less than three hours after stroke. There remains a need for agents which are effective within a longer therapeutic time window. Another opportunity is recovery or restoration after the acute stroke period, i.e. the reduction or prevention of secondary cell damage in the penumbra. There remains a need for agents which are effective in reducing or preventing secondary cell damage after stroke.

It would be desirable to obtain a single pharmaceutical agent which can be used in more than one of the above-mentioned opportunities for treating stroke. Such an agent may be administered to patients at risk for stroke, and also may be administered to patients suffering from acute stroke, or patients undergoing treatment for recovery or restoration after the acute stroke period. Such an agent may also target more than one distinct mechanism in the biochemical cascade of stroke.

HSP90 Inhibitors and the Treatment of Hepatitis C and Other Viral Diseases

Infection of a host cell with viral RNA/DNA results in a substantial redirection of cellular protein sysnthesis towards key viral proteins encoded by the viral nucleic acid. The increased protein synthetic burden places a stress on the cell as a consequence of increased demand for energy and synthetic precursers. Upregulation of heat shock proteins is frequently a consequence of viral infection at least in part due to this stress. One function of the HSP induction may be to assist in the stabilization and folding of the high levels of 'foreign' protein generated in preparation for virus replication. In particular recent work has suggested that HSP90 is required for stable production of functional NS2/3 protease in Hepatitis C(HCV) replicon infected cells. HSP 90 inhibitors have also been demonstrated to block viral replication in in vitro systems. (Nagkagawa, S, Umehara T, Matsuda C, et al Biochem. Biophys. Res Commun. 353 (2007) 882-888; Waxman L, Witney, M et al PNAS 98 (2001) 13931-13935).

Heat Shock Proteins and antitumour drug resistance

It has long been recognized that the native tertiary conformation of any given polypeptide is determined by its primary (amino acid) sequence. However, as explained above, it is now clear that the proper folding of many proteins in vivo requires the assistance of heat-shock proteins (Hsps) acting as molecular chaperones. While this chaperone function is important to normal cellular function under all conditions, it becomes crucial in cells which are stressed (for example by heat, hypoxia or acidosis).

Such conditions typically prevail in tumour cells, which exist in a hostile host environment. The upregulation of Hsps often seen in such cells is therefore likely to represent a mechanism by which malignant cells maintain the integrity of their proteomes under conditions which compromise protein folding. Thus, modulators or inhibitors of stress proteins in general (and Hsp90 in particular) represent a class of chemotherapeutics with the unique ability to inhibit multiple aberrant signalling pathways simultaneously. They can therefore exert antitumour effects whilst eliminating (or reducing the incidence of) resistance relative to other treatment paradigms.

Moreover, therapeutic anticancer interventions of all types necessarily increase the stresses imposed on the target tumour cells. In mitigating the deleterious effects of such stresses, Hsps are directly implicated in resisting the effects of cancer drugs and treatment regimens. Thus, modulators or inhibitors of stress protein function in general (and Hsp90 in particular) represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

Pro-Drugs

Pro-drugs are generally recognised as being chemical compounds that have little or no pharmacological activity themselves but which undergo biotransformation to a therapeutically active metabolite in vivo (see for example Bernard Testa, *Biochemical Pharmacology*, 68 (2004), 2097-2106, and *"Design of Prodrugs"* (Bundgaard H. ed.) 1985 Elsevier Science Publishers B. V. (Biomedical Division) and Rautio et al., Nature Reviews (Drug Discovery), Volume 7, March 2008, 255 to 270.

Pro-drugs are used for a variety of reasons. For example, they may be used inter alia to:
  impart better solubility to an otherwise insoluble or poorly soluble drug
  improve chemical stability
  improve the organoleptic properties of a drug
  alter the pharmacokinetics of a drug
  reduce pre-systemic (first pass) metabolism
  reduce the extent of conjugation of a drug
  improve oral absorption
  provide selective targetting of a drug
  provide in situ activation of a cytotoxic agent Whereas as many as 5-7% of drugs approved worldwide can be classified as prodrugs (Rautio (2008)), the development of pro-drugs of drugs containing phenolic hydroxyl groups has proved somewhat problematic.

Various derivatives of hydroxyl groups have been proposed and/or investigated (see Rautio idem) but with varying results.

In the case of the terbutaline prodrug (bambuterol), the two phenolic hydroxy groups of terbutaline have been derivatised to give dimethylcarbamoyloxy groups which are slowly converted back to the hydroxyl groups in vivo to regenerate terbutaline.

However, elsewhere in the literature, it has been found that many simple dialkylcarbamate derivatives of hydroxyl compounds are too stable and too resistant to hydrolysis to function as pro-drugs (Igarashi et al., *Chem. Pharm. Bull.*, 55(2), 328-333 (2007)—see in particular page 329 column 2).

Simple dialkylcarbamate prodrugs have also been associated with toxic side effects (Thorberg et al., *J. Med. Chem.*, 1987, 30, No. 11, 2008-2012—see in particular page 2010. column 2). Thorberg et al found that arylcarbamate derivatives did not give rise to the same toxic effects.

Monoalkylcarbamate derivatives of phenolic hydroxyl compounds have also been investigated as potential prodrugs. Igarashi et al., (idem) found that the monoethylcarbamoyl derivative of a phenolic capillarisin analogue gave good plasma levels of the parent phenolic compound but that other monosubstituted carbamates were too readily hydrolysed or metabolised to be suitable as prodrugs. Furthermore, like dialkylcarbamates, monoalkylcarbamates have also been associated with toxic side effects (Thorberg et al., idem page 2010 column 2).

Ester and ether derivatives of the phenolic dopamine autoreceptor agonist (−)-3-(hydroxyphenyl)-N-propyl-piperidine were also investigated by Thorberg et al. as potential prodrugs but they found (see page 2010 column 1) the ether and acyl ester derivatives failed to generate the parent compound in plasma, possibly because of a lack of stability and a tendency to hydrolyse while in the digestive tract.

Thus, as indicated above, the development of prodrugs for phenolic compounds is far from straightforward and functional group derivatives that may provide useful prodrug properties in one class of compounds may be ineffective or may even give rise to toxicity problems in other classes of compounds.

WO 99/29705 (Glycomed et al) discloses a class of glycomimetic compounds having a number of possible uses including the treatment of cancer. One compound specifically disclosed in WO 99/29705 is the compound 2-(2-hydroxybenzoyl)-1,2,3,4-tetrahydro-isoquinoline-3-carboxylic acid.

WO 2006/117669 (Pfizer) discloses a class of amide resorcinols as Hsp90 inhibitors. International application WO2006/109085 (Astex Therapeutics) discloses hydroxybenzoic acid amides as Hsp90 inhibitors.

WO 2008/044027 (Astex Therapeutics) discloses prodrugs of the compounds of WO2006/109085.

Citation or identification of any document in this application is not an admission that such document is available as prior art to the present invention.

SUMMARY OF THE INVENTION

The present invention provides a novel group of pro-drug compounds containing functional groups that are modified or removed in vivo to give compounds having Hsp90 inhibiting or modulating activity. The pro-drug compounds are expected to be useful in preventing or treating disease states or conditions mediated by Hsp90.

Thus, for example, it is envisaged that the compounds of the invention are useful in alleviating or reducing the incidence of cancer.

Accordingly, in a first aspect (Aspect I), the invention provides a compound of the formula (1):

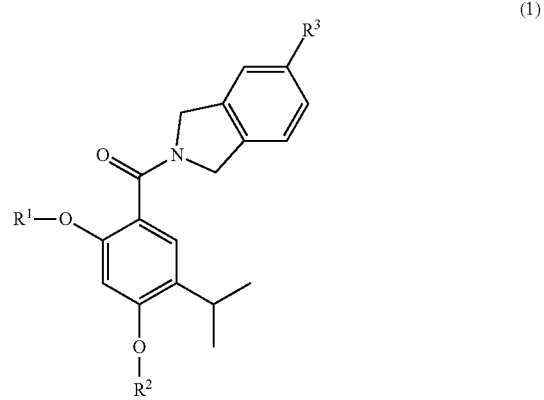

or a salt, solvate, N-oxide or tautomer thereof;
wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;
$R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;
$R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and R³ is selected from groups A to G:

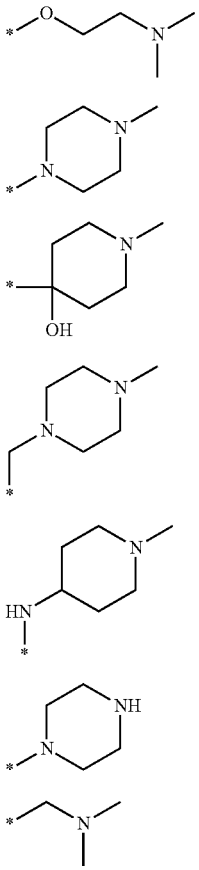

wherein the asterisk denotes the point of attachment to the isoindoline ring;
but excluding the compounds
dimethyl-carbamic acid 5-dimethylcarbamoyloxy-2-isopropyl-4-[5-(4-methyl-piperazin-1-yl)-1,3-dihydro-isoindole-2-carbonyl]-phenyl ester;
acetic acid 5-acetoxy-4-isopropyl-2-[5-(4-methyl-piperazin-1-yl)-1,3-dihydro-isoindole-2-carbonyl]-phenyl ester;
2,2-dimethyl-propionic acid 5-(2,2-dimethyl-propionyloxy)-4-isopropyl-2-[5-(4-methyl-piperazin-1-yl)-1,3-dihydro-isoindole-2-carbonyl]-phenyl ester; and
acetic acid 5-acetoxy-4-isopropyl-2-[5-(4-methyl-piperazin-1-ylmethyl)-1,3-dihydro-isoindole-2-carbonyl]-phenyl ester.

In formula (1), either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen.

In one general embodiment (Embodiment AA) $R^1$ is $R^{1a}$ and $R^2$ is $R^{2a}$.

Within Embodiment AA, in one group of compounds (Group AAA), $R^{1a}$ and $R^{2a}$ can be the same or different and each can be selected from hydrogen, $C_{1-2}$ alkyl (e.g. methyl), $C_{2-3}$ alkenyl (e.g. allyl) and $C_{2-3}$ alkynyl (e.g. propargyl) wherein the $C_{1-2}$ alkyl is optionally substituted by methoxy.

For example, in a Group AAAA of compounds within Group AAA, $R^{1a}$ and $R^{2a}$ can each be selected from hydrogen, methyl, methoxymethyl and allyl.

In one particular sub-group (AAAAA) of compounds within Group AAAA, $R^{1a}$ and $R^{2a}$ are each selected from hydrogen and methyl.

In another particular sub-group (AAAAB) of compounds within Group AAAA, $R^{1a}$ and $R^{2a}$ are each selected from hydrogen and methoxymethyl.

In a further particular sub-group (AAAAC) of compounds within Group AAAA, $R^{1a}$ and $R^{2a}$ are each selected from hydrogen and allyl.

In another general embodiment (Embodiment AB), $R^1$ is $R^{1b}$ and $R^2$ is $R^{2b}$.

Within Embodiment AB, in one sub-group of compounds (Group ABA), $R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl.

Within Group ABA, in one sub-group of compounds (Group ABAA), $R^{1b}$ and $R^{2b}$ are the same or different and are selected from hydrogen and $C(O)NR^4R^5$. Within Group ABAA, more particularly, $R^4$ and $R^5$ can both be $C_{1-3}$ alkyl. For example, $R^4$ and $R^5$ can both be selected from methyl and ethyl. In one embodiment, $R^{1a}$ is hydrogen and $R^{1b}$ is $C(O)NR^4R^5$. In another embodiment, $R^{1b}$ is hydrogen and $R^{1a}$ is $C(O)NR^4R^5$.

In another sub-group of compounds (Group ABAB) within Group ABA, $R^{1b}$ and $R^{2b}$ are the same or different and are selected from hydrogen and $C(O)R^6$. Within Group ABAB, $R^6$ can be methyl, ethyl, propyl, isopropyl, butyl, 1-methylpropyl, 2-methylpropyl or tert-butyl. In one preferred embodiment (Group ABABA), $R^6$ is $C_{2-4}$ alkyl (more preferably $C_{3-4}$ alkyl such as tert-butyl or isopropyl).

In another sub-group of compounds (Group ABAC) within Group ABA, $R^{1b}$ and $R^{2b}$ are the same or different and are selected from hydrogen and $C(O)OR^6$. Within Group ABAC, $R^6$ can be methyl, ethyl, propyl, isopropyl, butyl, 1-methylpropyl, 2-methylpropyl or tert-butyl. In one preferred embodiment (Group ABACA), $R^6$ is $C_{2-4}$ alkyl (more preferably $C_{3-4}$ alkyl such as tert-butyl or isopropyl).

In another sub-group of compounds (Group ABAD), one of $R^{1b}$ and $R^{2b}$ is $C(O)NR^4R^5$ where $R^4$ and $R^5$ are both $C_{1-4}$ alkyl, and the other of $R^{1b}$ and $R^{2b}$ is selected from $C(O)R^6$ and $C(O)OR^6$ where $R^6$ is as defined in any one of Groups ABAB, ABABA, ABAC and ABACA.

In another sub-group of compounds (Group ABB) within Embodiment AB, $R^{1b}$ and $R^{2b}$ are the same or different and each is hydrogen or a group $C(O)NR^4R^5$, where $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups (e.g. methyl groups) and/or one or two oxo groups.

For example, within Group ABB, in one sub-set of compounds (Group ABBA), the saturated heterocyclic ring is selected from azetidine, pyrrolidine, pyrrolidone, piperidine, piperidone, azepine, piperazine, 4-methylpiperazine, morpholine and thiomorpholine.

In another sub-set of compounds (Group ABBB) within Group ABB, $NR^4R^5$ forms a 5 or 6 membered saturated heterocyclic ring optionally containing a second heteroatom ring member selected from O, N or S and oxidised forms of N and S, the heterocyclic ring being optionally substituted by one or two $C_{1-4}$ alkyl groups (e.g. methyl groups) and/or one or two oxo groups. Within Group ABBB, a preferred sub-set (Group ABBBA) of saturated heterocyclic rings consists of pyrrolidine, piperidine, piperazine, 4-methylpiperazine and morpholine. In one preferred embodiment within Group ABBBA, the saturated heterocyclic ring is pyrrolidine. In another preferred embodiment within Group ABBBA, the saturated heterocyclic ring is morpholine.

In Aspect I, and General Embodiments AA and AB and sub-groups and sub-sets thereof as defined above, at least one of $R^1$ and $R^2$ must be other than hydrogen.

In one subgroup of compounds within each of Aspect I, and General Embodiments AA and AB and sub-groups and sub-sets thereof as defined above, one of $R^1$ and $R^2$ is other than hydrogen and the other is hydrogen. In one general embodiment, $R^2$ is other than hydrogen.

In another sub-group of compounds within each of Aspect I, and General Embodiments AA and AB and sub-groups and sub-sets thereof as defined above, $R^1$ and $R^2$ are both other than hydrogen.

In Aspect I, and General Embodiments AA and AB and sub-groups and sub-sets thereof as defined above, $R^3$ can be any of groups A to G. In one preferred sub-group of compounds within each of Aspect I, and General Embodiments AA and AB and sub-groups and sub-sets thereof as defined above, $R^3$ is a group D:

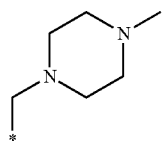

D

According to a second aspect of the invention (Aspect II), there is provided a compound of the formula (2):

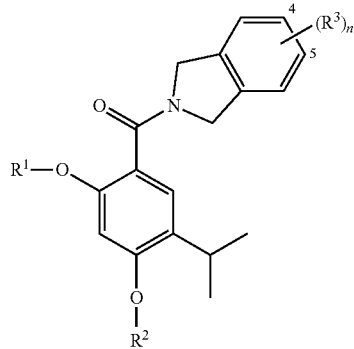

(2)

or a salt, solvate, N-oxide or tautomer thereof;
wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;
$R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;
$R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and
(i) when neither $R^1$ nor $R^2$ is a group $C(O)NR^4R^5$ where $NR^4R^5$ forms an optionally substituted 4 to 7 membered saturated heterocyclic ring as hereinbefore defined, then n is 1 and $R^3$ is attached to either position 4 or position 5 of the isoindoline group and is selected from groups A to G:

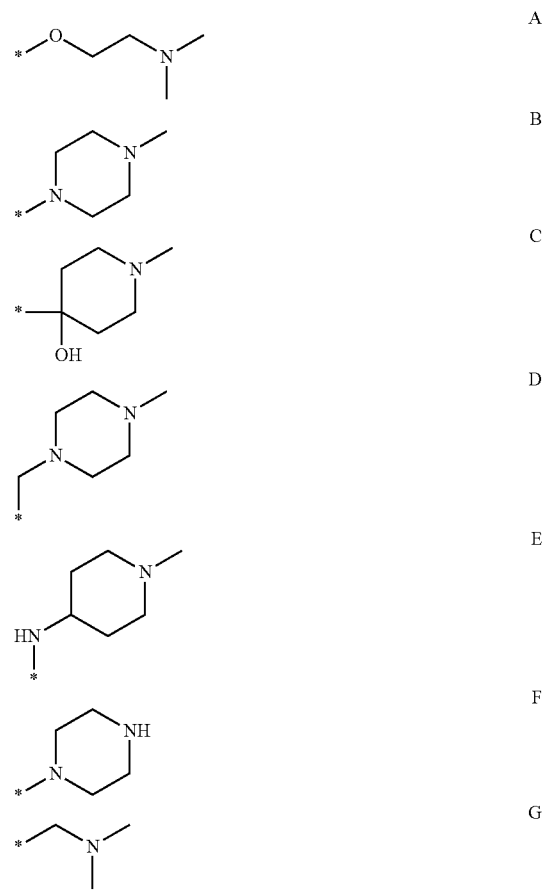

wherein the asterisk denotes the point of attachment to the isoindoline ring; or
(ii) when at least one of $R^1$ and $R^2$ is $C(O)NR^4R^5$ where $NR^4R^5$ forms an optionally substituted 4 to 7 membered saturated heterocyclic ring as hereinbefore defined, then n is 0, 1 or 2 and $R^3$ is selected from a group $R^{1a}$ consisting of:
halogen;
$CO_2R^{14}$ wherein $R^{14}$ is hydrogen or $C_{1-6}$ alkyl;
$C_{1-4}$ alkyl optionally substituted by hydroxy or $C_{1-2}$ alkoxy;
$C_{1-4}$ alkoxy optionally substituted by hydroxy or $C_{1-2}$ alkoxy; or
a group [sol], $CH_2$[sol], $C(O)$[sol], $OCH_2CH_2$[sol] or $OCH_2CH_2CH_2$[sol] where [sol] is selected from the following groups

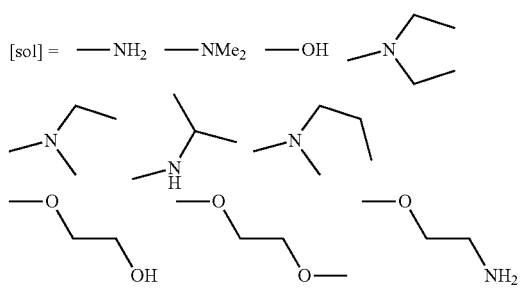

15

-continued

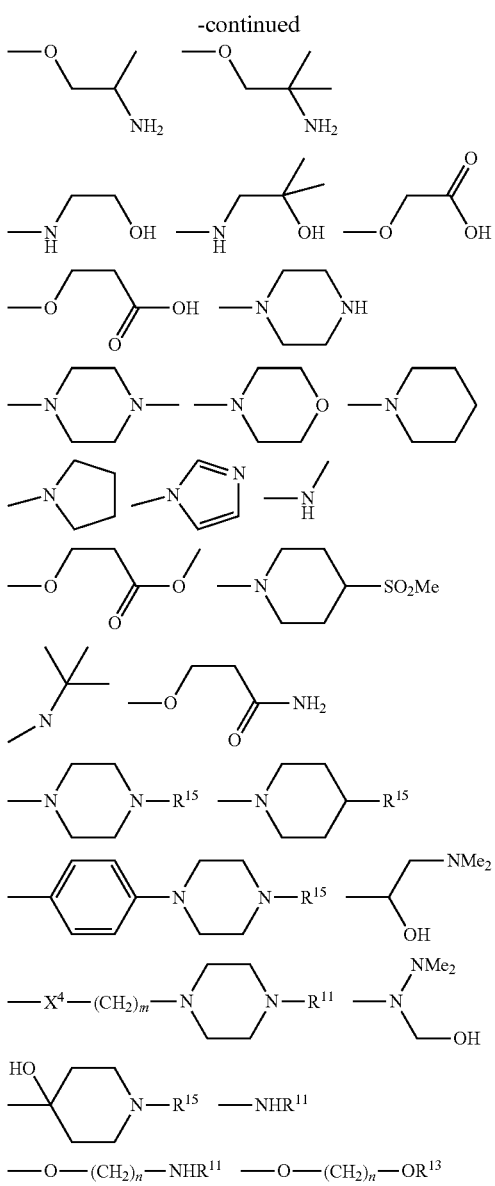

wherein X⁴ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl;

but excluding the compounds dimethyl-carbamic acid 5-dimethylcarbamoyloxy-2-isopropyl-4-[5-(4-methyl-piperazin-1-yl)-1,3-dihydro-isoindole-2-carbonyl]-phenyl ester;

acetic acid 5-acetoxy-4-isopropyl-2-[5-(4-methyl-piperazin-1-yl)-1,3-dihydro-isoindole-2-carbonyl]-phenyl ester;

2,2-dimethyl-propionic acid 5-(2,2-dimethyl-propionyloxy)-4-isopropyl-2-[5-(4-methyl-piperazin-1-yl)-1,3-dihydro-isoindole-2-carbonyl]-phenyl ester; and acetic acid 5-acetoxy-4-isopropyl-2-[5-(4-methyl-piperazin-1-ylmethyl)-1,3-dihydro-isoindole-2-carbonyl]-phenyl ester.

16

According to a third aspect of the invention (Aspect III), there is provided a compound of the formula (3):

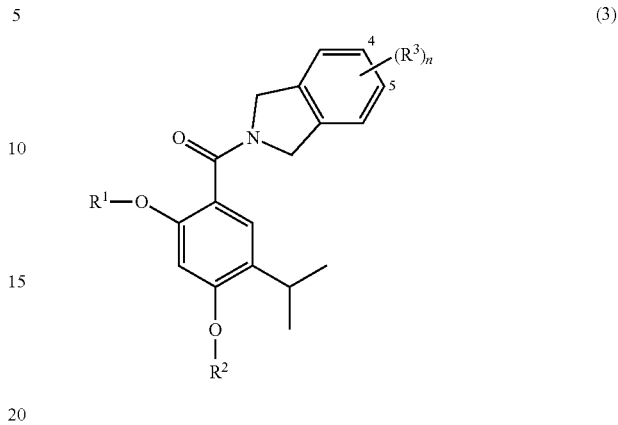

(3)

or a salt, solvate, N-oxide or tautomer thereof;

wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;

$R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;

$R^{1b}$ and $R^{2b}$ are the same or different and are selected from hydrogen, a group $C(O)NR^4R^5$, a group $C(O)R^6$ or a group $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups;

n is 0, 1 or 2; and $R^3$ is selected from a group $R^{3a}$ consisting of:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], $C(O)$[sol], $OCH_2CH_2$[sol] or $OCH_2CH_2CH_2$[sol] where [sol] is selected from the following groups

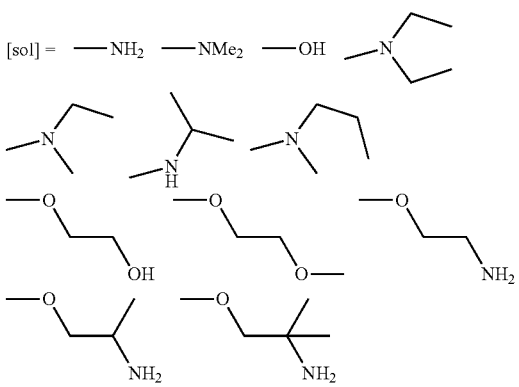

17
-continued

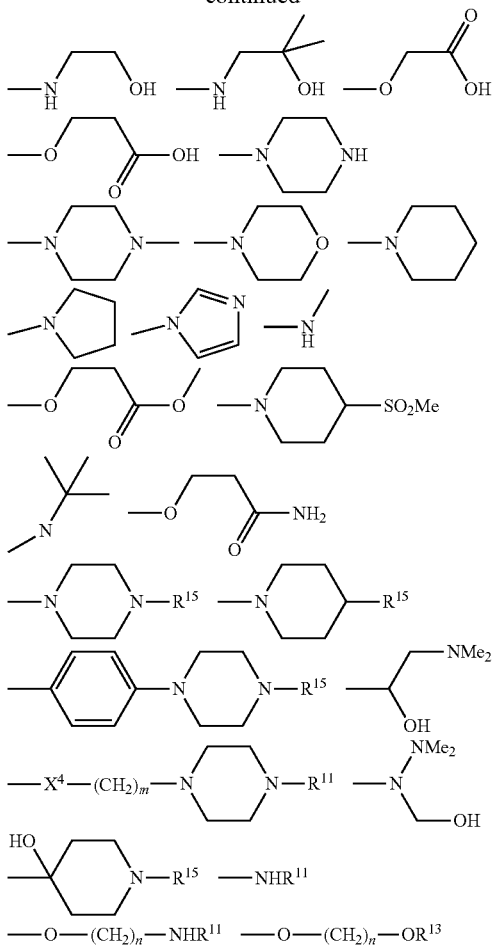

wherein X⁴ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl;

but excluding the compounds dimethyl-carbamic acid 5-dimethylcarbamoyloxy-2-isopropyl-4-[5-(4-methyl-piperazin-1-yl)-1,3-dihydro-isoindole-2-carbonyl]-phenyl ester;

acetic acid 5-acetoxy-4-isopropyl-2-[5-(4-methyl-piperazin-1-yl)-1,3-dihydro-isoindole-2-carbonyl]-phenyl ester;

2,2-dimethyl-propionic acid 5-(2,2-dimethyl-propionyloxy)-4-isopropyl-2-[5-(4-methyl-piperazin-1-yl)-1,3-dihydro-isoindole-2-carbonyl]-phenyl ester; and acetic acid 5-acetoxy-4-isopropyl-2-[5-(4-methyl-piperazin-1-ylmethyl)-1,3-dihydro-isoindole-2-carbonyl]-phenyl ester.

(1,3-dihydro-isoindol-2-yl)-(2-hydroxy-5-isopropyl-4-methoxy-phenyl)-methanone;

[5-(1-dimethylamino-2-hydroxy-ethyl)-1,3-dihydro-isoindol-2-yl]-(5-isopropyl-2,4-dimethoxy-phenyl)-methanone; and

[5-(2-dimethylamino-1-hydroxy-ethyl)-1,3-dihydro-isoindol-2-yl]-(5-isopropyl-2,4-dimethoxy-phenyl)-methanone.

18

According to a fourth aspect of the invention (Aspect IV), there is provided a compound of the formula (4):

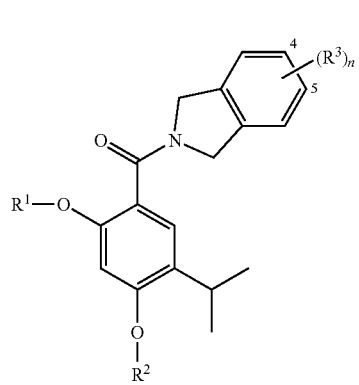

(4)

or a salt, solvate, N-oxide or tautomer thereof;

wherein $R^1$ is selected from $R^{1a}$ and $R^{1b}$; and $R^2$ is selected from $R^{2a}$ and $R^{2b}$; provided that at least one of $R^1$ and $R^2$ is other than hydrogen;

$R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;

$R^{1b}$ and $R^{2b}$ are the same or different and are selected from hydrogen, a group $C(O)NR^4R^5$, a group $C(O)R^6$ or a group $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups;

n is 0, 1 or 2; and $R^3$ is selected from a group $R^{1a}$ consisting of:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], $C(O)$[sol], $OCH_2CH_2$[sol] or $OCH_2CH_2CH_2$[sol] where [sol] is selected from the following groups

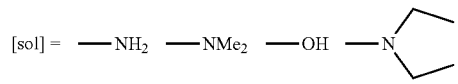

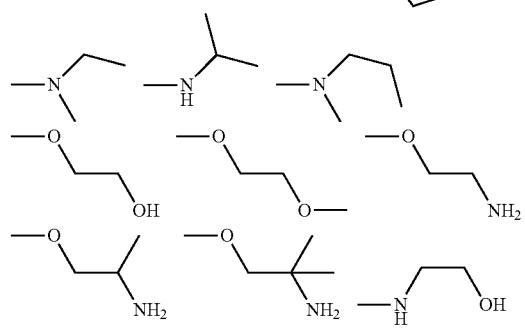

-continued

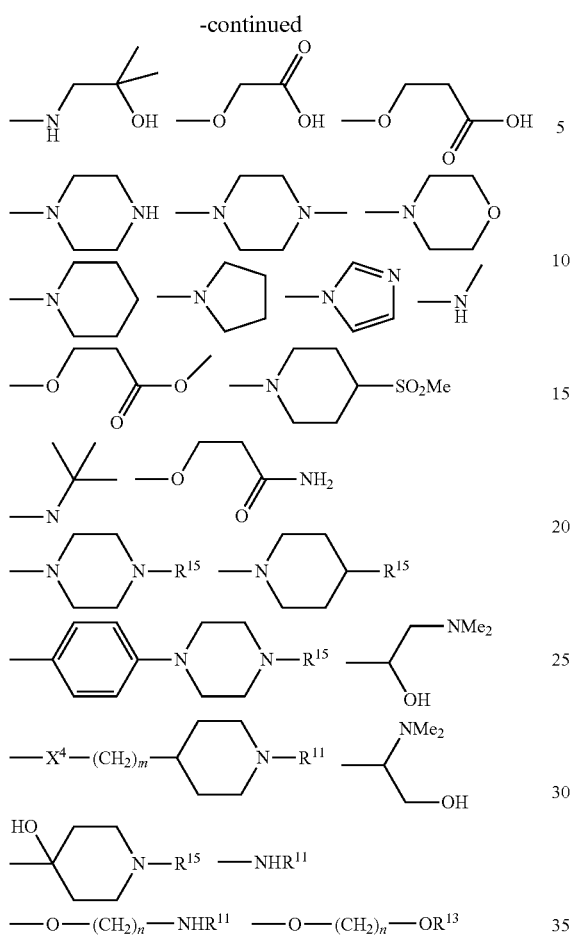

wherein X⁴ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl;

but excluding the compounds dimethyl-carbamic acid 5-dimethylcarbamoyloxy-2-isopropyl-4-[5-(4-methyl-piperazin-1-yl)-1,3-dihydro-isoindole-2-carbonyl]-phenyl ester;

acetic acid 5-acetoxy-4-isopropyl-2-[5-(4-methyl-piperazin-1-yl)-1,3-dihydro-isoindole-2-carbonyl]-phenyl ester;

2,2-dimethyl-propionic acid 5-(2,2-dimethyl-propionyloxy)-4-isopropyl-2-[5-(4-methyl-piperazin-1-yl)-1,3-dihydro-isoindole-2-carbonyl]-phenyl ester; and acetic acid 5-acetoxy-4-isopropyl-2-[5-(4-methyl-piperazin-1-ylmethyl)-1,3-dihydro-isoindole-2-carbonyl]-phenyl ester.

(1,3-dihydro-isoindol-2-yl)-(2-hydroxy-5-isopropyl-4-methoxy-phenyl)-methanone;

[5-(1-dimethylamino-2-hydroxy-ethyl)-1,3-dihydro-isoindol-2-yl]-(5-isopropyl-2,4-dimethoxy-phenyl)-methanone; and

[5-(2-dimethylamino-1-hydroxy-ethyl)-1,3-dihydro-isoindol-2-yl]-(5-isopropyl-2,4-dimethoxy-phenyl)-methanone.

According to a fifth aspect of the invention (Aspect V), there is provided a compound of the formula (5):

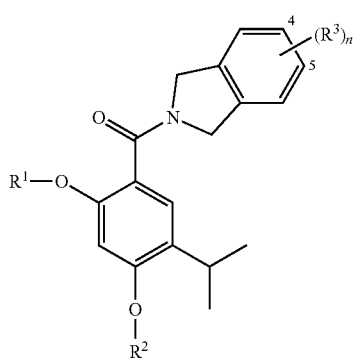

(5)

or a salt, solvate, N-oxide or tautomer thereof;
wherein
n is 0, 1 or 2;
one of $R^1$ and $R^2$ is a group $R^{1c}$; and the other of $R^1$ and $R^2$ is selected from $R^{1a}$ and $R^{1b}$;
$R^{1a}$ is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;
$R^{1b}$ is selected from hydrogen, a group $C(O)NR^4R^5$, a group $C(O)R^6$ or a group $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups;
$R^{1c}$ is a group $C(O)NR^{4c}R^{5c}$ where $NR^{4c}R^{5c}$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups;
$R^3$ is selected from a group $R^{3a}$ consisting of:
halogen;
$CO_2R^{14}$ wherein $R^{14}$ is hydrogen or $C_{1-6}$ alkyl;
$C_{1-4}$ alkyl optionally substituted by hydroxy or $C_{1-2}$ alkoxy;
$C_{1-4}$ alkoxy optionally substituted by hydroxy or $C_{1-2}$ alkoxy; or
a group [sol], $CH_2$[sol], $C(O)$[sol], $OCH_2CH_2$[sol] or $OCH_2CH_2CH_2$[sol] where [sol] is selected from the following groups

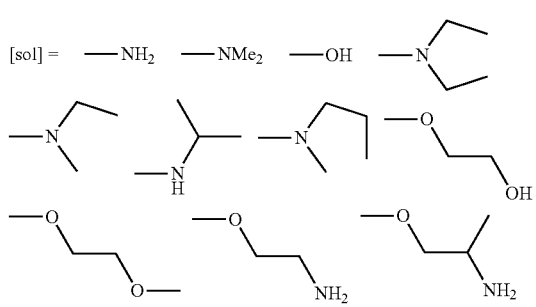

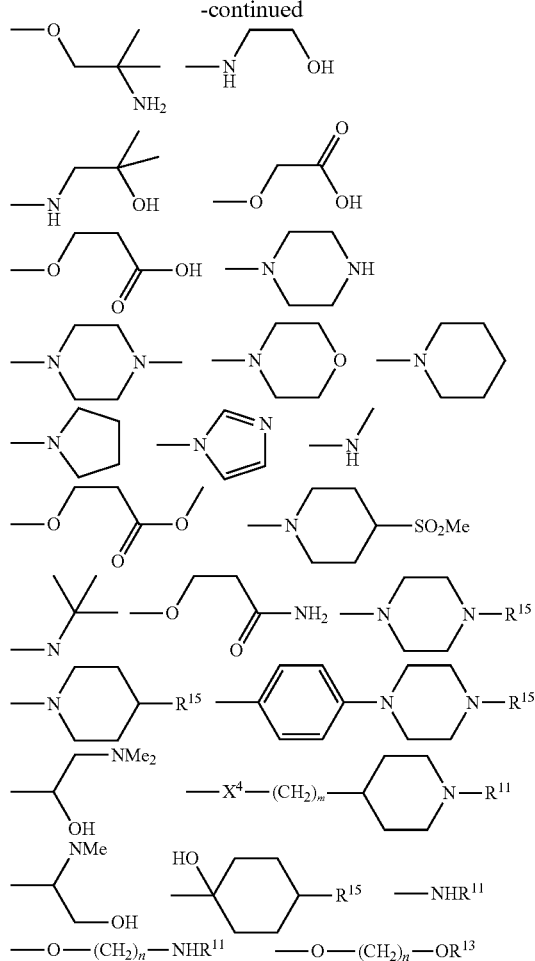

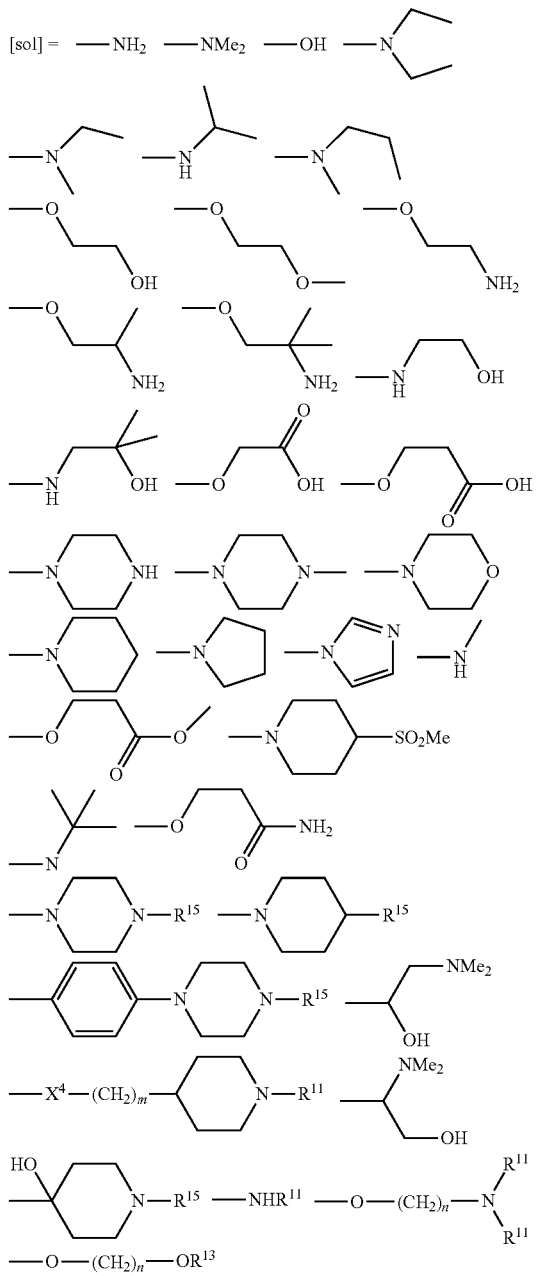

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In further aspects of the invention (Aspects (VI), (VII) and (VIII) as defined herein, there are provided compounds of formulae (1a), (1b) and (1c) as defined in the claims appended hereto.

In each of Aspect (II), Aspect (III), Aspect (IV) and Aspect (V) as defined above, n is preferably 1 or 2. In one general embodiment (Embodiment BA) within each of Aspect (II), Aspect (III), Aspect (IV) and Aspect (V), n is 1.

In one sub-group of compounds (Group BAA) within each of Aspects (II), (III), (IV) and (V) and Embodiment BA, $R^3$ is selected from a group $R^{3b}$ consisting of:

halogen;

$CO_2R^{14}$ wherein $R^{14}$ is hydrogen or $C_{1-2}$ alkyl;

$C_{1-2}$ alkyl optionally substituted by hydroxy or $C_{1-2}$ alkoxy;

$C_{1-2}$ alkoxy optionally substituted by hydroxy or $C_{1-2}$ alkoxy; or a group [sol], $CH_2$[sol], C(O)[sol], $OCH_2CH_2$[sol] or $OCH_2CH_2CH_2$[sol] where [sol] is selected from the following groups wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-4}$ alkyl, $C_{3-6}$ cycloalkyl; $R^{15}$ is hydrogen, $C_{1-4}$ alkyl, $COR^{13}$ or $C(O)OR^{13}$; and $R^{13}$ is $C_{1-4}$ alkyl.

In another sub-group of compounds (Group BAB) within each of Aspects (II), (III), (IV) and (V) and Embodiment BAA, $R^3$ is selected from a group $R^{3c}$ consisting of:

$C_{1-2}$ alkyl optionally substituted by hydroxy or $C_{1-2}$ alkoxy;

$C_{1-2}$ alkoxy optionally substituted by hydroxy or $C_{1-2}$ alkoxy; or a group [sol], $CH_2$[sol], C(O)[sol], $OCH_2CH_2$[sol] or $OCH_2CH_2CH_2$[sol] where [sol] is selected from the following groups

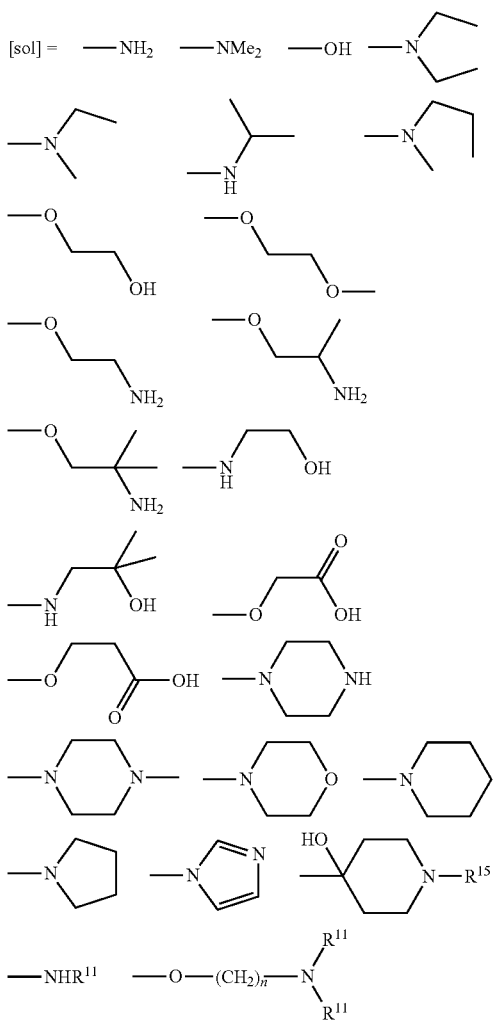

Within each of Aspects (II), (III), (IV) and (V) and Embodiment BAA, preferred compounds are compounds wherein $R^3$ is selected from groups A to G:

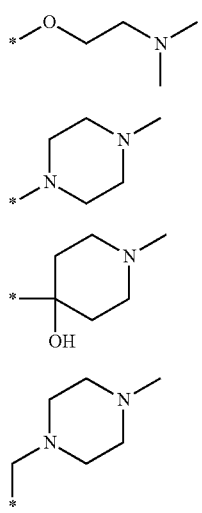

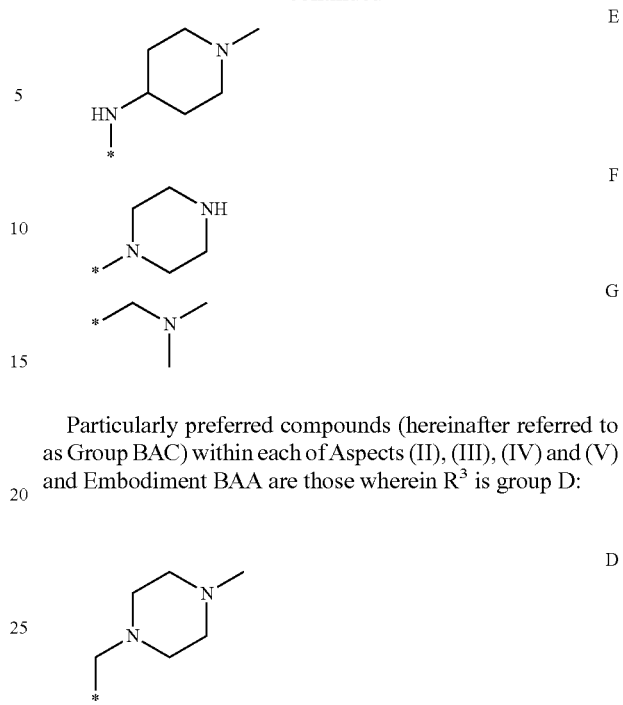

Particularly preferred compounds (hereinafter referred to as Group BAC) within each of Aspects (II), (III), (IV) and (V) and Embodiment BAA are those wherein $R^3$ is group D:

In each of Aspects (II), (III) and (IV), Embodiment BA and Groups BAA, BAB and BAC, $R^1$ and $R^2$ can be as defined in any one of Embodiments AA and AB, and Groups AAA, AAAA, AAAAA, AAAAB, AAAAC, ABA, ABAA, ABAB, ABABA, ABAC, ABACA, ABB, ABBA, ABBB, ABBBA and ABAD as hereinbefore defined and the preferences within each of the said Groups.

In Aspect (V) and Embodiment BA and Groups BAA, BAB and BAC thereof, $R^{1a}$ and $R^{1b}$ can be as defined in any one of Embodiments AA and AB, and Groups AAA, AAAA, AAAAA, AAAAB, AAAAC, ABA, ABAA, ABAB, ABABA, ABAC, ABACA, ABB, ABBA, ABBB, ABBBA and ABAD as hereinbefore defined and the preferences within each of the said Groups; and the saturated heterocyclic ring of the moiety $R^{1c}$ can be as defined in any one of Groups ABBA, ABBB and ABBBA and the preferences within each of the said Groups.

Specific compounds of the invention are:
(4-hydroxy-5-isopropyl-2-methoxy-phenyl)-[5-(4-methyl-piperazin-1-ylmethyl)-1,3-dihydro-isoindol-2-yl]-methanone;
(2-hydroxy-5-isopropyl-4-methoxy-phenyl)-[5-(4-methyl-piperazin-1-ylmethyl)-1,3-dihydro-isoindol-2-yl]-methanone;
(5-isopropyl-2,4-dimethoxy-phenyl)-[5-(4-methyl-piperazin-1-ylmethyl)-1,3-dihydro-isoindol-2-yl]-methanone;
(2-allyloxy-4-hydroxy-5-isopropyl-phenyl)-[5-(4-methyl-piperazin-1-ylmethyl)-1,3-dihydro-isoindol-2-yl]-methanone;
(4-allyloxy-2-hydroxy-5-isopropyl-phenyl)-[5-(4-methyl-piperazin-1-ylmethyl)-1,3-dihydro-isoindol-2-yl]-methanone;
(2,4-bis-allyloxy-5-isopropyl-phenyl)-[5-(4-methyl-piperazin-1-ylmethyl)-1,3-dihydro-isoindol-2-yl]-methanone;
[4-hydroxy-5-isopropyl-2-(methoxymethyloxy)-phenyl]-[5-(4-methyl-piperazin-1-ylmethyl)-1,3-dihydro-isoindol-2-yl]-methanone;

[2-hydroxy-5-isopropyl-4-(methoxymethyloxy)-phenyl]-[5-(4-methyl-piperazin-1-ylmethyl)-1,3-dihydro-isoindol-2-yl]-methanone;

[5-isopropyl-2,4-bis-(methoxymethyloxy)-phenyl]-[5-(4-methyl-piperazin-1-ylmethyl)-1,3-dihydro-isoindol-2-yl]-methanone;

diethyl-carbamic acid 5-diethylcarbamoyloxy-2-isopropyl-4-[5-(4-methyl-piperazin-1-ylmethyl)-1,3-dihydro-isoindole-2-carbonyl]-phenyl ester;

dimethyl-carbamic acid 5-dimethylcarbamoyloxy-2-isopropyl-4-[5-(4-methyl-piperazin-1-ylmethyl)-1,3-dihydro-isoindole-2-carbonyl]-phenyl ester;

2-[2,4-bis-(pyrrolidin-1-ylcarbonyloxy)-5-isopropyl-benzoyl]-5-(4-methyl-piperazin-1-ylmethyl)-1,3-dihydro-isoindole;

2-[2,4-bis-(morpholin-4-ylcarbonyloxy)-5-isopropyl-benzoyl]-5-(4-methyl-piperazin-1-ylmethyl)-1,3-dihydro-isoindole;

diethyl-carbamic acid 5-hydroxy-4-isopropyl-2-[5-(4-methyl-piperazin-1-ylmethyl)-1,3-dihydro-isoindole-2-carbonyl]-phenyl ester;

diethyl-carbamic acid 5-hydroxy-2-isopropyl-4-[5-(4-methyl-piperazin-1-ylmethyl)-1,3-dihydro-isoindole-2-carbonyl]-phenyl ester;

dimethyl-carbamic acid 5-hydroxy-4-isopropyl-2-[5-(4-methyl-piperazin-1-ylmethyl)-1,3-dihydro-isoindole-2-carbonyl]-phenyl ester;

dimethyl-carbamic acid 5-hydroxy-2-isopropyl-4-[5-(4-methyl-piperazin-1-ylmethyl)-1,3-dihydro-isoindole-2-carbonyl]-phenyl ester;

2-[2-(pyrrolidin-1-ylcarbonyloxy)-4-hydroxy-5-isopropyl-benzoyl]-5-(4-methyl-piperazin-1-ylmethyl)-1,3-dihydro-isoindole;

2-[4-(pyrrolidin-1-ylcarbonyloxy)-2-hydroxy-5-isopropyl-benzoyl]-5-(4-methyl-piperazin-1-ylmethyl)-1,3-dihydro-isoindole;

2-[2-(morpholin-4-ylcarbonyloxy)-4-hydroxy-5-isopropyl-benzoyl]-5-(4-methyl-piperazin-1-ylmethyl)-1,3-dihydro-isoindole;

2-[4-(morpholin-4-ylcarbonyloxy)-2-hydroxy-5-isopropyl-benzoyl]-5-(4-methyl-piperazin-1-ylmethyl)-1,3-dihydro-isoindole;

carbonic acid tert-butyl ester 5-dimethylcarbamoyloxy-4-isopropyl-2-[5-(4-methyl-piperazin-1-ylmethyl)-1,3-dihydro-isoindole-2-carbonyl]-phenyl ester;

carbonic acid 5-tert-butoxycarbonyloxy-4-isopropyl-2-[5-(4-methyl-piperazin-1-ylmethyl)-1,3-dihydro-isoindole-2-carbonyl]-phenyl ester tert-butyl ester;

2,2-dimethyl-propionic acid 5-(2,2-dimethyl-propionyloxy)-2-isopropyl-4-[5-(4-methyl-piperazin-1-ylmethyl)-1,3-dihydro-isoindole-2-carbonyl]-phenyl ester;

isobutyric acid 5-isobutyryloxy-2-isopropyl-4-[5-(4-methyl-piperazin-1-ylmethyl)-1,3-dihydro-isoindole-2-carbonyl]-phenyl ester;

and salts, solvates, tautomers and N-oxides thereof.

One group of preferred compounds of the invention consists of dimethyl-carbamic acid 5-hydroxy-4-isopropyl-2-[5-(4-methyl-piperazin-1-ylmethyl)-1,3-dihydro-isoindole-2-carbonyl]-phenyl ester; and dimethyl-carbamic acid 5-hydroxy-2-isopropyl-4-[5-(4-methyl-piperazin-1-ylmethyl)-1,3-dihydro-isoindole-2-carbonyl]-phenyl ester;

and salts, solvates, tautomers and N-oxides thereof.

Within the aforesaid group of preferred compounds of the invention, one particular compound is:

dimethyl-carbamic acid 5-hydroxy-2-isopropyl-4-[5-(4-methyl-piperazin-1-ylmethyl)-1,3-dihydro-isoindole-2-carbonyl]-phenyl ester;

and salts, solvates, tautomers and N-oxides thereof.

Compounds of the formulae (1), (1a), (1b), (1c), (2), (3), (4) and (5) and sub-groups thereof as defined herein are pro-drugs of the compounds disclosed in our earlier application PCT/GB2006/001382. Thus, it is envisaged that compounds of the formulae (1), (1a), (1b), (1c), (2), (3), (4) and (5) will be converted in vivo to give compounds wherein $R^1$ and $R^2$ are both OH.

In further aspects, the invention provides:

A compound of the formula (1), (1a), (1b), (1c), (2), (3), (4) or (5) or any Embodiments, sub-groups, sub-sets, preferences or examples thereof as defined herein for use in the prophylaxis or treatment of a disease state or condition mediated by Hsp90.

The use of a compound of the formula (1), (1a), (1b), (1c), (2), (3), (4) or (5) or any Embodiments, sub-groups, sub-sets, preferences or examples thereof as defined herein for the manufacture of a medicament for the prophylaxis or treatment of a disease state or condition mediated by Hsp90.

A method for the prophylaxis or treatment of a disease state or condition mediated by Hsp90, which method comprises administering to a subject in need thereof a compound of the formula (1), (1a), (1b), (1c), (2), (3), (4) or (5) or any Embodiments, sub-groups, sub-sets, preferences or examples thereof as defined herein.

A compound of the formula (1), (1a), (1b), (1c), (2), (3), (4) or (5) or any Embodiments, sub-groups, sub-sets, preferences or examples thereof as defined herein for use in alleviating or reducing the incidence of a disease state or condition mediated by Hsp90.

The use of a compound of the formula (1), (1a), (1b), (1c), (2), (3), (4) or (5) or any Embodiments, sub-groups, sub-sets, preferences or examples thereof as defined herein.

A compound of the formula (1), (1a), (1b), (1c), (2), (3), (4) or (5) or any Embodiments, sub-groups, sub-sets, preferences or examples thereof as defined herein for use in treating a disease or condition comprising or arising from abnormal cell growth in a mammal.

The use of a compound of the formula (1), (1a), (1b), (1c), (2), (3), (4) or (5) or any Embodiments, sub-groups, sub-sets, preferences or examples thereof as defined herein for the manufacture of a medicament for treating a disease or condition comprising or arising from abnormal cell growth in a mammal A method for treating a disease or condition comprising or arising from abnormal cell growth in a mammal, which method comprises administering to the mammal a compound of the formula (1), (1a), (1b), (1c), (2), (3), (4) or (5) or any Embodiments, sub-groups, sub-sets, preferences or examples thereof as defined herein in an amount effective in inhibiting abnormal cell growth.

A compound of the formula (1), (1a), (1b), (1c), (2), (3), (4) or (5) or any Embodiments, sub-groups, sub-sets, preferences or examples thereof as defined herein for use in alleviating or reducing the incidence of a disease or condition comprising or arising from abnormal cell growth in a mammal The use of a compound of the formula (1), (1a), (1b), (1c), (2), (3), (4) or (5) or any Embodiments, sub-groups, sub-sets, preferences or examples thereof as defined herein for the manufacture of a medicament for alleviating or reducing the incidence of a disease or condition comprising or arising from abnormal cell growth in a mammal A method for alleviating or reducing the incidence of a disease or condition comprising or arising from abnormal cell growth in a mammal, which method comprises administering to the mammal a compound of the formula (1), (1a), (1b), (1c), (2), (3), (4) or (5) or any Embodiments, sub-groups, sub-sets, preferences or examples thereof as defined herein in an amount effective in inhibiting abnormal cell growth.

A method for treating a disease or condition comprising or arising from abnormal cell growth in a mammal, the method comprising administering to the mammal a compound of the formula (1), (1a), (1b), (1c), (2), (3), (4) or (5) or any Embodiments, sub-groups, sub-sets, preferences or examples thereof as defined herein in an amount effective to inhibit Hsp90 activity.

A method for alleviating or reducing the incidence of a disease or condition comprising or arising from abnormal cell growth in a mammal, the method comprising administering to the mammal a compound of the formula (1), (1a), (1b), (1c), (2), (3), (4) or (5) or any Embodiments, sub-groups, sub-sets, preferences or examples thereof as defined herein in an amount effective to inhibit Hsp90 activity.

A compound of the formula (1), (1a), (1b), (1c), (2), (3), (4) or (5) or any Embodiments, sub-groups, sub-sets, preferences or examples thereof as defined herein for use as an inhibitor of Hsp90.

A method of inhibiting Hsp90, which method comprises contacting the Hsp90 with an Hsp90-inhibiting compound of the formula (1), (1a), (1b), (1c), (2), (3), (4) or (5) or any Embodiments, sub-groups, sub-sets, preferences or examples thereof as defined herein.

A compound of the formula (1), (1a), (1b), (1c), (2), (3), (4) or (5) or any Embodiments, sub-groups, sub-sets, preferences or examples thereof as defined herein for use in modulating a cellular process (for example cell division) by inhibiting the activity of Hsp90.

A method of modulating a cellular process (for example cell division) by inhibiting the activity of Hsp90 using a compound of the formula (1), (1a), (1b), (1c), (2), (3), (4) or (5) or any Embodiments, sub-groups, sub-sets, preferences or examples thereof as defined herein.

A compound of the formula (1), (1a), (1b), (1c), (2), (3), (4) or (5) or any Embodiments, sub-groups, sub-sets, preferences or examples thereof as defined herein for use in the prophylaxis or treatment of a disease state as described herein.

The use of a compound of the formula (1), (1a), (1b), (1c), (2), (3), (4) or (5) or any Embodiments, sub-groups, sub-sets, preferences or examples thereof as defined herein for the manufacture of a medicament, wherein the medicament is for any one or more of the uses defined herein.

A pharmaceutical composition comprising a compound of the formula (1), (1a), (1b), (1c), (2), (3), (4) or (5) or any Embodiments, sub-groups, sub-sets, preferences or examples thereof as defined herein and a pharmaceutically acceptable carrier.

A pharmaceutical composition comprising a compound of the formula (1), (1a), (1b), (1c), (2), (3), (4) or (5) or any Embodiments, sub-groups, sub-sets, preferences or examples thereof as defined herein and a pharmaceutically acceptable carrier in a form suitable for oral administration.

A pharmaceutical composition comprising a compound of the formula (1), (1a), (1b), (1c), (2), (3), (4) or (5) or any Embodiments, sub-groups, sub-sets, preferences or examples thereof as defined herein and a pharmaceutically acceptable carrier in a form suitable for parenteral administration, for example by intravenous (i.v.) administration.

A pharmaceutical composition comprising a compound of the formula (1), (1a), (1b), (1c), (2), (3), (4) or (5) or any Embodiments, sub-groups, sub-sets, preferences or examples thereof as defined herein and a pharmaceutically acceptable carrier in a form suitable for intravenous (i.v.) administration by injection or infusion.

A compound of the formula (1), (1a), (1b), (1c), (2), (3), (4) or (5) or any Embodiments, sub-groups, sub-sets, preferences or examples thereof as defined herein for use in medicine.

A compound as defined herein for any of the uses and methods set forth above, and as described elsewhere herein.

A compound of the formula (1), (1a), (1b), (1c), (2), (3), (4) or (5) or any Embodiments, sub-groups, sub-sets, preferences or examples thereof as defined herein for use in treatment or prophylaxis of a disease state or condition in a patient who has been screened and has been determined as suffering from, or being at risk of suffering from, a disease or condition which would be susceptible to treatment with a compound having activity against Hsp90.

The use of a compound of the formula (1), (1a), (1b), (1c), (2), (3), (4) or (5) or any Embodiments, sub-groups, sub-sets, preferences or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90.

A method for the diagnosis and treatment of a disease state or condition mediated by Hsp90, which method comprises (i) screening a patient to determine whether a disease or condition from which the patient is or may be suffering is one which would be susceptible to treatment with a compound having activity against Hsp90; and (ii) where it is indicated that the disease or condition from which the patient is thus susceptible, thereafter administering to the patient a compound of the formula (1), (1a), (1b), (1c), (2), (3), (4) or (5) or any Embodiments, sub-groups, sub-sets, preferences or examples thereof as defined herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

GENERAL PREFERENCES AND DEFINITIONS

The compounds of the invention are pro-drugs of hydroxy-benzoic acid amide Hsp90 inhibitors disclosed in our earlier International application PCT/GB2006/001382. For convenience, the compounds of PCT/GB2006/001382 may be referred to variously in this application as "the parent compounds" or "the phenolic compounds". References to the pro-drugs being "derived" from the "parent compounds" or "phenolic compounds" is only intended to imply a structural relationship and is not intended to imply any particular method of preparing the prodrugs. Thus, the pro-drugs may be prepared from the compounds of PCT/GB2006/001382 as described below, or they may be prepared by methods that do not involve the intermediacy of a phenolic compound of PCT/GB2006/001382.

In this section, as in all other sections of this application, unless the context indicates otherwise, a reference to a compound of formula (1) includes all Embodiments, sub-groups, sub-sets, preferences, embodiments, examples and particular compounds defined herein.

Similarly, a reference to a compound of formula (2) includes all Embodiments, sub-groups, sub-sets, preferences, embodiments, examples and particular compounds defined herein, and a reference to a compound of formula (3) or (4) or (5) includes all Embodiments, sub-groups, sub-sets, preferences, embodiments, examples and particular compounds defined herein.

Moreover, a reference to a compound of formula (1), (1a), (1b), (1c), (2), (3), (4) or (5) and Embodiments, sub-groups, thereof includes ionic forms, salts, solvates, isomers, tautomers and isotopes thereof, as discussed below.

The compounds of formulae (1), (1a), (1b), (1c), (2), (3), (4) and (5) and Embodiments, sub-groups, sub-sets thereof, including ionic forms, salts, solvates, isomers, tautomers and isotopes thereof as defined herein may be referred to for convenience as "the compounds of the invention" or, in the singular, "a compound of the invention".

As used herein, the term "treatment" and the related terms "treat" and "treating" refer to both prophylactic or preventative treatment as well as curative or palliative treatment of pain. Thus, the term encompasses situations where pain is already being experienced by a subject or patient, as well as situations where pain is not currently being experienced but is expected to arise. The term "treatment", "treat", "treating" and related terms also cover both complete and partial pain reduction or prevention. Thus, for example, the compounds of the invention may prevent existing pain from worsening, or they reduce or even eliminate pain. When used in a prophylactic sense, the compounds may prevent any pain from developing or they may lessen the extent of pain that may develop.

As used herein, the term "modulation", as applied to the activity of the heat shock protein Hsp90, is intended to define a change in the level of biological activity of the heat shock protein. Thus, modulation encompasses physiological changes which effect an increase or decrease in the relevant heat shock protein activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of heat shock protein activity. Thus, modulation may imply elevated/suppressed expression or over- or under-expression of the heat shock protein, including, but not limited to gene amplification (i.e. multiple gene copies) and/or increased or decreased expression by a transcriptional effect, as well as hyper- (or hypo-)activity and (de)activation of the heat shock protein (including (de)activation) by mutation(s). The terms "modulated", "modulating" and "modulate" are to be interpreted accordingly.

As used herein, the term "mediated", as used e.g. in conjunction with the heat shock protein as described herein (and applied for example to various physiological processes, diseases, states, conditions, therapies, treatments or interventions) is intended to operate limitatively so that the various processes, diseases, states, conditions, treatments and interventions to which the term is applied are those in which heat shock protein Hsp90 plays a biological role. In cases where the term is applied to a disease, state or condition, the biological role played by heat shock protein Hsp90 may be direct or indirect and may be necessary and/or sufficient for the manifestation of the symptoms of the disease, state or condition (or its aetiology or progression). Thus, heat shock protein Hsp90 activity (and in particular aberrant levels of heat shock protein Hsp90 activity, e.g. Hsp90 over-expression) need not necessarily be the proximal cause of the disease, state or condition: rather, it is contemplated that the heat shock protein Hsp90 mediated diseases, states or conditions include those having multifactorial aetiologies and complex progressions in which Hsp90 is only partially involved. In cases where the term is applied to treatment, prophylaxis or intervention (e.g. in the "Hsp90-mediated treatments" and "Hsp90-mediated prophylaxis" of the invention), the role played by Hsp90 may be direct or indirect and may be necessary and/or sufficient for the operation of the treatment, prophylaxis or outcome of the intervention. Thus, a disease state or condition mediated by Hsp90 includes the development of resistance to any particular cancer drug or treatment (including in particular resistance to one or more of the signalling inhibitors described herein).

The term "intervention" is a term of art used herein to define any agency which effects a physiological change at any level. Thus, the intervention may comprise the induction or repression of any physiological process, event, biochemical pathway or cellular/biochemical event. The interventions of the invention typically effect (or contribute to) the therapy, treatment or prophylaxis of a disease or condition.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "in combination" may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The following general preferences and definitions shall apply to the substituents $R^1$, $R^2$ and $R^3$ unless the context indicates otherwise.

The term "alkyl" as used herein is used in its conventional sense to mean a group of the empirical formula $C_nH_{2n+1}$ where n is an integer (e.g. 1 to 6). The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 6 carbon atoms, particular examples are $C_{1-4}$ alkyl groups (e.g. $C_{1-3}$ alkyl groups or $C_{1-2}$ alkyl groups or $C_{2-3}$ alkyl groups or $C_{2-4}$ alkyl groups).

The term "cycloalkyl" as used herein is used in its conventional sense to denote a cyclic alkyl group of the empirical formula $C_nH_{2n-1}$ where n is an integer. Examples of such cycloalkyl groups include cyclopropyl, cyclobutyl, cyclopentyl and cyclohexyl.

The term "alkenyl" as used herein is used in its conventional sense to mean an acyclic hydrocarbon group containing one or more carbon-carbon double bonds, and more preferably a single carbon-carbon double bond. Examples of alkenyl groups include ethenyl (vinyl), 1-propenyl, 2-propenyl (allyl), isopropenyl, butenyl and buta-1,4-dienyl.

The term "alkynyl" as used herein is used in its conventional sense to mean a hydrocarbon group containing a carbon-carbon triple bond. A preferred akynyl group is a propargyl group.

The prefix "$C_{x-y}$" (where x and y are integers) as used herein refers to the number of carbon atoms in a given group. Thus, a $C_{1-4}$ alkyl group contains from 1 to 4 carbon atoms, a $C_{3-6}$ cycloalkyl group contains from 3 to 6 carbon atoms, a $C_{1-4}$ alkoxy group contains from 1 to 4 carbon atoms, and so on.

The term "alkoxy" as used herein is used in its conventional sense to mean a group of the empirical formula $OC_nH_{2n+1}$ where n is an integer (e.g. 1 to 6). Examples of alkoxy groups are methox, ethoxy, propoxy, isopropoxy, butoxy, 1-methylpropoxy, 2-methylpropoxy and tert-butoxy.

The term "saturated heterocyclic ring" as used herein to a cyclic group containing no multiple bonds (e.g. double bonds) between adjacent ring members and containing one or more heteroatom ring members with the remaining ring members being carbon atoms. Unless stated otherwise, the saturated heterocyclic ring contains one or two heteroatom ring members selected from O, N and S and oxidized forms of N and S. Preferred saturated heterocyclic groups are those having 5 or six ring members. Examples of saturated heterocyclic groups include azetidine, pyrrolidine, piperidine, azepine, morpholine, thiomorpholine, thiomorpholine S-oxide and S,S-dioxide, piperazine, and N-methyl piperazine. Particular saturated heterocyclic groups are pyrrolidine, piperidine, morpholine, piperazine, and N-methyl piperazine.

The term "aryl" as used herein is used in its conventional sense to denote an aromatic group wherein the ring members are all carbon atoms. The aryl group may be monocyclic or bicyclic and hence may be a phenyl group or a naphthyl group. The aryl group may be unsubstituted or substituted with up to 4 substituents, more typically up to 3 substituents and preferably up to 2 substituents. In the context of the substituent group $R^{12}$ herein, the aryl group is preferably monocyclic and is an optionally substituted phenyl group wherein the optional substituents for the phenyl group are selected from $C_{1-4}$ alkyl (e.g. methyl), halogen (e.g. chlorine, fluorine or bromine), cyano, trifluoromethyl, trifluoromethoxy, difluoromethoxy, $C_{1-4}$ alkoxy (e.g. methoxy), methylenedioxy. In one general embodiment, an aryl group forming part of the substituent group $R^{12}$ may be unsubstituted phenyl or phenyl substituted by one or two substituents selected from methyl, methoxy, fluorine or chlorine.

The various functional groups and substituents making up the compounds of the formulae (1), (1a), (1b), (1c), (2), (3), (4), (5) and Embodiments, sub-groups, subsets and preferences and examples thereof are typically chosen such that the molecular weight of the compound of the invention does not exceed 1000. More usually, the molecular weight of the compound will be less than 750, for example less than 700, or less than 650, or less than 600, or less than 550. More preferably, the molecular weight is less than 525 and, for example, is 500 or less.

Salts, Solvates, Tautomers, Isomers, N-Oxides and Isotopes

A reference to a compound of the formulae (1), (1a), (1b), (1c), (2), (3), (4), (5) and Embodiments, sub-groups, subsets and preferences and examples thereof also includes ionic forms, salts, solvates, isomers, tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof Many of the compounds may exist in the form of salts, for example acid addition salts or, in certain cases salts of organic and inorganic bases such as phenolate, carboxylate, sulphonate and phosphate salts. All such salts are within the scope of this invention, and references to compounds of the formulae (1), (1a), (1b), (1c), (2), (3), (4), (5) and Embodiments, sub-groups, subsets and preferences and examples thereof include the salt forms of the compounds.

The salts of the present invention may be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formulae (1), (1a), (1b), (1c), (2), (3), (4), (5) and Embodiments, sub-groups, subsets and preferences and examples thereof contain an amine function, these may form quaternary ammonium salts, for example by reaction with an alkylating agent according to methods well known to the skilled person. Such quaternary ammonium compounds are within the scope of formulae (1), (1a), (1b), (1c), (2), (3), (4), (5) and Embodiments, sub-groups, subsets and preferences and examples thereof.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formulae (1), (1a), (1b), (1c), (2), (3), (4), (5) and Embodiments, sub-groups, subsets and preferences and examples thereof containing an amine function may also form N-oxides. A reference herein to a compound of any of the formulae (1), (1a), (1b), (1c), (2), (3), (4), (5) and Embodiments, sub-groups, subsets and preferences and examples thereof that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides may be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides may be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formulae (1), (1a), (1b), (1c), (2), (3), (4), (5) and Embodiments, sub-groups, subsets and preferences and examples thereof may exist in a number of different geometric isomeric, and tautomeric forms and references to compounds of the formulae (1), (1a), (1b), (1c), (2), (3), (4), (5) and Embodiments, sub-groups, subsets and preferences and examples thereof include all such forms. For the avoidance of doubt, where a compound can exist in one of several geometric isomeric or tautomeric forms and only one is specifically described or shown, all others are nevertheless embraced by formulae (1), (1a), (1b), (1c), (2), (3), (4), (5) and Embodiments, sub-groups, subsets and preferences and examples thereof.

Examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

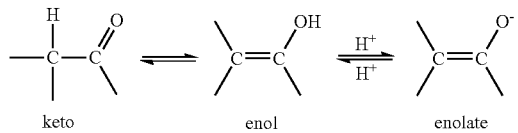

Where compounds of the formulae (1), (1a), (1b), (1c), (2), (3), (4), (5) and Embodiments, sub-groups, subsets and preferences and examples thereof contain one or more chiral centres, and can exist in the form of two or more optical isomers, references to compounds of the formulae (1), (1a), (1b), (1c), (2), (3), (4), (5) and Embodiments, sub-groups, subsets and preferences and examples thereof include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers may be separated by a number of techniques including chiral chromatography (chromatography on a chiral support) and such techniques are well known to the person skilled in the art.

As an alternative to chiral chromatography, optical isomers may be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formulae (1), (1a), (1b), (1c), (2), (3), (4), (5) and Embodiments, sub-groups, subsets and preferences and examples thereof exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing compounds of the formulae (1), (1a), (1b), (1c), (2), (3), (4), (5) and Embodiments, sub-groups, subsets and preferences and examples thereof having one or more chiral centres, wherein at least 55% (e.g. at least 60%, 65%, 70%, 75%, 80%, 85%, 90% or 95%) of the compound of the invention is present as a single optical isomer (e.g. enantiomer or diastereoisomer). In one general embodiment, 99% or more (e.g. substantially all) of the total amount of the compound of the formulae (1), (1a), (1b), (1c), (2), (3), (4), (5) and Embodiments, sub-groups, subsets and preferences and examples thereof may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by formulae (1), (1a), (1b), (1c), (2), (3), (4), (5) and Embodiments, sub-groups, subsets and preferences and examples thereof are any polymorphic forms of the compounds, solvates (e.g. hydrates) and complexes (e.g. inclusion complexes or clathrates with compounds such as cyclodextrins, or complexes with metals) of the compounds.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates may be prepared by recrystallising the compounds of the invention with a solvent or mixture of solvents containing the solvating solvent. Whether or not a solvate has been formed in any given instance may be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Biological Activity and Therapeutic Uses

The compounds of the formulae (1), (1a), (1b), (1c), (2), (3), (4), (5) and Embodiments, sub-groups, subsets and preferences and examples thereof are considered to be pro-drugs of compounds that are inhibitors of Hsp90

The pro-drug compounds of the invention may have a number of advantages with respect to their parent compounds. For example, they may provide improved oral bioavailability, e.g. by virtue of improved intestinal absorption.

Furthermore, by forming a pro-drug, conjugation and/or metabolism of the parent compound may be substantially reduced.

The pro-drug compounds of the invention are expected to be beneficial in the treatment of wide spectrum of proliferative disorders. Examples of such proliferative disorders include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including, but not limited to acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, neuroblastoma, glioma (a High grade glioma) or schwannoma; melanoma (e.g. malignant or metastatic melanoma); seminoma; teratocarcinoma; osteosarcoma; keratoacanthoma; thyroid follicular cancer; or Kaposi's sarcoma. A further example of a tumour of mesenchymal origin is Ewing's sarcoma.

One sub-group of cancers includes a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, gall bladder, ovary, pancreas e.g. exocrine pancreatic carcinoma, stomach, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, glioma (a High grade glioma); melanoma (e.g. malignant or metastatic melanoma); osteosarcoma; or thyroid follicular cancer. A further example of a tumour of mesenchymal origin is Ewing's sarcoma.

One preferred group of cancers consists of solid tumours selected from metastatic breast cancer which is HER2 positive; adenocarcinoma of the prostate; metastatic melanoma; non-small cell carcinoma of the lung (NSCLC); small cell carcinoma of the lung (SCLC); high grade gliomas; gastrointestinal stromal tumors (GIST); colorectal cancer; glioblastoma; melanoma; metastatic thyroid cancer; prostate cancer; and rectal cancer.

Within this group of cancers, a particular subgroup consists of colorectal cancer; glioblastoma; melanoma; metastatic thyroid cancer; prostate cancer; and rectal cancer.

The cancers may be cancers which are sensitive to Hsp90 inhibition, and such cancers may be determined by a method as set out in the section headed "Methods of Diagnosis".

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of both lymphoid and myeloid lineage, for example acute lymphoblastic leukemia, chronic lymphocytic leukaemia (Both T and B cell), acute myeloid leukaemia, chronic myeloid leukaemia, mantle cell lymphoma and B-cell lymphoma (such as diffuse large B cell lymphoma) and optionally further includes chronic myelogenous leukaemia and multiple myeloma.

A preferred sub-set of cancers consists of ErbB2-positive breast, prostate, lung, and gastric cancer; chronic myeloid leukemia; androgen receptor dependent prostate cancer; Flt3-dependent acute myeloid leukaemia; melanoma associated with Braf mutation; multiple myeloma; velcade refractory multiple myeloma; and gastrointestinal stromal tumours (GIST).

Of these, particularly preferred cancers are multiple myelomas and velcade refractory tumour types as defined herein.

Another preferred sub-set of cancers consists of hormone refractory prostate cancer, metastatic melanoma, HER2 positive breast cancer, mutant EGFR positive non-small cell lung carcinoma and Gleevec resistant gastrointestinal stromal tumours.

A further preferred sub-set of cancers consists of hormone refractory prostate cancer, metastatic melanoma, HER2 positive breast cancer, mutant EGFR positive non-small cell lung carcinoma, Small Cell Lung Carcinoma and gastrointestinal stromal tumours.

Hsp90 inhibitors could also be used to treat other conditions such as viral infections, parasitic disease, autoimmune diseases (e.g. multiple sclerosis and lupus erythematosus), neuro-degenerative disorders (e g Alzheimer's disease), inflammation, Type I and II diabetes, atherosclerosis, cardiac disease and xeroderma pigmentosum (an inherited multisystem disorder of DNA repair which is not a cancer but which has a predisposition to UV-induced skin cancer).

Hsp90 inhibitors could also have clinical benefit in transplantation and immunosuppression.

Hsp90 inhibitors may also have clinical benefit in the previously described diseases when used in combination with existing or new therapeutic agents.

Based on the activities of Hsp90 client proteins and experimental evidence, the following disorders may be particularly sensitive to treatment by Hsp90 inhibitors.

ErbB2-positive Breast, Prostate, Lung, and Gastric Cancer

Overexpression of ErbB2 (HER-2) occurs in approximately 30% of breast cancers and is linked to poor prognosis and drug resistance (Tsugawa et. al., 1993. Oncology 1993; 50: 418).

Mutant EGFR in Lung Cancer

Somatic mutations in the kinase domain of the epidermal growth factor receptor (EGFR), including L858R and exon 19 deletions, underlie responsiveness to gefitinib and erlotinib in non-small cell lung cancer (NSCLC). Acquired resistance to these tyrosine kinase inhibitors is in some cases mediated by a second mutation, T790M. Ansamycin antibiotics, such as geldanamycin, potently inhibit heat shock protein 90 (Hsp90), promoting ubiquitin-mediated degradation of oncogenic kinases that require the chaperone for proper conformational folding. Exposure of EGFR-mutant cell lines to geldanamycin induced marked depletion of phospho-Akt and cyclin D1 as well as apoptosis. These data suggest mutational activation of EGFR is associated with dependence on Hsp90 for stability and that Hsp90 inhibition may represent a novel strategy for the treatment of EGFR-mutant NSCLC.

Chronic Myeloid Leukemia

The aberrant BCR-Abl protein is created through a chromosomal translocation and results in a constitutively active Abl kinase domain. This translocation event has been shown to be causal for CML. P210BcrAbl is a known client protein for Hsp90. Treatment of the BCR-Abl positive cell line K562 with an hsp90 inhibitor induced apoptosis. The Bcr-Abl inhibitor Gleevec® also induces apoptosis in K562 cells; however Gleevec® resistant K562 cells still retain sensitivity towards Hsp90 inhibitors (Gone et. al. 2002, Blood 100: 3041-3044).

Androgen Receptor Dependent Prostate Cancer

The androgen receptor kinase is an Hsp90 client protein. Testosterone remains the primary therapy for non-localised disease although the development of resistance is inevitable. In some cases resistance develops as a consequence of a mutation occurring in the androgen receptor conferring ligand-independent signalling. Under these circumstances down regulation of androgen receptor expression following Hsp90 inhibition represents a potential therapeutic approach.

A parallel system exists in estrogen-dependent breast cancers.

Flt3-dependent Acute Myeloid Leukaemia

Internal duplication of the tyrosine kinase receptor Flt3 leads to its constitutive activation and oncogenesis. These internal duplications are observed in 20% of all reported cases of AML and are an indication of poor prognosis Inhibition of Flt3 signalling has been shown to lead to transient reponses. Hsp90 inhibitors are predicted to be of clinical benefit to these patients as Flt3 is an Hsp90 client protein (Bali et. al., 2004 Cancer Res. 64(10):3645-52).

Melanoma Associated with Braf Mutation

Braf encodes for a serine/threonine kinase which is mutated in 70% of all melanomas. 80% of these represent a single V599E point mutation that confers elevated kinase activity to BRAF. This mutation is also transforming in NIH3T3 cells (Bignell et. al., 2002 Nature. 417(6892):949-54).

Multiple Myeloma

The Hsp90 inhibitor 17-AAG potently inhibits proliferation of Bortezomib refractory multiple myeloma cell lines. Cell surface levels of IGF-1R and IL-6R were also diminished in 17-AAG treated MM-1 cells (Mitsiades et. al., Blood 107:1092-1100, 2006). Autocrine stimulation of multiple myeloma cells, as well as paracrine stimulation of bone marrow stromal cells with IL-6 is also diminished through down-regulation of the Hsp90 client IKK.

Bortezomib (Velcade) Refractory Cancers

Compounds of the present invention may be used in the treatment of Velcade refractory tumour types including treatment of patients with multiple myeloma, mantle cell lymphoma, indolent non-Hodgkin's lymphoma, stage IIIB and IV Bronchioloalveolar carcinoma, advanced non-small cell lung cancer, breast, prostate and ovarian cancers and non-Hodgkin's lymphoma.

Gastrointestinal Stromal Tumours (GIST)

GIST tumours particularly disease dependent on growth factor activation or overexpression (e.g. c-kit).

B-CLL

ZAP-70 is an Hsp90 client protein in the circulating lymphocytes of patients with CLL but not in corresponding T cells where this kinase is normally expressed. Hence, ZAP-70 is unique among identified Hsp90 clients as its chaperone dependency is conditional on the type of cell in which it is expressed.

Other conditions or disorders for which an Hsp90 inhibitor may be of clinical benefit include, but are not limited to:

Neurodegenerative Disorders

Huntington's disease (HD) is a progressive neurodegenerative disorder with no effective treatment. GA inhibition of Hsp90 and the resulting up-regulation of Hsps are effective in preventing huntington protein aggregation in neuronal cells. (Sittler et. al., 2001, Human Molecular Genetics, Vol. 10, No. 12 1307-1315). Up-regulation of HSP may also be of clinical benefit in other diseases of protein misfolding e.g., CJD and Alzheimer's.

Inflammatory Disease, Including, but not Limited to Rheumatoid Arthritis, Asthma, Chronic Obstructive Pulmonary Disease, and Inflammatory Bowel Disease GA has been shown to dissociate HSF-1 from Hsp90 leading to the activation and nuclear translocation of HSF-1. HSF-1 subsequently acts as a transcription factor to induce HSP90 and Hsp70. The induction of Hsp70 has been implicated in the resolution of inflammation in an induced mouse model of edema (Ianaro et al., 2004 Human Molecular Genetics, 2001, Vol. 10, No. 12 1307-1315). Additionally GA treatment inhibited IkappaB kinase (IKK) activation by TNF-a or PMA. IKK is a regulator of Nf-kB and Ap-1. (Broemer et. al. 2004). Ap-1 and Nf-kB is a major transcription factor leading to the production of pro-inflammatory cytokines (Yeo et. al., 2004 *Biochem Biophys Res Commun.* 30; 320(3):816-24). The stability of pro-inflammatory cytokine transcripts is also regulated through inhibition of p38 MapK (Wax et. al., 2003. *Rheumatism Vol.* 48, No. 2, pp 541-550).

Atherosclerosis

It is known that inflammatory and immune cells play a central role in the initiation and progression of human atherosclerosis (Riganò et al., *Ann. N.Y. Acad. Sci.,* 2007, 1107:1-10) and it has been proposed that Hsp90 acts as an autoantigen in carotid atherosclerosis. Riganò et al. found specific antibodies and cells against Hsp90 in the sera of 60% of patients tested who were suffering from carotid atherosclerotic plaques but no specific antibodies or T cells targetting Hsp90 in the sera of healthy patients. Therefore, inhibitors of Hsp90 may be useful in the treatment or prevention of atherosclerosis.

Angiogenesis Related Disease, Including but not Limited to: Tumour Angiogenesis, Psoriasis, Rheumatoid Arthritis, and Diabetic Retinopathy Induction of angiogenesis is regulated by Hsp90 client proteins eNOS and Akt in endothelial cells (Sun and Liao, 2004 *Arterioscler Thromb Vasc Biol.* 24(12):2238-44). Suppression of hypoxia-inducible factor (HIF)-1a can also impair the growth, angiogenesis and vessel maturation of gastric tumours in a mouse model. (Stoeltzing et. al., 2004 *J Natl Cancer Inst;* 96:946-956.).

Type I and Type II Diabetes

Hsp90 inhibition has a profound effect on Akt signalling as well as e-nos. These are two key regulators in high glucose induced endothelial cell apoptosis in type I diabetes (Lin et. al., 2005 J Cell Biochem. 1; 94(1):194-201) and the development of hypertension in type II diabetes (Kobayashi et. al., 2004 *Hypertension.* 44(6):956-62.).

Immunosuppression and Transplantation

Hsp90 inhibition has been shown to down regulate Lck, a T-cell specific tyrosine kinase required for T-cell activation. (Yorgin et. al., 2000 *J Immunol.* 15; 164(6):2915-23.)

Cardiac Disease

Cardiac ischemic is the most common cause of death in the western world. Hsps, and notably Hsp70 (induced by radicicol treatment) have demonstrated cardioprotective activity in rat cardiomyocytes (Griffin et. al., 2004) Inhibition of Hsp90 results in the release of HSF-1 from the chaperone complex and its subsequent activation of Hsp genes. Inhibition of Hsp90 also leads to the down-regulation of HIF-1, which has been implicated in the pathogenesis of ischemic heart disease and stroke.

Infectious Disease

Hepatits C viral NS2/3 protease is an Hsp90 client protein and Hsp90 activity is required for viral processing and replication (Whitney et. al., 2001. *Proc Natl Acad Sci USA.* 20; 98(24):13931-5.).

Parasitic Disease

Geldanamycin (GA) reportedly has antimalarial activity against an Hsp90 ortholog found in *Plasmodium falciparum*. *Plasmodium* growth was inhibited with GA at an $IC_{50}$ similar to that observed with chloroquine. GA was also effective against chloroquine resistant strains of *Plasmodium falciparum* (Kumar et. al., 2003. Malar. J. 15; 2(1):30).

Inhibition, Prevention or Reversal of the Development of Drug Resistance

As discussed above, modulators or inhibitors of stress protein function in general (and Hsp90 in particular) represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

Accordingly, the invention further provides:

A method for the prophylaxis or treatment (or alleviation or reduction of the incidence) of a disease state or condition mediated by Hsp90, which method comprises administering to a subject in need thereof a compound of the invention, wherein the disease state or condition mediated by Hsp90 is the development of resistance to a cancer drug.

A method for: (i) sensitizing malignant cells to an anticancer drug; (ii) alleviating or reducing the incidence of resistance to an anticancer drug; (iii) reversing resistance to an anticancer drug; (iv) potentiating the activity of an anticancer drug; (v) delaying or preventing the onset of resistance to an anticancer drug, which method comprises administering to a subject in need thereof a compound of the invention.

A method for the treatment of a cancer which method comprises administering to a subject in need thereof a compound of the invention, which method is characterized by the absence of drug resistance.

A method for the prophylaxis or treatment (or alleviation or reduction of the incidence) of a disease state or condition mediated by Hsp90 in a subject undergoing treatment with a therapeutic agent (such as an anti-cancer agent), which method comprises administering to the subject a compound of the invention, wherein the disease state or condition mediated by Hsp90 is the development of resistance to the said therapeutic agent.

A method for: (i) sensitizing malignant cells to an anti-cancer agent; (ii) alleviating or reducing the incidence of resistance to an anti-cancer agent; (iii) reversing resistance to an anti-cancer agent; (iv) potentiating the activity of an anti-cancer agent; (v) delaying or preventing the onset of resistance to an anti-cancer agent, which method comprises administering to a subject undergoing treatment with said anti-cancer agent a compound of the invention.

A method for the treatment of a cancer in a subject undergoing treatment with an anti-cancer agent, which method comprises administering to a subject in need thereof a compound of the invention, which method is characterized by the absence of drug resistance to the anti-cancer agent.

Biological Activity

The biological activity (e.g. as inhibitors of Hsp90) of the phenolic compounds from which the pro-drug compounds of the invention are derived may be measured using the assays set forth in the examples below, for example the isothermal titration calorimetry (ITC) experiments described in Example 46 and the anti-proliferative activity assays described in Example 47. The level of activity exhibited by a given compound in the ITC assay can be defined in terms of the $K_d$ value, and preferred compounds of the present invention are compounds having a $K_d$ value of less than 1 micromolar, more preferably less than 0.1 micromolar. In the anti-proliferative activity assays, the level of activity exhibited by a given compound in an assay may be defined in terms of the $IC_{50}$ value, and preferred compounds of the present invention are compounds having an $IC_{50}$ value of less than 1 micromolar, more preferably less than 0.1 micromolar.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345(6277): 672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95.

The elimination of hERG blocking activity remains an important consideration in the development of any new drug.

It has been found that many of the phenolic compounds from which the pro-drug compounds of the invention are derived have low hERG activity and a good separation between Hsp90 inhibitory activity and hERG activity.

Preferred pro-drug compounds are the pro-drug compounds of phenolic compounds having mean $IC_{50}$ values against hERG that are greater than 30 times, or greater than 40 times, or greater than 50 times the $IC_{50}$ values of the compounds in cellular proliferation assays. Preferred pro-drugs are the pro-drugs of phenolic compounds having mean $IC_{50}$ values against hERG that are greater than 5 µM, more particularly greater than 10 µM, and more preferably greater than 15 µM. Some phenolic compounds from which the pro-drug compounds of the invention are derived have mean $IC_{50}$ values against hERG that are greater than 50 µM.

Compounds of the invention may have advantageous ADME properties and in particular better oral bioavailability than the phenolic parent compounds.

Treatment of Pain, Neuropathies, Stroke and Related Conditions

The compounds of the invention have Hsp90 inhibiting or modulating activity and hence may be useful in for use in treating, alleviating or preventing certain cdk5 mediated diseases and conditions.

Accordingly, the invention provides the use of a compound of the invention as defined herein for the manufacture of a medicament for the treatment of pain.

In another aspect, the invention provides the use of a compound of the invention as defined herein thereof for the manufacture of a medicament for the prophylaxis or treatment of stroke.

In a further aspect, the invention provides the use of a compound of the invention as defined herein for the manufacture of a medicament for use as a neuroprotective agent.

In other aspects, the invention provides:

A compound of the invention as defined herein for use in the treatment of pain.

A compound of the invention as defined herein for use in the reduction or elimination of pain in a patient (e.g. a mammal such as a human) suffering from pain.

The use of a compound of the invention as defined herein for the manufacture of a medicament for use in the reduction or elimination of pain in a patient (e.g. a mammal such as a human) suffering from pain.

The use of a compound of the invention as defined herein for the manufacture of a medicament for the treatment of any one or more of nociception, somatic pain, visceral pain, acute pain, chronic pain, hyperalgesia, allodynia, post operative pain, pain due to hypersensivity, headache, inflammatory pain (rheumatic, dental, dysmenorrhoea or infection), neurological pain, musculoskeletal pain, cancer related pain or vascular pain.

A compound of the invention as defined herein for use in treating any one or more of nociception, somatic pain, visceral pain, acute pain, chronic pain, hyperalgesia, allodynia, post operative pain, pain due to hypersensivity, headache, inflammatory pain (rheumatic, dental, dysmenorrhoea or infection), neurological pain, musculoskeletal pain, cancer related pain or vascular pain.

A method of treating pain in a patient such as a mammal (e.g. human), which method comprises administering to the patient a therapeutically effective amount of a compound of the invention as defined herein.

A method for the reduction or elimination of pain in a patient (e g a mammal such as a human) suffering from pain, which method comprises administering to the patient an effective pain-reducing or pain-eliminating amount of a compound of the invention as defined herein.

A method for the treatment of any one or more of nociception, somatic pain, visceral pain, acute pain, chronic pain, hyperalgesia, allodynia, post operative pain, pain due to hypersensivity, headache, inflammatory pain (rheumatic, dental, dysmenorrhoea or infection), neurological pain, musculoskeletal pain, cancer related pain or vascular pain, which method comprises administering to the patient a therapeutically effective amount of a compound of the invention as defined herein.

A compound of the invention as defined herein for use in the prophylaxis or treatment of stroke.

A method for the prophylaxis or treatment of stroke in a patient such as a mammal (e.g. human), which method comprises administering to the patient a therapeutically effective amount of a compound of the invention as defined herein.

A compound of the invention as defined herein for use as a neuroprotective agent.

A method of preventing or reducing neuronal damage in a patient suffering from stroke, which method comprises administering to the patient an effective neuroprotective amount of a compound of the invention as defined herein.

The use of a compound of the invention as defined herein for the manufacture of a medicament for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation.

A compound of the invention as defined herein for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation.

A method for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation, which method comprises administering to the patient an effective therapeutic amount of a compound of the invention as defined herein.

A compound of the invention as defined herein for use in the prophylaxis or treatment of a disease state or condition mediated by a cyclin dependent kinase 5.

The use of a compound of the invention as defined herein for the manufacture of a medicament for the prophylaxis or treatment of a disease state or condition mediated by a cyclin dependent kinase 5.

A method for the prophylaxis or treatment of a disease state or condition mediated by a cyclin dependent kinase 5, which method comprises administering to a subject in need thereof a compound of the invention as defined herein.

A method for alleviating or reducing the incidence of a disease state or condition mediated by a cyclin dependent kinase 5, which method comprises administering to a subject in need thereof a compound of the invention as defined herein.

The use of a compound of the invention as defined herein for the manufacture of a medicament for the prophylaxis or treatment of a disease state or condition mediated by cdk5 or p35.

The use of a compound of the invention as defined herein for the manufacture of a medicament for the prophylaxis or treatment of a disease state or condition mediated by cdk5 or p35, said disease state or condition being other than Alzheimer's disease, Huntington's disease or Creutzfeldt-Jakob disease.

The use of a compound of the invention as defined herein for the manufacture of a medicament for the prophylaxis or treatment of a disease state or condition mediated by cdk5 or p35, said disease state or condition being other than a neurodegenerative disease.

The use of a compound of the invention as defined herein for the manufacture of a medicament for the prophylaxis or treatment of a disease state or condition characterised by elevated levels of cdk5 or p35.

A compound of the invention as defined herein for use in the prophylaxis or treatment of a disease state or condition mediated by cdk5 or p35, said disease state or condition being other than Alzheimer's disease, Huntington's disease or Creutzfeldt-Jakob disease.

A compound of the invention as defined herein for use in the prophylaxis or treatment of a disease state or condition mediated by cdk5 or p35, said disease state or condition being other than a neurodegenerative disease.

A compound of the invention as defined herein for use in the prophylaxis or treatment of a disease state or condition characterised by elevated levels of cdk5 or p35.

A method of prophylaxis or treatment of a disease state or condition mediated by cdk5 or p35, said disease state or condition being other than Alzheimer's disease, Huntington's disease or Creuzfeldt-Jacob disease, which method comprises administering to a patient in need thereof a therapeutically effective amount of a compound of the invention as defined herein.

A method of prophylaxis or treatment of a disease state or condition mediated by cdk5 or p35, said disease state or condition being other than a neurodegenerative disease, which method comprises administering to a patient in need thereof a therapeutically effective amount of a compound of the invention as defined herein.

A method of prophylaxis or treatment of a disease state or condition characterised by elevated levels of cdk5 or p35, which method comprises administering to a patient in need thereof a therapeutically effective amount of a compound of the invention as defined herein.

A compound of the invention as defined herein for use in the prophylaxis or treatment of a neuropathy, such as a peripheral neuropathy, other than Alzheimer's disease, Huntington's disease or Creutzfeldt-Jakob disease.

The use of a compound of the invention as defined herein for the manufacture of a medicament for the prophylaxis or treatment of a neuropathy, such as a peripheral neuropathy, other than Alzheimer's disease, Huntington's disease or Creuzfeldt-Jacob disease.

A method of prophylaxis or treatment of a neuropathy, such as a peripheral neuropathy, other than Alzheimer's disease, Huntington's disease or Creuzfeldt-Jacob disease, which method comprises administering to a patient in need thereof a therapeutically effective amount of a compound of the invention as defined herein.

Anti-fungal, Anti-protozoal, Anti-viral and Anti-parasitic Activity

Compounds of the present invention and their acid addition salts and crystalline forms thereof may have antifungal activity, anti-protozoal activity and anti-parasitic activity.

In particular, compounds of the invention may be useful in treating infection by pathogenic fungi, protozoa and parasites where infection by the pathogen is normally associated with an antibody response to HSP90.

In one embodiment, the invention provides compounds of the invention as defined herein for use as anti-fungal agents.

Examples of fungi include those that are pathogenic in man and other animals, for example:

*Candida* species such as *Candida albicans* and *Candida tropicalis;*
*Cryptococcus* species such as *Cryptococcus neoformans* and Cryptococcal meningitis;
*Aspergillus* species such as *Aspergillus fumigatus*, *Aspergillus flavus* and *Aspergillus niger;*
*Microsporum* species such as *Microsporum canis* and *Microsporum gypseum;*
*Epidermophyton* species;
*Trichophyton* species such as *Trichophyton equinum*, *Trichophyton mentagrophytes* and *Trichophyton rubrum;*
*Epidermophyton floccosum;*
*Exophiala werneckii;*
*Fusarium* species such as *Fusarium solani;*
*Sporothrix schenckii;*
*Penicillium* species such as *Penicillium rubrum;*
*Alternaria* species;
*Ceratocystis pilifera;*
*Chrysosporium pruinosum;*
*Helminthsporium* species;
*Paecilomyces variotti;*
yeasts, for example *Saccharomyces cerevisiae* and *Pityrosporum* species such as *Pityrosporum orbiculare* and *Pityrosporum ovale;*
*Histoplasma* species such as *Histoplasma capsulatum;*
*Coccidiodes* species;
*Paracoccidioides* species; and
*Blastomyces* species.

In another embodiment, the invention provides compounds of the invention as defined herein for use as anti-protozoal agents.

Examples of protozoa include:

*Trypanosoma cruzi;*
*Leishmania* species; for example the *L. donovani* complex (*L. donovani*, *L. infantum*, and *L. chagasi*); the *L. mexicana* complex (3 main species—*L. mexicana*, *L. amazonensis*, and *L. venezuelensis*); *L. tropica; L. major; L. aethiopica*; and the subgenus *Viannia* with four main species (*L. (V.) braziliensis*, *L. (V.) guyanensis*, *L. (V.) panamensis*, and *L. (V.) peruviana*);
*Toxoplasma gondii*; and
*Trichomonas vaginalis.*

In a further embodiment, the invention provides compounds of the invention as defined herein for use as anti-parasitic agents.

Examples of parasites include parasitic worms such as:
parasitic roundworms such as *Ascaris lumbricoides;*
parasitic flatworms such as the parasitic trematode worms, e.g. *Schistosoma mansoni*

The invention also provides inter alia:

A compound of the invention as defined herein for use in the prophylaxis or treatment of a fungal, protozoal or parasitic disease state or condition (other than a disease state or condition due to *Plasmodium falciparum*), for example a disease state or condition characterised by an antibody response to Hsp90.

The use of a compound of the invention as defined herein for the manufacture of a medicament for the prophylaxis or treatment of a fungal, protozoal or parasitic disease state or condition (other than a disease state or condition due to *Plasmodium falciparum*), for example a disease state or condition characterised by an antibody response to Hsp90.

A method for the prophylaxis or treatment of a fungal, protozoal or parasitic disease state or condition (other than a disease state or condition due to *Plasmodium falciparum*), for example a disease state or condition characterised by an antibody response to Hsp90, which method comprises administering to a subject in need thereof a compound of the invention as defined herein.

A compound of the invention as defined herein for use in the prophylaxis or treatment of a fungal disease state or condition, for example a disease state or condition characterised by an antibody response to Hsp90.

The use of a compound of the invention as defined herein for the manufacture of a medicament for the prophylaxis or treatment of a fungal disease state or condition, for example a disease state or condition characterised by an antibody response to Hsp90.

A method for the prophylaxis or treatment of a fungal disease state or condition, for example a disease state or condition characterised by an antibody response to Hsp90, which method comprises administering to a subject in need thereof a compound of the invention as defined herein.

A compound of the invention as defined herein for use in preventing, arresting or reversing the infection of an animal (such as a mammal, e.g. a human) by pathogenic fungi.

The use of a compound of the invention as defined herein for the manufacture of a medicament for preventing, arresting or reversing the infection of an animal (such as a mammal, e.g. a human) by pathogenic fungi.

A method for preventing, arresting or reversing the infection of an animal (such as a mammal, e.g. a human) by pathogenic fungi, which method comprises administering to a subject in need thereof a compound of the invention as defined herein.

A compound of the invention as defined herein for any of the uses and methods set forth above, and as described elsewhere herein.

The use of a compound of the invention as defined herein for the manufacture of a medicament for the prophylaxis or treatment of any of the disease states or conditions described herein.

A combination of a compound of the invention as defined herein with an ancilliary compound which is an antifungal agent (e.g. an azole antifungal agent).

A pharmaceutical composition comprising a compound of the invention as defined herein with an ancilliary compound which is an antifungal agent (e.g. an azole antifungal agent).

A compound of the invention as defined herein for use in preventing, reducing or reversing the development of resistance to an anti-fungal agent, anti-protozoal agent or anti-parasitic agent (preferably an anti-fungal agent) co-administered therewith.

The use of a compound of the invention as defined herein for the manufacture of a medicament for coadministration with an anti-fungal agent, anti-protozoal agent or anti-parasitic agent (preferably an anti-fungal agent) to prevent, reduce or reverse the development of resistance to the anti-fungal agent, anti-protozoal agent or anti-parasitic agent.

A method of preventing or reducing development of resistance to an anti-fungal agent in a patient (e.g. a human patient), which method comprises administering to the patient a combination of an anti-fungal agent, anti-protozoal agent or anti-parasitic agent (preferably an anti-fungal agent) and a compound of the invention as defined herein.

A method for the prophylaxis or treatment (or alleviation or reduction of the incidence) of a disease state or condition mediated by Hsp90, which method comprises administering to a subject in need thereof a combination of a compound of the invention as defined herein with an anti-fungal, anti-protozoal or anti-parasitic drug, wherein the disease state or condition mediated by Hsp90 is the development of resistance to the anti-fungal, anti-protozoal or anti-parasitic drug.

A method for: (i) sensitizing fungal, protozoal or parasite cells to an anti-fungal, anti-protozoal or anti-parasitic drug; (ii) alleviating or reducing the incidence of resistance to an anti-fungal, anti-protozoal or anti-parasitic drug; (iii) reversing resistance to an anti-fungal, anti-protozoal or anti-parasitic drug; (iv) potentiating the activity of an anti-fungal, anti-protozoal or anti-parasitic drug; (v) delaying or preventing the onset of resistance to an anti-fungal, anti-protozoal or anti-parasitic drug, which method comprises administering to a subject in need thereof a combination of a compound of the invention as defined herein with the said anti-fungal, anti-protozoal or anti-parasitic drug.

A method for the treatment of a fungal, protozoal or parasitic disease or condition, which method comprises administering to a subject in need thereof a combination of compound of the invention as defined herein with an anti-fungal, anti-protozoal or anti-parasitic drug, which method is characterized by the absence of drug resistance.

A method for the prophylaxis or treatment (or alleviation or reduction of the incidence) of a disease state or condition mediated by Hsp90 in a subject undergoing treatment with an anti-fungal, anti-protozoal or anti-parasitic drug, which method comprises administering to the subject a compound of the invention as defined herein, wherein the disease state or condition mediated by Hsp90 is the development of resistance to said anti-fungal, anti-protozoal or anti-parasitic drug.

A method for: (i) sensitizing fungal, protozoal or parasite cells to an anti-fungal, anti-protozoal or anti-parasitic drug; (ii) alleviating or reducing the incidence of resistance to an anti-fungal, anti-protozoal or anti-parasitic drug (iii) reversing resistance to an anti-fungal, anti-protozoal or anti-parasitic drug; (iv) potentiating the activity of an anti-fungal, anti-protozoal or anti-parasitic drug; (v) delaying or preventing the onset of resistance to an anti-fungal, anti-protozoal or anti-parasitic drug, which method comprises administering to a subject undergoing treatment with said ancillary compound a compound of the invention as defined herein.

A method for the treatment of a fungal, protozoal or parasitic disease in a subject undergoing treatment with an anti-fungal, anti-protozoal or anti-parasitic drug, which method comprises administering to a subject in need thereof a compound of the invention as defined herein, which method is characterized by the absence of drug resistance e.g. to said anti-fungal, anti-protozoal or anti-parasitic drug).

As described above in the introductory part of this application, compounds having Hsp90 inhibitory activity have been found to exhibit potent anti-fungal activity and prevent the development of resistance to anti-fungals and in particular Hsp90 dependent resistance to anti-fungals. Moreover, it has been found that inhibition of Hsp90 activity can reduce the development of resistance to commonly used anti-fungal drugs such as the azoles. It is therefore envisaged that the compounds of the invention will be useful in the prophylaxis or treatment of a range of fungal diseases and conditions and will also be useful, when coadminstered with other anti-fungal drugs such as the azoles, in enhancing the activity of the anti-fungal drugs.

The antifungal activity of the compounds of the present invention may be evaluated by determining the minimum fungistatic (inhibition) concentration (m.i.c.). This test is usually performed by preparing a series of plates or tubes containing a suitable nutrient medium, each plate or tube also containing a different concentration of the test compound and then inoculating the medium with the fungal species. After an incubation period the plates are examined visually for the presence or absence of fungal growth. The m.i.c. is the minimum concentration required to prevent fungal growth.

The compounds may be used in animal medicine (for example in the treatment of mammals such as humans).

Fungal infections in animals against which compound of the invention as defined herein may be used include:
  Superficial mycoses—i.e. fungal infections limited to the outermost layers of the skin and hair;
  Cutaneous mycoses—i.e. fungal infections that extend deeper into the epidermis but are typically restricted to the keratinized layers of the skin, hair, and nails;
  Subcutaneous mycoses—i.e. fungal infections involving the dermis, subcutaneous tissues, muscle, and fascia;
  Systemic mycoses due to primary pathogens (these typically originate primarily in the lungs and may spread to other organ systems); and
  Systemic mycoses due to opportunistic pathogens (infections of patients with immune deficiencies who would otherwise not be infected).

Particular examples of fungal disease states for which compounds of the invention as defined herein may be used include:
  Dermatophyte infections such as *tinea* versiColour (a superficial fungal infection of the skin), *tinea pedis* (Athletes' Foot), *tinea capitis* (superficial fungal infection on the head), *tinea barbae* (fungal infection of bearded areas), *tinea corporis* (fungal infection of smooth skin areas).
  Mucosal Candidiasis such as Oral Candidiasis, esophagitis and Vaginal candidiasis.
  Invasive or deep organ candidiasis (e.g., fungemia, endocarditis, and endophthalmitis).
  Crytpococcal infections such as Cryptococcal meningitis. Histoplasmosis.
  Blastomycosis, a fungal infection of the lungs and occasionally the skin.
  Invasive Fungal Infections (for example Invasive Candidiasis and Invasive Aspergillosis) in patients with weakened immune systems, such as patients with AIDS (e.g. patients under treatment with anti-AIDS drugs), or under treatment with anti-cancer agents.
  Aspergilloses such as Allergic Bronchopulmonary Aspergillosis.
  Aspergilloma.
  Intertrigo infections (fungal infections occurring in folds of skin e.g. between the toes or fingers, in the underarm area, or in the groin area).
  Maduramycosis (fungal invasion of the tissue of the foot, also known as madura foot).
  Coccidioidomycosis.
  Mucormycosis.
  Blastomycosis
  Geotrichosis.
  Chromoblastomycosis.
  Conidiosporosis.
  Histoplasmosis.
  Rhinosporidosis.
  Nocaidiosis.
  Para-actinomycosis.
  Penicilliosis.
  Monoliasis.
  Sporotrichosis.

Fungal infections of particular interest are Candidiasis and Aspergillosis.

Compounds of the invention also have anti-protozoal activity and anti-parasitic activity. The antiprotozoal activity of the compounds of the present invention may be assessed by conventional methods, for example by determining the minimum inhibition concentration (m.i.c.) or 50% inhibition level ($IC_{50}$).

Examples of protozoal and parasitic diseases or conditions for which compounds of the invention may prove useful include:
  Chagas disease ((trypanosomiasis)—an infection caused by the parasite *Trypanosoma cruzi*.
  Ascariasis—a human disease caused by the parasitic roundworm *Ascaris lumbricoides*.
  Leishmaniasis—a disease caused by parasites of the genus *Leishmania*.
  Toxoplasmosis—a parasitic disease caused by the protozoan *Toxoplasma gondii*.
  Schistosomiasis (Bilharzia)—a disease caused by the parasite *Schistoma mansoni*.
  Trichomoniasis—a sexually transmitted disease caused by the parasitic protozoan *Trichomonas vaginalis*.

Anti-viral Activity

As discussed above in the introductory sections of this application, infection of a host cell with viral RNA/DNA results in a substantial redirection of cellular protein synthesis towards key viral proteins encoded by the viral nucleic acid, and this frequently gives rise to upregulation of heat shock proteins. It is believed that one function of the HSP induction may be to assist in the stabilization and folding of the high levels of 'foreign' protein generated in preparation for virus replication and it has been shown (Nagkagawa et al.) that HSP 90 inhibitors can block viral replication. Accordingly, the compounds of the invention may be useful in combatting viral infections, for example by blocking or inhibiting viral replication.

Therefore, in another aspect, the invention provides a compound of the invention as defined herein for use in the prophylaxis or treatment of a viral infection (or viral disease).

In further aspects, the invention provides:
  The use of a compound of the invention as defined herein for the manufacture of a medicament for the prophylaxis or treatment of a viral infection (or viral disease).
  A method for the prophylaxis or treatment of a viral infection (or viral disease), which method comprises administering to a subject in need thereof a compound of the invention as defined herein.
  A compound of the invention as defined herein for use in blocking or inhibiting viral replication in a host organism (e.g. an animal such as a mammal (e.g. human)).
  The use of a compound of the invention as defined herein for the manufacture of a medicament for use in blocking or inhibiting viral replication in a host organism (e.g. an animal such as a mammal (e.g. human)).
  A method of blocking or inhibiting viral replication in a host organism (e.g. an animal such as a mammal (e.g. human)), which method comprises administering to the host organism a compound of the invention as defined herein.

Examples of viral infections that may be treated with the compounds of the invention include infections due to any one or more of the following viruses:

- Picornaviruses such as rhinoviruses (common cold virus), Coxsackie virus (e.g. Coxsackie B virus); and foot and mouth disease virus;
- Hepatitis viruses such as hepatitis A virus (HAV), hepatitis B virus (HBV), hepatitis C virus (HCV), hepatitis D virus (HDV) and hepatitis E virus (HEV), Coronaviruses (e.g. common cold virus and Severe acute respiratory syndrome (SARS) virus)
- Adenoviruses such as Human Adenoviruses (a cause of respiratory and conjunctival infections);
- Astroviruses (a cause of flu-like symptoms);
- Flaviviruses such as the Yellow Fever virus;
- Orthomyxoviruses such as influenza viruses (e.g. influenza A, B and C viruses);
- Parainfluenza viruses;
- Respiratory syncytial virus;
- Enteroviruses such as Poliovirus (Poliomyelitis virus);
- Paramyxoviruses such as the Measles (rubeola) virus, mumps virus, respiratory syncytial virus (RSV) and canine distemper virus (CDV);
- Togaviruses such as the Rubella (German Measles) virus and Sindbis virus;
- Herpes viruses such as:
    - Herpes simplex virus (HSV), for example HSV-1 which causes fever blisters (cold sores), gingivostomatitis, herpes keratitis, eczema herpeticum and HSV encephalitis); and HSV-2 which causes genital lesions, neonatal infections, HSV meningitis, HSV proctitis;
    - Varicella zoster virus (VZV), which causes chickenpox, congenital varicella syndrome and shingles;
    - Epstein-Barr Virus (EBV), which causes infectious mononucleosis, Burkitt's lymphoma and nasopharyngeal cancer;
    - Cytomegalovirus (CMV), e.g. human cytomegalovirus (HCMV);
    - Human herpes virus 6 (HHV-6), which causes exanthum subitum or roseola infantum
    - Human herpes virus 8 (HHV-8) or Kaposi's sarcoma-associated herpes virus (KSHV), which is found in the saliva of many AIDS patients and associated with Kaposi's sarcoma;
- Papovaviridae such as polyoma virus and human papilloma virus (HPV);
- Parvoviruses;
- Poxviruses such as Variola virus (human smallpox virus);
- Rhabdoviruses such as rabies virus and vesicular stomatitis virus (VSV); and
- Retroviruses such as Human immunodefficiency virus (HIV) which is responsible for acquired immune defficiency syndrome (AIDS); and Human T-lymphotrophic virus (HTLV).

Particular viral infections against which the compounds of the invention may be used include herpes virus, pox virus, Epstein-Barr virus, Sindbis virus, adenovirus, HIV (for prevention of AIDS development in HIV-infected individuals), HPV, HCV and HCMV viruses.

The viral infection may be other than an infection with hepatitis C virus (HCV).

The activity of the compounds of the invention as agents for blocking or preventing viral replication in host organisms or host cells may be determined in accordance with standard procedures well known to the skilled person.

The compounds of the invention may be used as the sole antiviral agent or they may be used in conjunction with other anti-viral agents such as acyclovir, ganciclovir, oseltamavir (Tamiflu®) and zanamavir (Relenza®), amantidine, rimantadine, adefovir dipivoxil, interferons (e.g. interferon alfa-2b and pegylated interferon alfa-2a), lamivudine, entecavir, ribavirin, famciclovir, valcicylovir, valacyclovir, azidothymidine (AZT—-Retrovir®), atazanavir, fosamprenavir, lamivudine, lamivudine+abacavir, tenofovir disoproxil fumarate, tenofovir disoproxil fumarate+emtricitabine, tipranavir, nelfinavir, indinavir, raltegravir, ritonavir, lopinavir+ritonavir, darunavir, amprenavir, enfuvirtide, saquinavir, hydroxyurea, VGV-1 and anti-viral vaccines.

Accordingly, the invention further provides:
- A combination of a compound of the invention as defined herein with an ancilliary compound which is an antiviral agent.
- A pharmaceutical composition comprising a compound of the invention as defined herein with an ancilliary compound which is an antiviral agent.

Methods for the Preparation of Compounds of the Formulae (1), (1a), (1b), (1c), (2), (3), (4) and (5) and Sub-Groups thereof.

In this section, as in all other sections of this application unless the context indicates otherwise, references to Formulae (1), (1a), (1b), (1c), (2), (3), (4) and (5) also include all embodiments, sub-groups, subsets thereof unless the context requires otherwise.

Compounds of formulae (1), (1a), (1b), (1c), (2), (3), (4) and (5) may be prepared by the reaction of a compound of the formula (10):

$$R^1-O-\text{(aryl with OH, COOH, isopropyl, and } O-R^2) \quad (10)$$

or a reactive deriviative thereof (such as an acid chloride), with a compound of the formula (11):

$$HN-\text{(isoindoline with } (R^3)_n\text{ at positions 4,5)} \quad (11)$$

under amide forming conditions.

For example, the compound of formula (10) may be reacted with the compound of formula (11) in the presence of amide coupling reagents of the type commonly used in the formation of amide or peptide linkages. Examples of such reagents include 1,1'-carbonyldiimidazole (CDI), 1,3-dicyclohexylcarbodiimide (DCC) (Sheehan et al, *J. Amer. Chem. Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters,* 1990, 31, 205). Carbodiimide-based coupling agents may advantageously be used in combination with 1-hydroxy-7-azabenzotriazole (HOAt) (L. A. Carpino, *J. Amer. Chem. Soc.,* 1993, 115, 4397) or 1-hydroxybenzotriazole (HOBt) (Konig et al, *Chem. Ber.,* 103, 708, 2024-2034). Preferred coupling reagents include EDC (EDAC) and DCC in combination with HOAt or HOBt.

One particular coupling reagent comprises EDC in combination with HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction may be carried out at room temperature or, where the reactants are less reactive, at an appropriately elevated temperature, for example a temperature of up to 100° C., more typically up to about 80° C. The reaction may be carried out in the presence of a non-interfering base, for example a tertiary amine such as triethylamine or N,N-diisopropylethylamine.

Alternatively, the carboxylic acid (10) may first be converted to a reactive derivative such as the acid chloride and then reacted with the isoindoline compound of formula (11). The acid chloride may be prepared by by treatment of the carboxylic acid with thionyl chloride, or by reaction with oxalyl chloride in the presence of a catalytic amount of dimethyl formamide, or by reaction of a potassium salt of the acid with oxalyl chloride. The acid chloride may then be reacted with the compound of formula (11) in the presence of a non-interfering base such as triethylamine. The reaction may be carried out at around room temperature in a polar solvent such as dioxan.

Compounds of the formula (11) may be prepared by the methods described in WO 2006/109085 or methods analogous thereto.

Compounds of the formula (10) may be prepared by the hydrolysis of an ester compound of the formula (12):

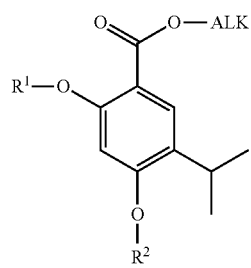

(12)

where ALK is a methyl or ethyl group and preferably methyl group. The hydrolysis of the ester (12) may be carried out using an alkali metal hydroxide such as potassium hydroxide or sodium hydroxide in aqueous solution or aqueous alcoholic (e.g. methanolic) solution. The hydrolysis is typically carried out with heating, for example to the reflux temperature of the aqueous solution.

Compounds of the formula (12) may be prepared from resorcinol derivatives of the formula (13):

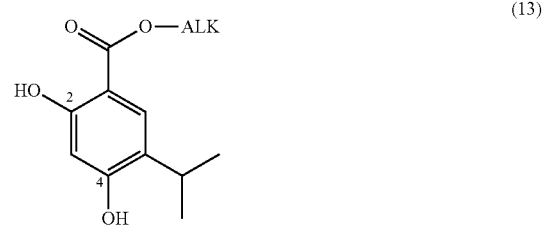

(13)

by various alkylation and acylation reactions as described in the examples in the experimental section of this application.

For example, to give compounds of the formula (12) wherein $R^1$ is hydrogen, the 4-hydroxyl group in the compound of formula (13) may be selectively protected by reaction with a compound of the formula $PG^2$-$L^1$ where $PG^2$ is a removable protecting group and $L^1$ is a leaving group such as halogen in the presence of a base to give the intermediate (14):

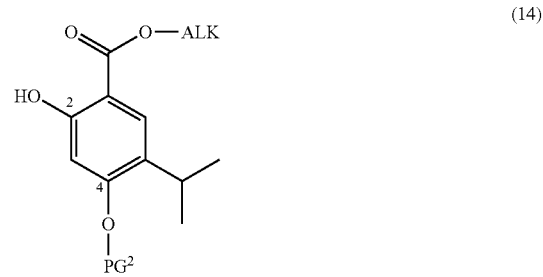

(14)

A preferred protecting group $PG^2$ is benzyl. Protection of the 4-hydroxyl group as a benzyloxy group may be accomplished by reacting the compound of formula (13) with just over one equivalent of benzyl bromide in the presence of an alkali metal carbonate base such as potassium carbonate in a polar aprotic solvent such as acetonitrile. The reaction may be carried out at room temperature. As an alternative to a benzyl protecting group, the 4-hydroxy group may be protected as a methoxymethoxy group by reaction of the compound of formula (13) with approximately one equivalent of methoxymethyl chloride in acetonitrile in the presence of potassium carbonate.

The compound of formula (14) may then be reacted with a compound of the formula $R^2$-$L^2$ where $L^2$ is a leaving group such as a halogen, or may be reacted with an alkylating agent such as dimethyl sulphate, to give a compound of formula (15):

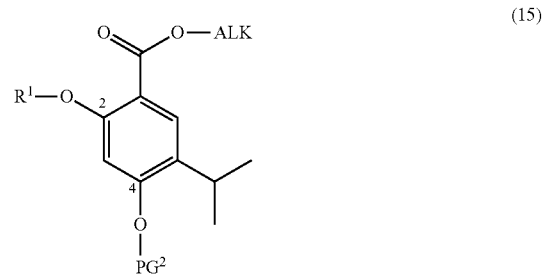

(15)

The reaction of the compound of formula (14) may be reacted with the compound of the formula $R^1-L^2$ or the alkylating agent in the presence of a base such as potassium carbonate in a polar aprotic solvent such as acetonitrile.

The protecting group $PG^2$ may then be removed (e.g. in the case of a benzyl group by hydrogenation over palladium on carbon) to give a compound of the formula (12) in which $R^2$ is hydrogen.

When $PG^2$ is a methoxymethyl group, it may either be left in place (thereby giving an intermediate compound (12) where $R^1$ and $R^2$ are different), or it may be removed by reaction with an acid such as hydrochloric acid in an aqueous alcoholic solvent such as methanol.

In order to obtain compounds of the formula (12) where $R^1$ is hydrogen, a compound of the formula (13) may be reacted with approximately one equivalent of a compound of formula $R^2-L^2$ where $L^2$ is a leaving group such as a halogen, or may be reacted with approximately one equivalent of an alkylating agent such as dimethyl sulphate. The reaction may be carried out under conditions analogous to those used described above in connection with the preparation of the compounds of formula (14).

In order to prepare compounds of the formula (12) where $R^1=R^2$ and both are other than hydrogen, a compound of the formula (13) may be reacted with approximately two equivalents of a compound of formula $R-L^2$ where $R=R^1=R^2$ and $L^2$ is a leaving group such as a halogen, or may be reacted with approximately one equivalent of an alkylating agent such as dimethyl sulphate.

The Compounds of the formula (13) may be prepared by hydrogenation of compounds of the formula (16):

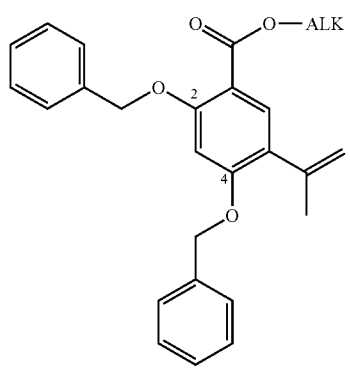

(16)

over palladium on carbon in an alcoholic solvent such as ethanol, methanol or mixtures thereof. Compounds of the formula (16) may be prepared according to the method described in WO 2006/109085, see in particular Preparation B5 on page 84 of WO 2006/109085.

The foregoing methods may be particularly suited to the preparation of compounds wherein $R^1$ and/or $R^2$ are optionally substituted alkyl or alkenyl groups.

Compounds of the formulae (1), (1a), (1b), (1c), (2), (3), (4) and (5) may also be prepared by the reaction of a compound of the formula (17):

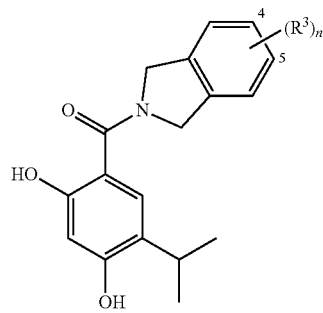

(17)

with a reagent or reagents suitable for introducing the groups $R^1$ and/or $R^2$.

For example, in order to prepare compounds of the formulae (1), (1a), (1b), (1c), (2), (3), (4) and (5) where $R^1$ and/or $R^2$ are $C(O)NR^4R^5$ where $R^4$ and $R^5$ are both $C_{1-4}$ alkyl, or $NR^4R^5$ forms a 4 to 7 membered saturated heterocyclic ring, the compound of formula (17) may be reacted with a compound of formula $Cl-C(O)NR^4R^5$ in a polar aprotic solvent such as tetrahydrofuran (THF) in the presence of a non-interfering base such as triethylamine or N,N-4-dimethylamino-pyridine. The reaction may be carried out with moderate heating (e.g. to a temperature between 50° C. and 100° C. If two or more equivalents of the compound of formula $Cl-C(O)NR^4R^5$ are used, the compound of formula (1), (1a), (1b), (1c), (2), (3), (4) or (5) in which both of $R^1$ and $R^2$ are $C(O)NR^4R^5$ is formed.

If desired, one of the two groups $C(O)NR^4R^5$ may be removed by heating with an alkali metal hydroxide such as aqueous methanolic sodium hydroxide to give a mixture of mono-hydroxy regioisomers that may be separated by preparative HPLC. The resulting mono-hydroxy compounds may then be treated with a reagent or reagents suitable for introducing a different group $R^1$ or $R^2$. For example, a compound wherein one of $R^1$ and $R^2$ is a group $C(O)NR^4R^5$ and the other is hydrogen may be reacted with a dialkyl carbonate of the formula $R^6OC(O)OR^6$ (such as di-tert-butyl-carbonate) to give a compound of the formula (1), (1a), (1b), (1c), (2), (3), (4) or (5) where one of $R^1$ and $R^2$ is $C(O)NR^4R^5$ and the other is $C(O)OR^6$ where $R^6$ is $C_{1-4}$ alkyl (e.g. ten-butyl). The reaction with the dialkyl carbonate is typically carried out in a polar aprotic solvent such as THF in the presence of a non-interfering base such as N,N-4-dimethylaminopyridine, usually with heating, for example to a temperature between 50° C. and 100° C.

Alternatively, a compound wherein one of $R^1$ and $R^2$ is a group $C(O)NR^4R^5$ and the other is hydrogen may be reacted with an alkylating agent such as dimethyl sulphate or methoxymethyl chloride to give a compound of the formula (4) or (5) where one of $R^1$ and $R^2$ is $C(O)NR^4R^5$ and the other is an optionally substituted alkyl group.

Compounds wherein both $R^1$ and $R^2$ are $C(O)OR^6$ may be prepared from compounds of the formula (17) by reaction with at least two equivalents of $R^6OC(O)OR^6$ under conditions similar or analogous to those described above.

Compounds wherein both $R^1$ and $R^2$ are $C(O)R^6$ may be prepared from compounds of the formula (17) by reaction with at least two equivalents of $Cl-C(O)R^6$ in a polar aprotic solvent such as THF in the presence of a non-interfering base such as triethylamine and/or N,N-4-dimethylaminopyridine.

The reaction is typically carried out at room temperature.

Compounds of the formula (17) may be prepared by the methods described in WO 2006/109085 (PCT/GB2006/001382), the contents of which are incorporated by reference herein, see in particular Example 36 on page 123, Example 42 on page 125, Example 50 on page 128, Example 55 on page 137, Example 61 on page 143, Example 63 on page 143 and Example 68 on page 145.

Many of the procedures described above are well known to those skilled in the art, and examples of alkylations, acylations, functional group interconversions and reagents and conditions for carrying out such conversions can be found in, for example, *Advanced Organic Chemistry*, by Jerry March, 4th edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

In some of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

Novel Intermediates

Many of the process intermediates (10, (12), (14) and (15) are novel and, as such, form a further aspect of the invention.

Accordingly, the invention also provides a novel process intermediate which is a compound of the formula (10) or formula (12) or formula (14) or formula (15) as defined herein, but excluding the compounds 2,4-dimethoxy-5-isopropylbenzoic acid methyl ester and 2,4-dimethoxy-5-isopropylbenzoic acid.

Particular novel process intermediate compounds are as set out below:

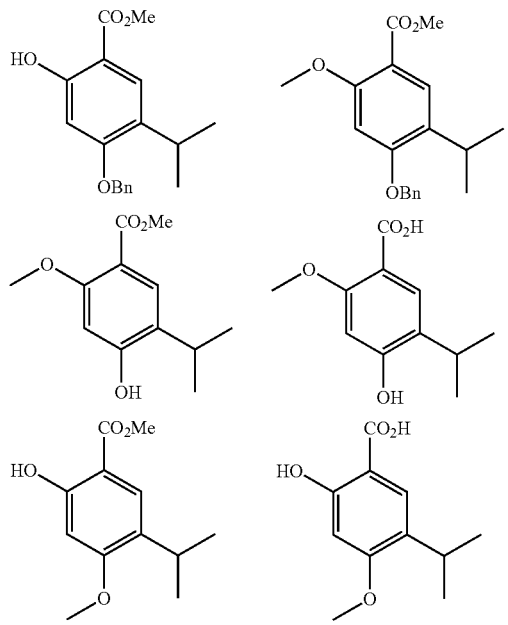

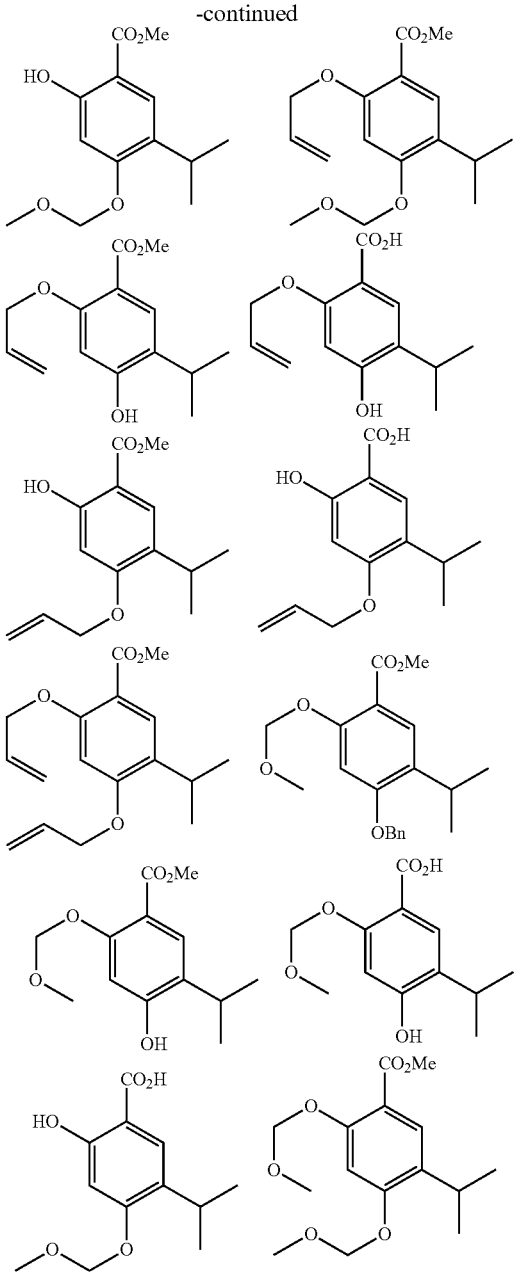

Methods of Purification

The compounds of the invention may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) may be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Alternatively, normal phase preparative LC based methods might be used in place of reverse phase methods. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above may alternatively be used to purify the compounds.

Pharmaceutical Formulations

While it is possible for the pro-drug compound to be administered alone, it is preferable to present it as a pharmaceutical composition (e.g. formulation) comprising at least one active compound of the invention together with one or more pharmaceutically acceptable excipients (for example carriers, adjuvants, diluents, fillers, buffers, stabilisers, preservatives, lubricants, or other materials well known to those skilled in the art) and optionally other therapeutic or prophylactic agents; for example agents that reduce or alleviate some of the side effects associated with chemotherapy. Particular examples of such agents include anti-emetic agents, agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF), and agents that minimize gastrointestinal toxicity.

Thus, the present invention further provides pharmaceutical compositions, as defined above, and methods of making a pharmaceutical composition comprising bringing into association (e.g. admixing) at least one active compound, as defined above, together with one or more pharmaceutically acceptable excipients such as carriers, buffers, adjuvants, stabilizers, or other materials, as described herein.

The term "excipient" as used herein refers to any component of the pharmaceutical composition other than the active compound (i.e. in the present case the prodrug compound).

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each excipient (e.g. carrier etc.) must also be "acceptable" in the sense of being compatible with the other ingredients of the formulation.

Accordingly, in a further aspect, the invention provides compounds of the invention and sub-groups thereof as defined herein in the form of pharmaceutical compositions.

The pharmaceutical compositions may be in any form suitable for oral, parenteral, topical, intranasal, ophthalmic, otic, rectal, intra-vaginal, or transdermal administration. Where the compositions are intended for parenteral administration, they may be formulated for intravenous, intramuscular, intra-peritoneal, subcutaneous administration or for direct delivery into a target organ or tissue by injection, infusion or other means of delivery. The delivery may be by bolus injection, short term infusion or longer term infusion and may be via passive delivery or through the utilisation of a suitable infusion pump.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Examples of these are described in R. G. Strickly, Solubilizing Excipients in oral and injectable formulations, Pharmaceutical Research, Vol 21(2) 2004, p 201-230. In addition, they may contain co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

A drug molecule that is ionizable may be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations may usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and may be used in combinations with each other. The resulting organic formulations are usually diluted at least 2-fold prior to IV bolus or IV infusion.

Alternatively increased water solubility may be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs may be solubilized by liposomes if the drug becomes encapsulated or intercalated within the liposome. Hydrophobic drugs may also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules, vials or pre-filled syringes, and may be stored in a freeze-dried (lyophilised) condition requiring only the addition of the sterile liquid carrier, for example water for injections, immediately prior to use.

The pharmaceutical formulation may be prepared by lyophilising a compound of Formula (I) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation may be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, may be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent may be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they may be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one embodiment of the invention, the pharmaceutical composition is in a form suitable for i.v. administration, for example by injection or infusion.

In another embodiment, the pharmaceutical composition is in a form suitable for sub-cutaneous (s.c.) administration.

In a preferred embodiment of the invention, the pharmaceutical compositions are suitable for oral administration.

Pharmaceutical dosage forms suitable for oral administration include tablets, capsules (hard or soft shell), caplets, pills, lozenges, syrups, solutions, powders, granules, elixirs and suspensions, sublingual tablets, wafers or patches (such as buccal patches).

Pharmaceutical compositions containing compounds of the invention may be formulated in accordance with known techniques, see for example, Remington's Pharmaceutical Sciences, Mack Publishing Company, Easton, Pa., USA.

Thus, tablet compositions may contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, microcrystalline cellulose (MCC), and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and may contain the active component in solid, semi-solid, or liquid form. Gelatin capsules may be formed from animal gelatin or synthetic or plant derived equivalents thereof.

The pharmaceutical compositions (e.g. tablets or capsules) may be designed to release the drug either upon contact with stomach fluids (immediate release compositions) or to release in a controlled manner (controlled release compositions) over a prolonged period of time or with a specific region of the GI tract.

The solid dosage forms (eg; tablets, capsules etc.) may be coated or un-coated, but typically have a coating, for example a protective film coating (e.g. a polymer, wax or varnish) or a release controlling coating. The coating (e.g. a Eudragit™ type polymer) may be designed to release the active component at a desired location within the gastro-intestinal tract. Thus, the coating may be selected so as to degrade under certain pH conditions within the gastrointestinal tract, thereby selectively release the compound in the stomach or in the ileum, duodenum or colon. Alternatively or additionally, the coating may be used as a taste masking agent to mask unpleasant tastes such as bitter tasting drugs. The coating may contain sugar or other agents that assist in masking unpleasant tastes.

Instead of, or in addition to, a coating, the drug may be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating may take the form of an erodible polymer (e.g. a maleic anhydride polymer) which is substantially continuously eroded as the dosage form passes through the gastrointestinal tract. As a further alternative, the active compound may be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules, and in particular in the form of tablets and capsules.

The skilled person will have the expertise to select the appropriate amounts of ingredients for use in the formulations. For example tablets and capsules typically contain 0-20% disintegrants, 0-5% lubricants, 0-5% flow aids and/or 0-100% fillers/or bulking agents (depending on drug dose). They may also contain 0-10% polymer binders, 0-5% antioxidants, 0-5% Pigments. Slow release tablets would in addition contain 0-100% polymers (depending on dose). The film coats of the tablet or capsule typically contain 0-10% polymers, 0-3% pigments, and/or 0-2% plasticizers.

Parenteral formulations typically contain 0-20% buffers, 0-50% cosolvents, and/or 0-100% Water for Injection (WFI) (depending on dose and if freeze dried). Formulations for intramuscular depots may also contain 0-100% oils.

Pharmaceutical compositions for oral administration may be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions may be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound. Thus, unit-dose suppositories or pessaries may be prepared by admixture of the active ingredient with one or more conventional solid carriers, for example coca butter, and shaping the resulting mixture. Further examples of mouldable waxy materials include polymers such as high molecular weight polyalkylene glycols, e.g. high molecular weight polyethylene glycols.

Alternatively, in the case of vaginal administration, the formulation may be presented as a tampon impregnated with the active ingredients and optionally one or more excipients or diluents. Other formulations suitable for rectal and vaginal administration include creams, gels, foams, pastes and sprays.

Further examples of topical compositions include dressings such as bandages and adhesive plasters impregnated with active ingredients and optionally one or more excipients or diluents. Carriers which may be used include e.g. polyhydric alcohols such as polyethylene glycols, propylene glycol or glycerol. Suitable excipients are those known in the art to be appropriate.

Compositions for administration by inhalation may take the form of inhalable powder compositions or liquid or powder sprays, and may be administrated in standard form using powder inhaler devices or aerosol dispensing devices. Such devices are well known. For administration by inhalation, the powdered formulations typically comprise the active compound together with an inert solid powdered diluent such as lactose.

The compounds of the invention will generally be presented in unit dosage form and, as such, will typically contain sufficient compound to provide a desired level of biological activity. For example, a formulation may contain from 1 nanogram to 2 grams of active ingredient. Within this range, particular sub-ranges of compound are 1 microgram to 2 grams, or 1 microgram to 1 gram, or 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the invention and sub-groups as defined herein will be useful in the prophylaxis or treatment of a range of disease states or conditions mediated by Hsp90 client proteins. Examples of such disease states and conditions are set out above.

An advantage of the prodrug compounds of the present invention is that they are orally administrable. Preferred prodrug compounds of the present invention provide enhanced bioavailability (compared to the parent active compound) when administered by the oral route.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides persistent intermittent dosing (e.g. a pulsatile manner).

A typical daily dose of the compound of formula (I) may be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound may be administered on a daily basis or on a repeat basis every 2, or 3, or 4, or 5, or 6, or 7, or 10 or 14, or 21, or 28 days for example.

In one particular dosing schedule, a patient will be given an infusion of a compound for periods of one hour to 4 hours daily for up to ten days in particular up to two days for one week, every two weeks in three, and the treatment repeated at a desired interval such as three to six weeks, in particular every three weeks.

More particularly, a patient may be given an infusion of a compound for periods of one hour daily twice a week for two weeks in three weeks and the treatment repeated every three weeks.

Alternatively, a patient may be given an infusion of a compound for periods of one hour daily twice a week for three weeks in four weeks and the treatment repeated every four weeks.

In another particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein may be administered as the sole therapeutic agent or they may be administered in combination therapy with one of more other compounds for treatment of a particular disease state, for example a neoplastic disease such as a cancer as hereinbefore defined.

Examples of other therapeutic agents or treatments that may be administered together (whether concurrently or at different time intervals) with the compounds of the invention include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies, e.g. HDAC or HAT modulators
Radiotherapy; and Other therapeutic or prophylactic agents; for example agents that reduce or alleviate some of the side effects associated with chemotherapy. Particular examples of such agents include anti-emetic agents, agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF), and agents that minimize accompanying gastrointestinal toxicity. Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid itself and agents such as megestrol acetate.

Other therapeutic agents that may be administered in combination with the prodrug compounds of the present invention include the therapeutic agents described in PCT/GB2007/003864 (publication number WO/2008/044029), the disclosure in which is incoprated herein by reference.

Preferably, other therapeutic agents for use in the combinations of the invention are selected from the following classes:

1. hormones, hormone agonists, hormone antagonists and hormone modulating agents (including, but not limited to corticosteroids, antiandrogens, antiestrogens and GNRAs);
2. cytokines and cytokine activating agents;
3. retinoids and rexinoids
4. monoclonal antibodies (including monoclonal antibodies to cell surface antigen(s));
5. camptothecin compounds and other topoisomerase I inhibitors;
6. antimetabolites;
7. vinca alkaloids and other tubulin targeting agents;
8. taxanes;
9. epothilones;
10. platinum compounds;
11. DNA binders and Topo II inhibitors (including anthracycline derivatives);
12. alkylating agents (including aziridine, nitrogen mustard and nitrosourea alkylating agents);
13. CDK inhibitors;
14. COX-2 inhibitors;
15. HDAC inhibitors;
16. Selective immunoresponse modulators;
17. DNA methyl transferase inhibitors;
18. proteasome inhibitors;
19. Aurora inhibitors;
20. Hsp90 inhibitors (including ancillary Hsp90 inhibitors);
21. Checkpoint targeting agents;
22. DNA repair inhibitors;
23. Inhibitors of G-protein coupled receptor inhibitors
24. Signalling inhibitors
25. Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate.

In this application, the "other therapeutic agents" (1) to (24) which may be used in combination with the prodrug compounds of the invention may be referred to for convenience as "ancillary compounds".

The definitions, biological activities, preferences, specific embodiments and posologies for each of the types of therapeutic agent (ancillary compound) (1) to (24) above are as defined in our earlier International patent application PCT/GB2007/003864 (publication number WO/2008/044029), the disclosure in which is incorporated herein by reference.

In embodiments of the invention where a combination comprises one or more other ancillary compounds, the said ancillary compounds are preferably independently selected from the classes (1) (in particular corticosteroids), (4), (6), (7), (8), (10), (11), (12), (16), (17), (18), (22) and (23). Preferably, the ancillary compound(s) is independently selected from the classes (1) to (24) (for example classes (1) to (23)) set out above. Most preferably, the one or more other ancillary compounds are independently selected from classes (1) in particular corticosteroids, (4), (6), (8), (10), (11), (12), (17), (18), and (23).

In embodiments of the invention where a combination comprises two or more ancillary compounds, then the two or more ancillary compounds are preferably independently selected from the classes (1) to (24) (for example classes (1) to (23)) set out above.

Further embodiments of the invention where combination comprise two or more ancillary compounds (in addition to the prodrug compounds of the invention) include:
  a combination of lenolidamide and thalidomide;
  a combination of two or more of the foregoing classes independently selected from (1), preferably corticosteroids, (12) and (16), preferably lenolidamide or thalidomide;
  a combination of two or more of the foregoing classes independently selected from (1), preferably corticosteroids, (7) and (11);
  a combination of two of the foregoing classes (1), preferably corticosteroids and (18);
  a combination of two of the foregoing classes (17) and (22);
  a combination of two of the foregoing classes (10) and (22);
  a combination of two or more of the foregoing classes independently selected from (1), preferably corticosteroids, (4), (6), (7), (8), (10), (11), (12), (16), (17), (18), (22) and/or (23);
  a combination of two or more of the foregoing classes independently selected from (1), preferably corticosteroids, (4), (6), (8), (10), (11), (12), (17), (18) and/or (23); and
  a combination of two or more of the foregoing classes independently selected from (1), preferably corticosteroids, (11), (12), (16) and/or (18);

Combinations of a prodrug compound of the invention with platinum agents, taxol, taxotere, gemcitabine, pemetrexed, mitomycin, ifosfamide, vinorelbine, erlotinib and bevacizumab or combinations of a compound of formula (I) with carboplatin and taxol or cisplatin and gemcitabine are particularly suitable for treating Non-Small cell lung cancer.

Combinations of a prodrug compound of the invention with 5-FU, leucovorin and CPT 11 or a combination of a compound of formula (I) with 5-FU, leucovorin and oxaliplatin, each with bevacizumab are particularly suitable for treating colon cancer.

Particularly suitable for treating breast cancer are combinations of a prodrug compound of the invention with (a) monoclonal antibodies (e.g. trastuzumab and bevicizumab); (b) monoclonal antibodies (e.g. trastuzumab and bevicizamab) and taxanes; and (c) antimetabolites (e.g. capecitabine) and signalling inhibitors (e.g. lapatinib).

Further combinations suitable for treating breast cancer are combinations of a prodrug compound of the invention with 5-FU, doxorubicin and cyclophosphamide, or combinations of a prodrug of the invention with doxorubicin and cyclophosphamide, are particularly.

A particular combination for use in treating HER2 breast cancer comprises a prodrug compound of the invention and lapatinib.

Combinations of a prodrug compound of the invention with cyclophosphamide, doxorubicin (hydroxydaunorubicin), vincristine, rituximab and prednisone are particularly suitable for treating non Hodgkin's lymphoma (and in particular high grade non Hodgkin's lymphoma).

Combinations of a prodrug compound of the invention with cyclophosphamide, vincristine, rituximab and prednisone are particularly suitable for treating non Hodgkin's lymphoma (and in particular low grade non Hodgkin's lymphoma).

Particularly suitable for treating multiple myeloma are combinations of a prodrug compound of the invention with (a) monoclonal antibodies (e.g. those targeting Interleukin 6); (b) proteasome inhibitors (e.g. bortezomib); (c) proteasome inhibitors and corticosteroids (e.g. velcade and dexamethasone); and (d) corticosteroids, alkylating agents and lenolidamide/thalidomide (e.g. prednisolone, melphalan and thalidomide).

Specific combinations suitable for treating multiple myeloma are combinations of a prodrug compound of the invention with vincristine, doxorubicin, thalidomide and dexamethasone.

Combinations of a prodrug compound of the invention with fludarabine and rituxamab are particularly suitable for treating chronic lymphocytic leukemia.

Particularly suitable for treating melanoma are combinations of a prodrug compound of the invention with (a) DNA methylase inhibitors/hypomethylating agents (e.g. temozolamide); (b) alkylating agents (e.g. dacarbazine or fotemustine); and (c) DNA methylase inhibitors/hypomethylating agents (e.g. temozolamide) and DNA repair inhibitors/PARP inhibitors.

Particularly suitable for treating gastrointestinal stromal tumors (GIST) are combinations of the prodrug compounds of the invention with an ancillary agent selected from imatinib, nilotinib, dasatinib and sunitinib.

Particularly suitable for treating prostate cancer are combinations of a prodrug compound of the invention with hormones and G-protein coupled receptor inhibitors.

Particularly suitable for treating Non Small Cell Lung Cancer (NSCLC) are combinations of a prodrug compound of the invention with (a) platinum compounds and taxanes; (b) platinum compounds and antimetabolites; (c) gefitinib and/or cetuximab.

One particular combination for use in treating NSCLC comprises a prodrug of the invention and gefitinib and/or cetuximab.

For cancer (and in particular acute myeloid leukemia) treatment, two or more anti-cancer agents independently selected from two or more of anthracycline, Ara C (a.k.a. Cytarabine), 6-mercaptopurine, thiopurine, methotrexate, mitoxantrone, daunorubicin, idarubicin, gemtuzumab ozogamicin and granulocyte colony stimulating factors may be used in combination with the prodrug compounds of the invention. Alternatively, the two or more anti-cancer agents may be independently selected from two or more of anthracycline, Ara C (a.k.a. Cytarabine), daunorubicin, idarubicin, gemtuzumab ozogamicin and granulocyte colony stimulating factors.

For cancer (and in particular breast cancer) treatment, two or more anti-cancer agents independently selected from bevacizumab, taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide may be used in combination with the prodrug compounds of the invention. Preferably, for cancer (and in particular breast cancer) treatment, the two or more anti-cancer agents may also be independently selected from taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide.

For cancer (and in particular chronic lymphocytic leukemia (CLL)) treatment, two or more anti-cancer agents independently selected from alemtuzumab, chlorambucil, cyclophosphamide, almentuzumab, vincristine, predinisolone, fludarabine, mitoxantrone and rituximab/rituxamab, particularly fludarabine and rituxamab may be used in combination with the prodrug compounds of the invention. Preferably, for cancer (and in particular chronic lymphocytic leukemia (CLL)) treatment, the two or more anti-cancer agents are independently selected from chlorambucil, cyclophosphamide, vincristine, predinisolone, fludarabine, mitoxantrone and rituximab/rituxamab, particularly fludarabine and rituxamab.

For cancer (and in particular chronic myeloid leukemia (CML)) treatment, two or more anti-cancer agents independently selected from hydroxyurea, cytarabine, desatinib, nilotinib and imatinib may be used in combination with the prodrug compounds of the invention.

For cancer (and in particular colon cancer treatment), two or more anti-cancer agents independently selected from cetuximab, 5-Fluorouracil, pantumab, leucovorin, irinotecan, oxaliplatin, raltirexed, capecitabine, bevacizumab, oxaliplatin, CPT 11, particularly 5-Fluorouracil, Leucovorin and CPT 11 or Fluorouracil, Leucovorin and Oxaliplatin may be used in combination with the prodrug compounds of the invention.

Alternatively, for cancer (and in particular colon cancer treatment), two or more anti-cancer agents independently selected from 5-Fluorouracil, leucovorin, irinotecan, oxaliplatin, raltirexed, capecitabine, bevacizumab, oxaliplatin, CPT 11 and particularly 5-Fluorouracil, Leucovorin and CPT 11 or Fluorouracil, Leucovorin and Oxaliplatin may be used in combination with the prodrug compounds of the invention.

For cancer (and in particular multiple myeloma treatment), two or more anti-cancer agents independently selected from vincristine, doxorubicin, dexamethasone, melphalan, prednisone, cyclophosphamide, etoposide, pamidronate, thalidomide, zoledronate and bortezomib, particularly vincristine, doxorubicin and dexamethasone may be used in combination with the prodrug compounds of the invention.

For cancer (and in particular Non-Hodgkin's lymphoma treatment), two or more anti-cancer agents independently selected from cyclophosphamide, doxorubicin/hydroxydaunorubicin, vincristine/Onco-TCS (V/O), prednisolone, methotrexate, cytarabine, bleomycin, etoposide, rituximab/rituxamab, fludarabine, cisplatin, and ifosphamide, particularly cyclophosphamide, doxorubicin (hydroxydaunorubicin), vincristine and prednisone for high grade NHL or cyclophosphamide, vincristine and prednisone for low grade NHL may be used in combination with the prodrug compounds of the invention.

For cancer (and in particular Non Small Cell Lung Cancer (NSCLC)) treatment, two or more anti-cancer agents may be independently selected from bevacizumab, gefitinib, erlotinib, cisplatin, carboplatin, mitomycin, vinblastine, paclitaxel, docetaxel, gemcitabine and vinorelbine, especially taxol and carboplatin or gemcitabine and cisplatin may be used in combination with the prodrug compounds of the invention.

For cancer (and in particular ovarian cancer) treatment, two or more anti-cancer agents independently selected from platinum compounds (for example Cisplatin, Carboplatin), doxorubicin, liposomal doxorubicin, paclitaxel, docetaxel, gemcitabine, melphalan and mitoxantrone may be used in combination with the prodrug compounds of the invention.

For cancer (and in in particular prostate cancer) treatment, two or more anti-cancer agents independently selected from mitoxantrone, prednisone, buserelin, goserelin, bicalutamide, nilutamide, flutamide, cyproterone acetate, megestrol/megestrel, diethylstilboestrol, docetaxel, paclitaxel, zoledronic acid, prednisolone and taxotere may be used in combination with the prodrug compounds of the invention.

In a particularly preferred embodiment, the prodrug compound of the invention is administered in combination with one or more ancillary agents selected from cisplatin, bortezomib, erlotinib, paclitaxel, trastuzumab and cytarabine.

For the case of Hsp90 inhibitors combined with other therapies, the two or more treatments may be given in individually varying dose schedules and via different routes.

Where the compound is administered in combination therapy with one, two, three, four or more other therapeutic agents (preferably one or two, more preferably one), the compounds may be administered simultaneously or sequentially. When administered sequentially, they may be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound and one, two, three, four or more other therapeutic agents may be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

In further aspects of the invention, there are provided:
- a combination (for example for use in treating non-small cell lung cancer) comprising (2,4-dihydroxy-5-isopropyl-phenyl)-[5-(4-methyl-piperazin-1-ylmethyl)-1,3-dihydro-isoindol-2-yl]-methanone or a pharmaceutically acceptable salt thereof (e.g. L-lactate) and gefitinib and/or cetuximab;
- a combination (for example for use in treating gastrointestinal stromal tumors (GIST)) comprising (2,4-dihydroxy-5-isopropyl-phenyl)-[5-(4-methyl-piperazin-1-ylmethyl)-1,3-dihydro-isoindol-2-yl]-methanone or a pharmaceutically acceptable salt thereof (e.g. L-lactate) and an ancillary agent selected from imatinib, nilotinib, dasatinib and sunitinib;
- a combination (for example for use in treating HER2 breast cancer) comprising (2,4-dihydroxy-5-isopropyl-phenyl)-[5-(4-methyl-piperazin-1-ylmethyl)-1,3-dihydro-isoindol-2-yl]-methanone or a pharmaceutically acceptable salt thereof (e.g. L-lactate) and lapatinib; and
- a combination (for example for use in treating acute myeloid leukaemia) comprising (2,4-dihydroxy-5-isopropyl-phenyl)-[5-(4-methyl-piperazin-1-ylmethyl)-1,3-dihydro-isoindol-2-yl]-methanone or a pharmaceutically acceptable salt thereof (e.g. L-lactate) and an ancillary agent selected from daunorubicin and idarubicin.

Dosing regimes, formulations and administration protocols for the above combinations comprising (2,4-dihydroxy-5-isopropyl-phenyl)-[5-(4-methyl-piperazin-1-ylmethyl)-1,3-dihydro-isoindol-2-yl]-methanone or a pharmaceutically acceptable salt thereof (e.g. L-lactate) may be as set out above in relation to the dosing regimes, formulations and administration protocols for the prodrug compounds or as set out in WO2008/044027, the contents of which are incorporated herein by reference in their entirely.

The compound (2,4-dihydroxy-5-isopropyl-phenyl)-[5-(4-methyl-piperazin-1-ylmethyl)-1,3-dihydro-isoindol-2-yl]-methanone can be prepared as described in WO2006/109085 and the L-lactate and other salts can be prepared as described in WO2008/044034. The contents of WO2006/109085 and WO2008/044034 are incorporated herein by reference in their entirely.

Methods of Diagnosis

Prior to administration of a compound, a patient may be screened to determine whether a disease or condition from which the patient is or may be suffering is one which would be susceptible to treatment with a compound having activity against Hsp90.

For example, a biological sample taken from a patient may be analysed to determine whether a condition or disease, such as cancer, that the patient is or may be suffering from is one which is characterised by a genetic abnormality or abnormal protein expression which leads to the mutation or over-activation of an Hsp90 client protein. Examples of such abnormalities that result in activation of Hsp90 client proteins include; Bcr-ABL translocation, Flt-3 internal duplication, and mutation of Braf or ErbB2.

Thus, the patient may be subjected to a diagnostic test to detect a marker characteristic of up-regulation. The term diagnosis includes screening. By marker we include genetic markers including, for example, the measurement of DNA composition to identify mutations of Braf, BCR-abl, and Flt3 or other affected client proteins. The term marker also includes proteins such as ErbB2, including levels or concentrations of the protein or some fragments or degradation product and for enzymes the enzymic activity. The protein (e.g. phosphorylated or not) and mRNA levels of the aforementioned proteins could also be assessed to characterise a change in activity. For example the level of phosphorylated AKT may be an indicator of sensitivity to HSP90 inhibitors The diagnostic tests are typically conducted on a biological sample selected from for example tumour biopsy samples, blood samples (isolation and enrichment of shed tumour cells), stool biopsies, sputum, chromosome analysis, pleural fluid, peritoneal fluid, buccal spears or biopsy or from urine.

The screening process will typically involve direct sequencing, oligonucleotide or protein microarray analysis, proteomic analysis by mass spectrometry, immunohistochemical techniques or detection using a specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR), in-situ hybridisation or immunoblotting.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce non-specific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Commercially available FISH probes also exist for cytogenetic detection of chromosome rearrangements, which may be used to detect Bcr-Abl fusion products within leukaemia cell populations. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al., BMC Cancer 2003, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of the "philadelphia chromosome" indicative of bcr-ABL translocation.

Therefore, all of these techniques could also be used to identify tumours particularly suitable for treatment with the compounds of the invention.

The invention will now be further described by way of the following non-limiting examples.

EXAMPLES

The invention will now be illustrated, but not limited, by reference to the specific embodiments described in the following examples.

In the examples, the following abbreviations may be used.
AcOH acetic acid
BOC tert-butyloxy carbonyl
Bn benzyl
CDI 1,1-carbonyldiimidazole
DMAW90 Solvent mixture: DCM: MeOH, AcOH, H$_2$O (90: 18:3:2)
DMAW120 Solvent mixture: DCM: MeOH, AcOH, H$_2$O (120:18:3:2)
DMAW240 Solvent mixture: DCM: MeOH, AcOH, H$_2$O (240:20:3:2)
DCM dichloromethane
DMF dimethylformamide
DMSO dimethyl sulphoxide
EDC 1-ethyl-3-(3'-dimethylaminopropyl)-carbodiimide
Et$_3$N triethylamine
EtOAc ethyl acetate
Et$_2$O diethyl ether
h hour(s)
HOAt 1-hydroxyazabenzotriazole
HOBt 1-hydroxybenzotriazole
MeCN acetonitrile
MeOH methanol
min minutes
P.E. petroleum ether
r.t. room temperature
SiO$_2$ silica
TBTU N,N,N',N'-tetramethyl-O-(benzotriazol-1-yl)uronium tetrafluoroborate
THF tetrahydrofuran Proton magnetic resonance ($^1$H NMR) spectra were recorded on a Bruker AV400 instrument operating at 400.13 MHz, in DMSO-d$_6$ or MeOH-d$_4$ (as indicated) at 27° C., unless otherwise stated and are reported as follows: chemical shift δ/ppm (number of protons, multiplicity where s=singlet, d=doublet, t=triplet, q=quartet, m=multiplet, br=broad). The residual protic solvent was used as the internal reference.

In the examples, the compounds prepared were characterised by liquid chromatography and mass spectroscopy using the Agilent LC-MS preparative system and operating conditions set out below. Where atoms with different isotopes are present and a single mass quoted, the mass quoted for the compound is the monoisotopic mass (i.e. $^{35}$Cl; $^{79}$Br etc.).
Agilent 1100 LC-MS Preparative System:
Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter
Software:
Chemstation: Chem32
Agilent MS Running Conditions:
Capillary voltage: 4000 V (3500 V on ES Negative)
Fragmentor/Gain:150/1
Drying gas flow: 13.0 L/min
Gas Temperature: 350° C.
Nebuliser Pressure: 50 psig
Scan Range: 125-800 amu
Ionisation Mode ElectroSpray Positive or ElectroSpray Negative
Acid Method:
Phenomenex Synergy MAX-RP, 10μ, 100×21.2 mm
Solvent A: H$_2$0+0.1% trifluoroacetic acid,
Solvent B: CH$_3$CN 30 0.1% trifluoroacetic acid
Basic Method:
Waters XBridge C18 5μ 100×19 mm
Solvent A: H$_2$0+10 mM NH$_4$HCO$_3$+NH4OH, pH=9.2
Solvent B: CH$_3$CN
Make Up Solvent:
MeOH+0.2% Formic Acid (for both chromatography type)
Methods:
In order to determine the optimum conditions for preparative HPLC, analytical LC-MS was initially carried out using the type of chromatography (low or high pH) most suited for the particular compound structure. Once a set of conditions were identified that gave chromatography, a suitable preparative method of the same type was chosen. Typical running condition for both low and high pH chromatography methods were:
Flow: 
Flow rate: 24 ml/min
Gradient: Generally all gradients had an initial 0.4 min step with 95% A+5% B. Then according to analytical trace a 3 6 min gradient was chosen in order to achieve good separation (e.g. from 5% to 50% B for early retaining compounds; from 35% to 80% B for middle retaining compounds and so on)

Wash: A 1.2 minute wash step was performed at the end of the gradient

Re-equilibration: 2.1 minutes re-equilibration step was ran to prepare the system for the next run Make Up flow rate: 1 ml/min Solvent:
All compounds were usually dissolved in 100% MeOH or 100% DMSO From the information provided someone skilled in the art could purify the compounds described herein by preparative LC-MS.

Preparation of Intermediates

Preparation A1

5-(4-Methylpiperazin-1-ylmethyl)-2,3-dihydro-1H-isoindole trihydrochloride

Step 1: Di-prop-2-ynyl-carbamic acid benzyl ester

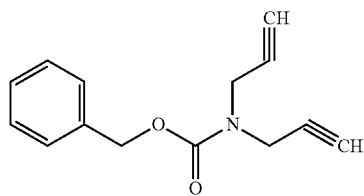 [SMILES: C#CCN(CC#C)C(=O)OCc1ccccc1]

To a cooled (0° C.) solution of dipropargylamine (46.7 g, 502 mmol) in EtOAc (200 mL) and 10% aqueous $K_2CO_3$ (700 mL, 507 mmol) was slowly added a solution of N-(benzyloxycarbonyloxy)succinimide (125 g, 502 mmol) in EtOAc (500 mL) over 20 mins. The solution was stirred at 0° C. for 2 h then at RT 16 h. The phases were separated and the organic phase was washed with 10% aqueous $K_2CO_3$ (700 mL, 507 mmol) and then with saturated brine (500 mL) and was diluted to 1000 mL with EtOAc to give a 0.5M solution.

Step 2: 5-Hydroxymethyl-1,3-dihydro-isoindole-2-carboxylic acid benzyl ester

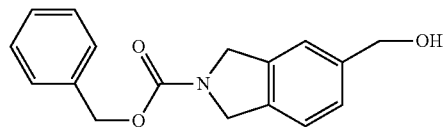 [SMILES: O=C(OCc1ccccc1)N1Cc2ccc(CO)cc2C1]

A solution of propargyl alcohol (26.4 mL, 424 mmol) in toluene (120 mL) was degassed. The 0.5M-diyne solution above (440 mL, 220 mmol) was evaporated and the residue dissolved in toluene (80 mL). This protected diyne solution and Wilkinson's catalyst (2.26 g, 2.44 mmol, 1.11% were added in 14 equal portions over a 2 h period with constant monitoring of the internal temperature such that the temperature remained 50-100° C. The solution was allowed to cool to 50° C. over 30 min when the solution was evaporated (to remove excess propargyl alcohol). The residue was heated with toluene (500 mL) and charcoal (Darco 4-12 mesh, 20 g) at 100° C. for 30 min and then filtered hot through a bed of Celite and the brown solution was evaporated. The residue was dissolve in EtOAc (400 mL) at 80° C. when silica gel (chromatography grade 65 g) was added and heating continued for 20 mins. The solution was filtered whilst hot and then evaporated (with seeding) to give a pale brown solid. 10% EtOAc/heptane (v/v, 100 mL) was added and the solid removed by filtration. The solid was washed on the sinter with heptane (100 mL) and the dried (50° C., oil pump, 16 h) to give the title compound 59.0 g (95%). $^1$H NMR (400 MHz, Me-d3-OD): 7.51-7.16 (m, 8H), 5.21 (s, 2H), 4.74 (s, 2H), 4.70 (s, 2H), 4.61 (s, 2H).

Step 3: 5-Methanesulfonyloxymethyl-1,3-dihydro-isoindole-2-carboxylic acid benzyl ester

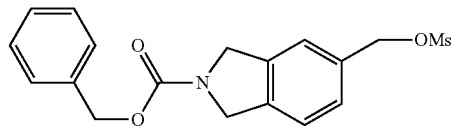 [SMILES: CS(=O)(=O)OCc1ccc2c(c1)CN(C(=O)OCc1ccccc1)C2]

To a solution of 5-hydroxymethyl-1,3-dihydro-isoindole-2-carboxylic acid benzyl ester (65.75 g, 0.232 mol) in THF (470 mL) and EtOAc (770 mL) was added $Et_3N$ (39 mL, 0.28 mol). The solution was cooled in an ice-bath and a solution of methanesulphonyl chloride (19 mL, 0.245 mol) dissolved in EtOAc (50 mL) was added (so that the internal temp<12° C.). After stiffing for 2 h in the ice-bath further additions of methanesulphonyl chloride (1.9 mL and 0.95 mL) and $Et_3N$ (3.9 mL) were made (so that by tlc there was no remaining starting material after a further 1 h of stiffing). $NaHCO_3$ (550 mL) was added and the solution stirred for 20 mins then saturated brine (200 mL) was added and the phases were separated. The organic phase was dried ($MgSO_4$) and evaporated with seeding to give a damp solid which was used in the next step without thorough drying.

Step 4: 5-(4-Methyl-piperazin-1-ylmethyl)-1,3-dihydro-isoindole-2-carboxylic acid benzyl ester dihydrochloride salt

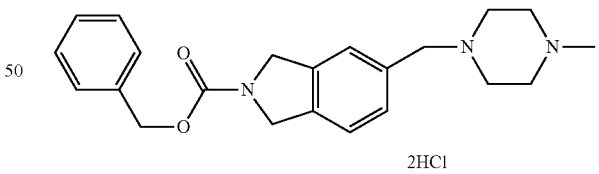

The solid from Step 3 (assume 0.232 mol) was dissolved in acetone (700 mL) and this solution was added over 45 mins to a cooled (internal temp 15-17° C.) suspension of $K_2CO_3$ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine (150 mL) and finally washed with saturated brine (300 mL). The solution was dried ($MgSO_4$) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. $^1$H NMR (400 MHz, Me-d3-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Alternative Step 4A—5-(4-Methyl-piperazin-1-ylmethyl)-1,3-dihydro-isoindole-2-carboxylic acid benzyl ester dihydrochloride

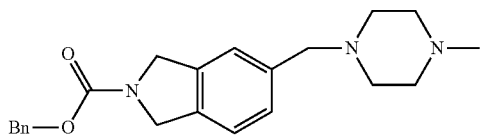 [SMILES: CN1CCN(Cc2ccc3c(c2)CN(C(=O)OCc2ccccc2)C3)CC1]

Step 4A may be used as an alternative route to replace steps 3 and 4 above.

To a suspension of manganese dioxide (15.5 g, 178 mmol) in DCM (100 mL) was added 5-hydroxymethyl-1,3-dihydro-isoindole-2-carboxylic acid benzyl ester (3.35 g, 11.8 mmol) and after 6 h stirring at RT a further addition of manganese dioxide (5 g, 57 mmol) was made. After a further 1 h stirring at RT Celite (7 g) was added and the solution was filtered through a bed of Celite™ giving a clear pale yellow solution. The Celite™ was washed with DCM and the volume of the combined organic solution adjusted to 100 mL by evaporation. N-Methylpiperazine (1.31 mL, 11.8 mmol) and acetic acid (0.68 mL) were added followed by sodium triacetoxyborohydride (4.98 g, 23.5 mmol). The yellow solution was stirred 16 h giving a colourless solution. To the solution was added 2M-HCl (10 mL, 20 mmol) giving an effervescence. After 30 min water (10 mL) and K$_2$CO$_3$ (5.5 g, 39.8 mmol) were added and the organic phase was dried (Na$_2$SO$_4$). After filtration 4M-HCl in dioxan (6 mL) was added with stirring and the suspension was evaporated to dryness. The residue was dissolved in MeOH with warming and after evaporation the solid was washed on a sinter with EtOAc then petrol (bp 40-60° C.) followed by drying in vacuo at 50° C. to give the title compound 3.61 g (70%). $^1$H NMR (400 MHz, Me-d3-OD): 7.65-7.51 (2H, m), 7.51-7.27 (6H, m), 5.23 (2H, s), 4.83-4.69 (4H, m), 4.49 (2H, s), 3.66 (8H, d), 3.03 (3H, s)

Step 5: 5-(4-Methylpiperazin-1-ylmethyl)-2,3-dihydro-1H-isoindole trihydrochloride

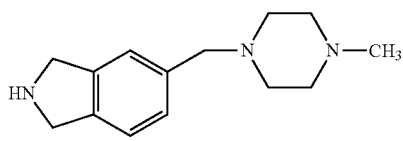 [SMILES: CN1CCN(Cc2ccc3c(c2)CNC3)CC1]

10% Palladium on carbon (300 mg) was added to a suspension of benzyl 5-(4-methylpiperazin-1-ylmethyl)-1,3-dihydro-isoindole-2-carboxylate (3.65 g, 10.0 mmol) in methanol (50 ml) and the mixture was stirred at room temperature under a hydrogen atmosphere for 5 hours. The catalyst was removed by filtration, rinsed with methanol (2×5 ml) and the combined filtrates were treated with a saturated solution of hydrogen chloride gas in ethyl acetate (20 ml). The mixture was stirred at room temperature for 30 minutes and the volatile material and solvent were removed in vacuo to afford 5-(4-methylpiperazin-1-ylmethyl)-2,3-dihydro-1H-isoindole trihydrochloride (3.39 g, 99%) as an off-white solid. $^1$H NMR (MeOH-d$_4$) 7.73 (1H, s), 7.68 (1H, d), 7.57 (1H, d), 4.72 (2H, s), 4.70 (2H, s), 4.52 (2H, s), 3.70 (8H, br s), 3.02 (3H, s). MS: [M+H]$^+$ 232.

Preparation A2

Methyl 2,4-dihydroxy-5-isopropylbenzoate

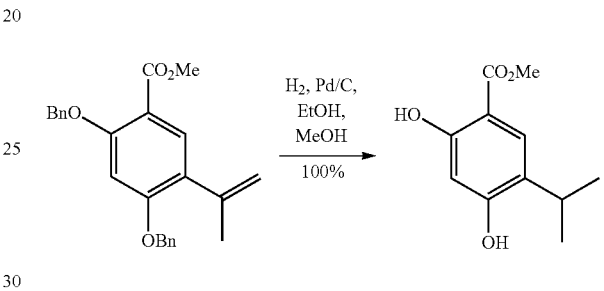

10% Palladium on carbon (350 mg) was added to a suspension of methyl 2,4-bis-benzyloxy-5-isopropenylbenzoate [prepared as per WO 2006/109085 A1] (3.88 g, 10.0 mmol) in ethanol (30 ml) and the mixture was stirred at room temperature under a hydrogen atmosphere for 1 hour. Methanol (20 ml) was added to aid dissolution and the mixture was stirred at room temperature under a hydrogen atmosphere for 16 hours. The mixture was filtered, the catalyst was rinsed with methanol (3×20 ml) and the combined filtrates were evaporated in vacuo to afford methyl 2,4-dihydroxy-5-isopropylbenzoate (2.10 g, 100%) as a colourless solid. $^1$H NMR (DMSO-d$_6$) 10.54 (1H, s), 10.44 (1H, br s), 7.52 (1H, s), 6.37 (1H, s), 3.85 (3H, s), 3.08 (1H, m), 1.13 (6H, d). MS: [M+H]$^+$ 211.

Preparation A3

4-Hydroxy-5-isopropyl-2-methoxybenzoic acid

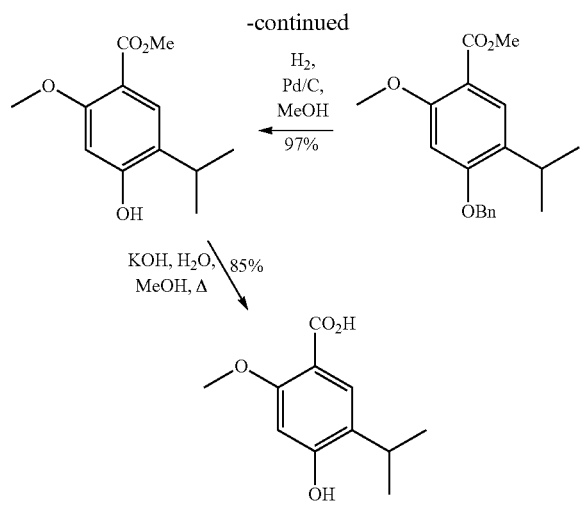

A mixture of methyl 2,4-dihydroxy-5-isopropylbenzoate (1.05 g, 5.0 mmol) and anhydrous potassium carbonate (828 mg, 6.0 mmol) in acetonitrile (25 ml) was treated with benzyl bromide (0.655 ml, 5.5 mmol) and the mixture was stirred at room temperature for 24 hours. The solvent was removed in vacuo and the residue was treated with water (50 ml). The solid material was collected by suction filtration, rinsed with water (2×50 ml) and sucked dry under reduced pressure to afford methyl 4-benzyloxy-2-hydroxy-5-isopropylbenzoate (1.25 g, 83%) as colourless needles. $^1$H NMR (DMSO-$d_6$) 10.68 (1H, br s), 7.57 (1H, s), 7.48-7.40 (4H, m), 7.34 (1H, m), 6.64 (1H, s), 5.20 (2H, s), 3.87 (3H, s), 3.18 (1H, m), 1.17 (6H, d). MS: [M+H]$^+$ 301.

Anhydrous potassium carbonate (450 mg, 3.26 mmol) and dimethyl sulphate (0.25 ml, 2.64 mmol) were added to a suspension of methyl 4-benzyloxy-2-hydroxy-5-isopropylbenzoate (650 mg, 2.17 mmol) in acetonitrile (20 ml) and the mixture was stirred and held at reflux for 16 hours. Upon cooling to room temperature the solvent was removed in vacuo and the residue acidified by the addition of 2M hydrochloric acid (20 ml). The organic material was extracted with ethyl acetate (2×30 ml) and the combined organic extracts were evaporated in vacuo to afford methyl 4-benzyloxy-5-isopropyl-2-methoxybenzoate (644 mg, 95%) as a pale yellow solid. $^1$H NMR (DMSO-$d_6$) 7.56 (1H, s), 7.50 (2H, d), 7.43 (2H, t), 7.37 (1H, t), 6.80 (1H, s), 5.26 (2H, s), 3.83 (3H, s), 3.75 (3H, s), 3.19 (1H, m), 1.17 (6H, d). MS: [M+H]$^+$ 315.

10% Palladium on carbon (80 mg) was added to a suspension of methyl 4-benzyloxy-5-isopropyl-2-methoxybenzoate (624 mg, 1.99 mmol) in methanol (16 ml) and the mixture was stirred at room temperature under a hydrogen atmosphere for 3 hours. The mixture was filtered, the catalyst was rinsed with methanol (3×5 ml) and the combined filtrates were evaporated in vacuo to afford methyl 4-hydroxy-5-isopropyl-2-methoxybenzoate (432 mg, 97%) as an off-white solid. $^1$H NMR (DMSO-$d_6$) 10.18 (1H, br s), 7.52 (1H, s), 6.52 (1H, s), 3.73 (3H, s), 3.71 (3H, s), 3.11 (1H, m), 1.14 (6H, d). MS: [M+Na]$^+$ 247.

Aqueous potassium hydroxide (50% w/v, 0.5 ml) was added to a suspension of methyl 2-hydroxy-5-isopropyl-4-methoxybenzoate (418 mg, 1.87 mmol) in methanol (4 ml) and water (2 ml) and the mixture was stirred and held at reflux for 4 hours. Upon cooling to room temperature the organic solvent was removed in vacuo and the residue acidified by the addition of 2M hydrochloric acid (10 ml). The solid material was collected by suction filtration, rinsed with water (2×10 ml) and sucked dry under reduced pressure to afford 4-hydroxy-5-isopropyl-2-methoxybenzoic acid (332 mg, 85%) as an off-white solid. $^1$H NMR (DMSO-$d_6$) 11.88 (1H, br s), 10.11 (1H, s), 7.54 (1H, s), 6.51 (1H, s), 3.75 (3H, s), 3.11 (1H, m), 1.13 (6H, d). MS: [M+Na]$^+$ 233.

Preparation A4

2-Hydroxy-5-isopropyl-4-methoxybenzoic acid

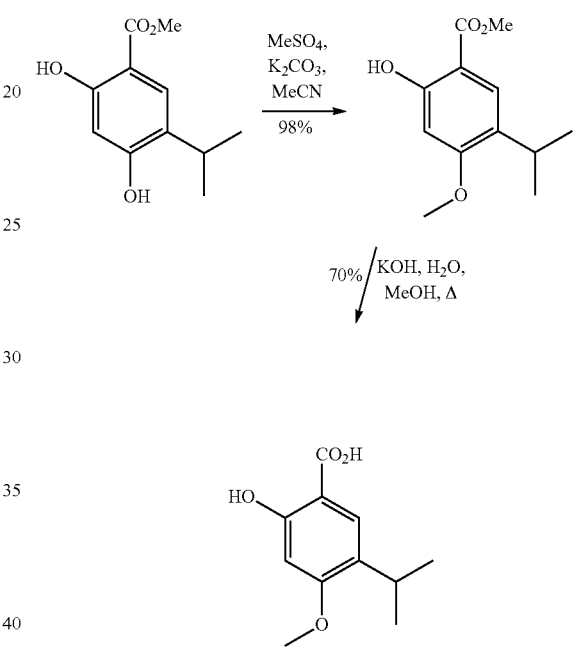

A mixture of methyl 2,4-dihydroxy-5-isopropylbenzoate (420 mg, 2.0 mmol) and anhydrous potassium carbonate (331 mg, 2.4 mmol) in acetonitrile (10 ml) was treated with dimethyl sulphate (0.2 ml, 2.1 mmol) and the mixture was stirred at room temperature for 16 hours. The solvent was removed in vacuo and the residue acidified by the addition of 2M hydrochloric acid (10 ml). The solid material was collected by suction filtration, rinsed with water (2×10 ml) and sucked dry under reduced pressure to afford methyl 2-hydroxy-5-isopropyl-4-methoxybenzoate (440 mg, 98%) as a colourless solid.

1H NMR (DMSO-$d_6$) 10.70 (1H, br s), 7.54 (1H, s), 6.53 (1H, s), 3.87 (3H, s), 3.84 (3H, s), 3.12 (1H, m), 1.13 (6H, d). MS: [M+H]$^+$ 225.

Aqueous potassium hydroxide (50% w/v, 0.2 ml) was added to a suspension of methyl 2-hydroxy-5-isopropyl-4-methoxybenzoate (420 mg, 1.88 mmol) in methanol (5 ml) and water (2 ml) and the mixture was stirred and held at reflux for 3 hours. Upon cooling to room temperature the organic solvent was removed in vacuo and the residue acidified by the addition of 2M hydrochloric acid (10 ml). The solid material was collected by suction filtration, rinsed with water (2×10 ml) and sucked dry under reduced pressure to afford 2-hydroxy-5-isopropyl-4-methoxybenzoic acid (275 mg, 70%) as a colourless solid. $^1$H NMR (DMSO-$d_6$) 13.50 (1H, br s), 11.40 (1H, br s), 7.53 (1H, s), 6.51 (1H, s), 3.83 (3H, s), 3.12 (1H, m), 1.13 (6H, d). MS: M+H+ 211.

Preparation A5

5-Isopropyl-2,4-dimethoxybenzoic acid

Preparation A6

2-Allyloxy-4-hydroxy-5-isopropylbenzoic acid

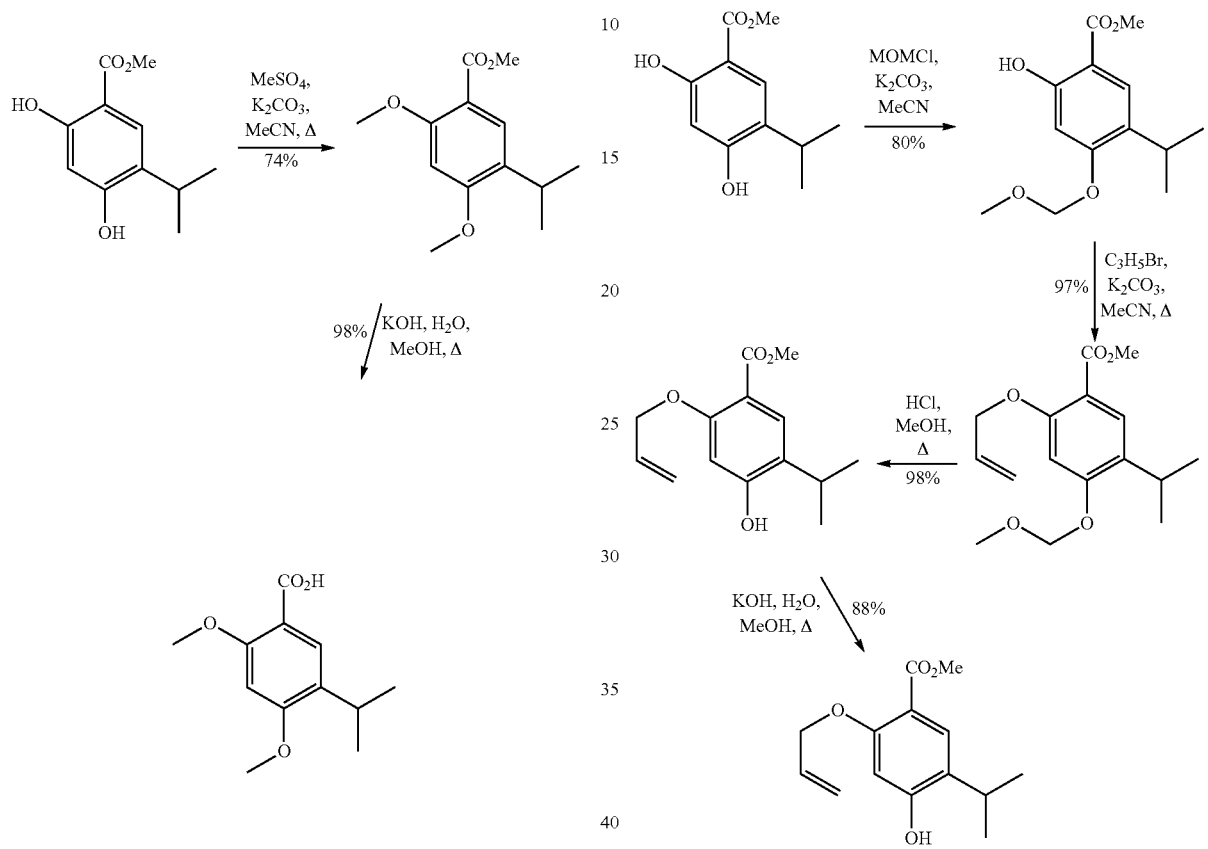

A mixture of methyl 2,4-dihydroxy-5-isopropylbenzoate (420 mg, 2.0 mmol) and anhydrous potassium carbonate (662 mg, 4.8 mmol) in acetonitrile (10 ml) was treated with dimethyl sulphate (0.4 ml, 4.2 mmol) and the mixture was stirred at room temperature for 16 hours and then held at reflux for 6 hours. Upon cooling to room temperature the solvent was removed in vacuo and the residue acidified by the addition of 2M hydrochloric acid (10 ml). The solid material was collected by suction filtration, rinsed with water (2×10 ml) and sucked dry under reduced pressure to afford methyl 5-isopropyl-2,4-dimethoxybenzoate (350 mg, 74%) as a colourless solid. $^1$H NMR (DMSO-$d_6$) 7.53 (1H, s), 6.67 (1H, s), 3.92 (3H, s), 3.86 (3H, s), 3.75 (3H, s), 3.13 (1H, m), 1.14 (6H, d). MS: [M+Na]+ 261.

Aqueous potassium hydroxide (50% w/v, 0.2 ml) was added to a suspension of methyl 5-isopropyl-2,4-dimethoxybenzoate (330 mg, 1.39 mmol) in methanol (5 ml) and water (2 ml) and the mixture was stirred and held at reflux for 3 hours. Upon cooling to room temperature the organic solvent was removed in vacuo and the residue acidified by the addition of 2M hydrochloric acid (10 ml). The organic material was extracted with ethyl acetate (2×30 ml) and the combined organic extracts were evaporated in vacuo to afford 5-isopropyl-2,4-dimethoxybenzoic acid (305 mg, 98%) as an off-white solid. $^1$H NMR (DMSO-$d_6$) 12.07 (1H, br s), 7.57 (1H, s), 6.64 (1H, s), 3.90 (3H, s), 3.85 (3H, s), 3.13 (1H, m), 1.14 (6H, d). MS: [M+H]+ 225.

A mixture of methyl 2,4-dihydroxy-5-isopropylbenzoate (1.05 g, 5.0 mmol) and anhydrous potassium carbonate (828 mg, 6.0 mmol) in acetonitrile (25 ml) was treated with chloromethyl methyl ether (0.4 ml, 5.27 mmol) and the mixture was stirred at room temperature for 3 hours. The solvent was removed in vacuo and the residue treated with water (30 ml). The solid material was collected by suction filtration, rinsed with water (2×20 ml) and sucked dry under reduced pressure to afford methyl 2-hydroxy-5-isopropyl-4-(methoxymethyloxy)benzoate (1.02 g, 80%) as a colourless solid. $^1$H NMR (DMSO-$d_6$) 10.61 (1H, br s), 7.58 (1H, s), 6.62 (1H, s), 5.30 (2H, s), 3.88 (3H, s), 3.42 (3H, s), 3.17 (1H, m), 1.17 (6H, d). MS: [M+H]+ 255.

A mixture of methyl 2-hydroxy-5-isopropyl-4-(methoxymethyloxy)benzoate (995 mg, 3.92 mmol) and anhydrous potassium carbonate (650 mg, 4.71 mmol) in acetonitrile (25 ml) was treated with allyl bromide (0.356 ml, 4.11 mmol) and the mixture was stirred and held at reflux for 16 hours. Upon cooling to room temperature the solvent was removed in vacuo, water (30 ml) was added and the organic material was extracted with dichloromethane (2×30 ml). The combined organic extracts were evaporated to dryness in vacuo to afford methyl 2-allyloxy-5-isopropyl-4-(methoxymethyloxy)benzoate (1125 mg, 97%) as pale yellow oil. $^1$H NMR (DMSO-$d_6$) 7.58 (1H, s), 6.78 (1H, s), 6.03 (1H, m), 5.52 (1H, dm), 5.33 (2H, s), 5.28 (1H, dm), 4.61 (2H, m), 3.78 (3H, s), 3.42 (3H, s), 3.19 (1H, m), 1.18 (6H, d). MS: [M+Na]⁺ 317.

Concentrated hydrochloric acid (0.4 ml) was added to a solution of methyl 2-allyloxy-5-isopropyl-4-(methoxymethyloxy)benzoate (1049 mg, 3.57 mmol) in methanol (25 ml) and the mixture was stirred and held at reflux for 3 hours. Upon cooling to room temperature the volatile material and solvent were removed in vacuo to afford methyl 2-allyloxy-4-hydroxy-5-isopropylbenzoate (880 mg, 98%) as a pale green oil. ¹H NMR (DMSO-d₆) 10.18 (1H, s), 7.54 (1H, s), 6.51 (1H, s), 6.03 (1H, m), 5.51 (1H, dm), 5.27 (1H, dm), 4.52 (2H, m), 3.73 (3H, s), 3.10 (1H, m), 1.15 (6H, d). MS: [M+Na]⁺ 273.

Aqueous potassium hydroxide (50% w/v, 2 ml) was added to a mixture of methyl 2-allyloxy-4-hydroxy-5-isopropylbenzoate (860 mg, 3.44 mmol) in methanol (12 ml) and water (4 ml) and the mixture was stirred and held at reflux for 5 hours. Upon cooling to room temperature the organic solvent was removed in vacuo and the residue acidified by the addition of 2M hydrochloric acid (30 ml). The solid material was collected by suction filtration, rinsed with water (2×20 ml) and sucked dry under reduced pressure to afford 2-allyloxy-4-hydroxy-5-isopropylbenzoic acid (715 mg, 88%) as a pale green solid. ¹H NMR (DMSO-d₆) 11.92 (1H, br s), 10.08 (1H, s), 7.56 (1H, s), 6.48 (1H, s), 6.03 (1H, m), 5.50 (1H, dm), 5.27 (1H, dm), 4.53 (2H, m), 3.11 (1H, m), 1.13 (6H, d). MS: [M+Na]⁺259.

Preparation A7

4-Allyloxy-2-hydroxy-5-isopropylbenzoic acid

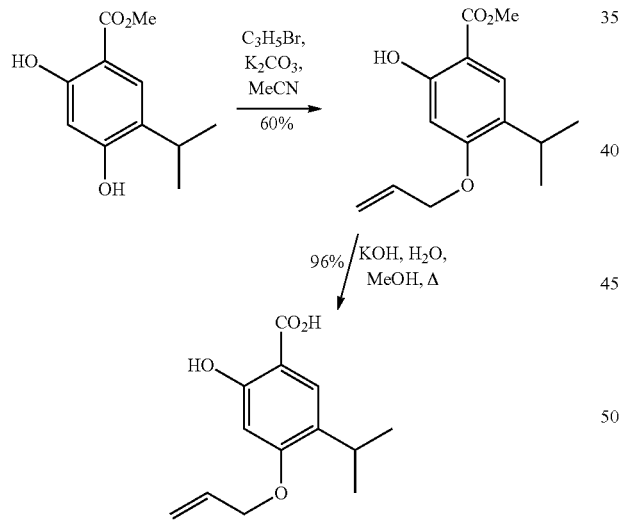

A mixture of methyl 2,4-dihydroxy-5-isopropylbenzoate (420 mg, 2.0 mmol) and anhydrous potassium carbonate (662 mg, 4.8 mmol) in acetonitrile (10 ml) was treated with allyl bromide (0.35 ml, 4.0 mmol) and the mixture was stirred at room temperature for 24 hours. The solvent was removed in vacuo and the residue acidified by the addition of 2M hydrochloric acid (10 ml). The organic material was extracted with dichloromethane (2×20 ml), the combined organic extracts were evaporated in vacuo and the residue subjected to column chromatography on silica. Elution with 2-10% ethyl acetate in petroleum ether afforded methyl 4-allyloxy-2-hydroxy-5-isopropylbenzoate (330 mg, 60%) as a colourless solid. ¹H NMR (DMSO-d₆) 10.68 (1H, s), 7.55 (1H, s), 6.54 (1H, s), 6.06 (1H, m), 5.42 (1H, dm), 5.29 (1H, dm), 4.65 (2H, m), 3.88 (3H, s), 3.16 (1H, m), 1.16 (6H, d).

Aqueous potassium hydroxide (50% w/v, 0.2 ml) was added to a suspension of methyl 4-allyloxy-2-hydroxy-5-isopropylbenzoate (313 mg, 1.25 mmol) in methanol (6 ml) and water (2 ml) and the mixture was stirred and held at reflux for 4 hours. Upon cooling to room temperature the organic solvent was removed in vacuo and the residue acidified by the addition of 2M hydrochloric acid (10 ml). The solid material was collected by suction filtration, rinsed with water (2×10 ml) and sucked dry under reduced pressure to afford 4-allyloxy-2-hydroxy-5-isopropylbenzoic acid (285 mg, 96%) as a colourless solid. ¹H NMR (DMSO-d₆) 13.50 (1H, br s), 11.40 (1H, s), 7.55 (1H, s), 6.51 (1H, s), 6.06 (1H, m), 5.42 (1H, dm), 5.28 (1H, dm), 4.64 (2H, m), 3.17 (1H, m), 1.17 (6H, d). MS: [M+H]⁺ 237.

Preparation A8

2,4-Bis-allyloxy-5-isopropylbenzoic acid

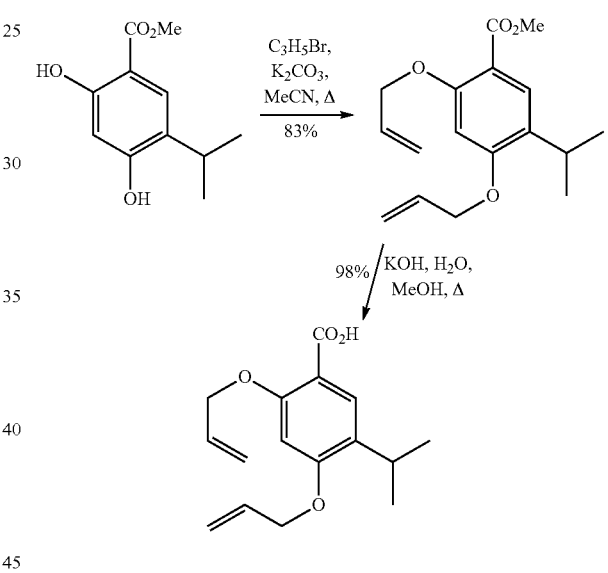

A mixture of methyl 2,4-dihydroxy-5-isopropylbenzoate (420 mg, 2.0 mmol) and anhydrous potassium carbonate (662 mg, 4.8 mmol) in acetonitrile (10 ml) was treated with allyl bromide (0.364 ml, 4.2 mmol) and the mixture was stirred at room temperature for 16 hours. A further portion of allyl bromide (0.364 ml, 4.2 mmol) was added and the mixture was stirred and held at reflux for a further 16 hours. Upon cooling to room temperature the solvent was removed in vacuo and the residue acidified by the addition of 2M hydrochloric acid (20 ml). The organic material was extracted with ethyl acetate (2×20 ml) and the combined organic extracts were evaporated in vacuo to afford methyl 2,4-bis-allyloxy-5-isopropylbenzoate (480 mg, 83%) as a pale yellow oil. ¹H NMR (DMSO-d₆) 7.56 (1H, s), 6.68 (1H, s), 6.07 (2H, m), 5.51 (1H, dm), 5.44 (1H, dm), 5.28 (2H, m), 4.68 (2H, m), 4.64 (2H, m), 3.75 (3H, s), 3.18 (1H, m), 1.16 (6H, d). MS: [M+Na]⁺ 313.

Aqueous potassium hydroxide (50% w/v, 0.5 ml) was added to a mixture of methyl 2,4-bis-allyloxy-5-isopropylbenzoate (450 mg, 1.55 mmol) in methanol (6 ml) and water (2 ml) and the mixture was stirred and held at reflux for 3 hours. Upon cooling to room temperature the organic solvent was removed in vacuo and the residue acidified by the addition of 2M hydrochloric acid (10 ml). The solid material was collected by suction filtration, rinsed with water (2×10 ml) and sucked dry under reduced pressure to afford 2,4-bis-allyloxy-5-isopropylbenzoic acid (418 mg, 98%) as an off-white solid. $^1$H NMR (DMSO-$d_6$) 12.16 (1H, br s), 7.58 (1H, s), 6.66 (1H, s), 6.07 (2H, m), 5.51 (1H, dm), 5.44 (1H, dm), 5.28 (2H, m), 4.68 (2H, m), 4.64 (2H, m), 3.17 (1H, m), 1.15 (6H, d). MS: [M+Na]$^+$ 299.

Preparation A9

4-Hydroxy-5-isopropyl-2-(methoxymethyloxy)benzoic acid

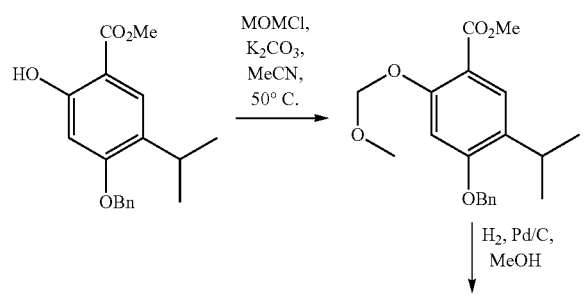

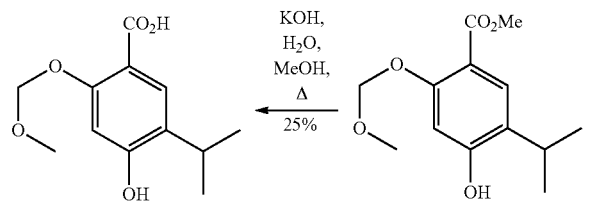

A mixture of methyl 4-benzyloxy-2-hydroxy-5-isopropylbenzoate (900 mg, 3.0 mmol) and anhydrous potassium carbonate (994 mg, 7.2 mmol) in acetonitrile (20 ml) was treated with chloromethyl methyl ether (0.24 ml, 6.6 mmol) and the mixture was stirred and held at 50° C. for 24 hours whereupon further anhydrous potassium carbonate (994 mg, 7.2 mmol) and chloromethyl methyl ether (0.96 ml, 26.4 mmol) were added and the mixture was stirred and held at 50° C. for a further 4 days. Upon cooling to room temperature the solvent was removed in vacuo and the residue treated with water (30 ml). The organic material was extracted with dichloromethane (2×20 ml) and the combined organic extracts were evaporated in vacuo to afford crude methyl 4-benzyloxy-5-isopropyl-2-(methoxymethyloxy)benzoate as a pale yellow oil that was used in the next step without further purification. $^1$H NMR (DMSO-$d_6$) 7.57 (1H, s), 7.48 (2H, d), 7.44 (2H, t), 7.38 (1H, t), 6.90 (1H, s), 5.23 (4H, s), 3.78 (3H, s), 3.39 (3H, s), 3.21 (1H, m), 1.17 (6H, d). MS: [M+Na]$^+$ 367.

The crude methyl 4-benzyloxy-5-isopropyl-2-(methoxymethyloxy)benzoate was dissolved in methanol (20 ml), 10% palladium on carbon (160 mg) was added and the mixture was stirred at room temperature under a hydrogen atmosphere for 16 hours. The mixture was filtered, the catalyst was rinsed with methanol (3×5 ml) and the combined filtrates were evaporated in vacuo to afford crude methyl 4-hydroxy-5-isopropyl-2-(methoxymethyloxy)benzoate as a colourless oily solid that was used in the next step without further purification. $^1$H NMR (DMSO-$d_6$) 10.19 (1H, br s), 7.52 (1H, s), 6.57 (1H, s), 5.13 (2H, s), 3.73 (3H, s), 3.40 (3H, s), 3.11 (1H, m), 1.13 (6H, d). MS: [M−H]$^-$ 253.

The crude methyl 4-hydroxy-5-isopropyl-2-(methoxymethyloxy)benzoate was dissolved in methanol (20 ml) and water (8 ml), aqueous potassium hydroxide (50% w/v, 5 ml) was added and the mixture was stirred and held at reflux for 16 hours. Upon cooling to room temperature the organic solvent was removed in vacuo and the residue acidified by the addition of 2M hydrochloric acid (30 ml). The organic material was extracted with ethyl acetate (2×20 ml) and the combined organic extracts were evaporated in vacuo to afford a yellow oil that was subjected to column chromatography on a Strata-NH2 cartridge. Elution with 2M ammonia in methanol afforded crude 4-hydroxy-5-isopropyl-2-(methoxymethyloxy)benzoic acid (180 mg, 25%) as a pale grey solid that was used without further purification. MS: [M+Na]$^+$ 263.

Preparation A10

2-Hydroxy-5-isopropyl-4-(methoxymethyloxy)benzoic acid

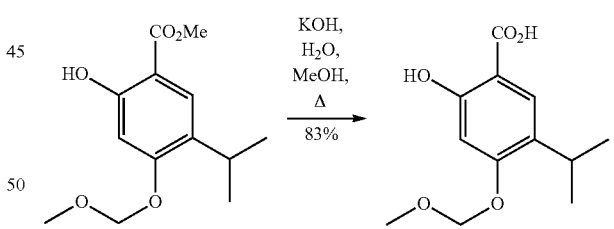

Aqueous potassium hydroxide (50% w/v, 1 ml) was added to a mixture of methyl 2-hydroxy-5-isopropyl-4-(methoxymethyloxy)benzoate (508 mg, 2.0 mmol) in methanol (10 ml) and water (4 ml) and the mixture was stirred and held at reflux for 6 hours. Upon cooling to room temperature the organic solvent was removed in vacuo and the residue acidified by the addition of 2M hydrochloric acid (30 ml). The solid material was collected by suction filtration, rinsed with water (2×20 ml) and sucked dry under reduced pressure to afford 2-hydroxy-5-isopropyl-4-(methoxymethyloxy)benzoic acid (400 mg, 83%) as a colourless solid. $^1$H NMR (DMSO-$d_6$) 13.60 (1H, br s), 11.30 (1H, br s), 7.58 (1H, s), 6.58 (1H, s), 5.30 (2H, s), 3.42 (3H, s), 3.15 (1H, m), 1.18 (6H, d). MS: [M+H]$^+$ 241.

Preparation A11

2,4-Bis-(methoxymethyloxy)-5-isopropylbenzoic acid

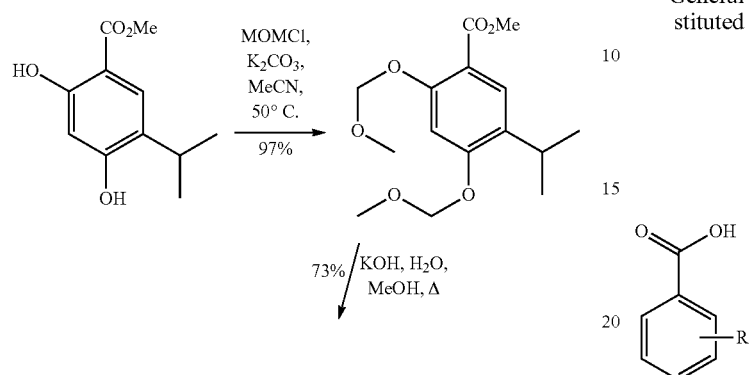

A mixture of methyl 2,4-dihydroxy-5-isopropylbenzoate (420 mg, 2.0 mmol) and anhydrous potassium carbonate (332 mg, 2.4 mmol) in acetonitrile (12 ml) was treated with chloromethyl methyl ether (0.16 ml, 2.1 mmol) and the mixture was stirred at room temperature for 16 hours whereupon further anhydrous potassium carbonate (1.38 g, 10.0 mmol) and chloromethyl methyl ether (0.76 ml, 10.0 mmol) were added and the mixture was stirred and held at 50° C. for a further 4 days. Upon cooling to room temperature the solvent was removed in vacuo and the residue treated with water (30 ml). The organic material was extracted with dichloromethane (2×20 ml) and the combined organic extracts were evaporated in vacuo to afford methyl 2,4-bis-(methoxymethyloxy)-5-isopropylbenzoate (580 mg, 97%) as a pale yellow oil. $^1$H NMR (DMSO-$d_6$) 7.57 (1H, s), 6.88 (1H, s), 5.32 (2H, s), 5.20 (2H, s), 3.78 (3H, s), 3.41 (6H, s), 3.21 (1H, m), 1.17 (6H, d). MS: [M+Na]$^+$ 321.

Aqueous potassium hydroxide (50% w/v, 1.0 ml) was added to a mixture of methyl 2,4-bis-(methoxymethyloxy)-5-isopropylbenzoate (560 mg, 1.88 mmol) in methanol (12 ml) and water (4 ml) and the mixture was stirred and held at reflux for 3 hours. Upon cooling to room temperature the organic solvent was removed in vacuo and the residue diluted with water (20 ml) and acidified by the addition of 2M hydrochloric acid (10 ml). The organic material was extracted with dichloromethane (2×20 ml) and the combined organic extracts were evaporated in vacuo. The residue was triturated with a mixture of petroleum ether and diethyl ether to afford 2,4-bis-(methoxymethyloxy)-5-isopropylbenzoic acid (392 mg, 73%) as a colourless solid. $^1$H NMR (DMSO-$d_6$) 12.38 (1H, br s), 7.59 (1H, s), 6.84 (1H, s), 5.31 (2H, s), 5.20 (2H, s), 3.41 (6H, s), 3.21 (1H, m), 1.18 (6H, d). MS: [M+Na]$^+$ 307.

Preparation B1

General Method for the Synthesis of N-benzoyl Substituted 5-(4-methylpiperazin-1-ylmethyl)-2,3-dihydro-1H-isoindoles

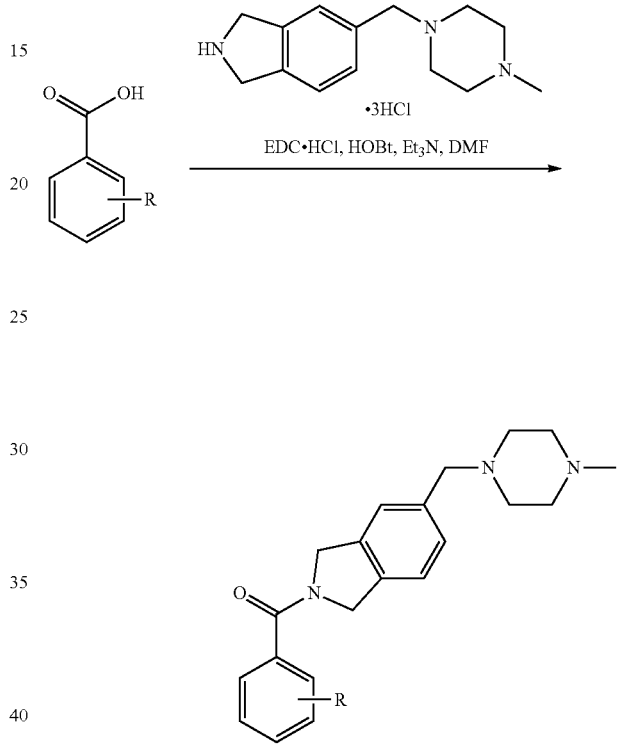

5-(4-Methylpiperazin-1-ylmethyl)-2,3-dihydro-1H-isoindole trihydrochloride (409 mg, 1.2 mmol) was added to a mixture of the substituted benzoic acid (1.0 mmol), 1-(3-dimethylaminopropyl)-3-ethylcarbodiimide hydrochloride (211 mg, 1.1 mmol), 1-hydroxybenzotriazole (149 mg, 1.1 mmol) and triethylamine (606 mg, 6.0 mmol) in N,N-dimethylformamide (8 ml) and the mixture was stirred at room temperature or at 50-80° C. for 16 hours. The solvent was removed in vacuo and the residue treated with aqueous sodium hydrogen carbonate and methanol. The organic solvent was removed in vacuo and the aqueous layer was removed by decantation. The dark oily residues were subjected to column chromatography on silica. Elution with 5-10% methanol in dichloromethane afforded the corresponding N-benzoyl substituted 5-(4-methylpiperazin-1-ylmethyl)-2,3-dihydro-1H-isoindole. If necessary the compounds were further purified by column chromatography on an SCX cartridge eluting with 2M ammonia in methanol.

Examples 1 to 9

By following the general method described above, the compounds of Examples 1 to 9 set out in the Table below were prepared.

| Example | Compound | Chemical Name | Substituted benzoic acid precursor | N.M.R. Data | M.S. |
|---|---|---|---|---|---|
| 1 | | (4-Hydroxy-5-isopropyl-2-methoxy-phenyl)-[5-(4-methyl-piperazin-1-ylmethyl)-1,3-dihydro-isoindol-2-yl]-methanone | 4-Hydroxy-5-isopropyl-2-methoxy-benzoic acid | 1H NMR (DMSO-d6) [mixture of rotamers] 9.66 (1H, s), 7.32 (1H, m), 7.24-7.16 (2H, m), 6.97 (1H, s), 6.52 (1H, s), 4.75 (2H, br s), 4.51 and 4.49 (2H, 2 × s), 3.72 (3H, s), 3.44 and 3.41 (2H, 2 × s), 3.14 (1H, m), 2.31 (8H, br s), 2.14 and 2.12 (3H, 2 × s), 1.15 (6H, d) | MS: [M + H]+ 424 |
| 2 | | (2-Hydroxy-5-isopropyl-4-methoxy-phenyl)-[5-(4-methyl-piperazin-1-ylmethyl)-1,3-dihydro-isoindol-2-yl]-methanone | 2-Hydroxy-5-isopropyl-4-methoxy-benzoic acid | 1H NMR (DMSO-d6) [mixture of rotamers] 10.28 and 10.23 (1H, 2 × br s), 7.35-7.20 (3H, br m), 7.12 (1H, s), 6.50 (1H, s), 4.78 (4H, br s), 3.80 (3H, s), 3.43 (2H, s), 3.13 (1H, m), 2.33 (8H, br s), 2.15 (3H, s), 1.15 (6H, d) | MS: [M + H]+ 424 |
| 3 | | (5-Isopropyl-2,4-dimethoxy-phenyl)-[5-(4-methyl-piperazin-1-ylmethyl)-1,3-dihydro-isoindol-2-yl]-methanone | 5-Isopropyl-2,4-dimethoxy-benzoic acid | 1H NMR (DMSO-d6) [mixture of rotamers] 7.30 (1H, m), 7.24-7.16 (2H, m), 7.04 (1H, s), 6.71 (1H, s), 4.75 (2H, br s), 4.51 and 4.49 (2H, 2 × s), 3.90 (3H, s), 3.84 (3H, s), 3.44 and 3.41 (2H, 2 × s), 3.19 (1H, m), 2.31 (8H, br s), 2.14 and 2.12 (3H, 2 × s), 1.13 (6H, d) | MS: [M + H]+ 438 |

| Example | Compound | Chemical Name | Substituted benzoic acid precursor | N.M.R. Data | M.S. |
|---|---|---|---|---|---|
| 4 | | (2-Allyloxy-4-hydroxy-5-isopropyl-phenyl)-[5-(4-methyl-piperazin-1-ylmethyl)-1,3-dihydro-isoindol-2-yl]-methanone | 2-Allyloxy-4-hydroxy-5-isopropyl-benzoic acid | 1H NMR (DMSO-d6) [mixture of rotamers] 9.64 (1H, s), 7.30 (1H, m), 7.24-7.16 (2H, m), 6.99 (1H, s), 6.53 (1H, s), 5.97 (1H, m), 5.32 (1H, dm), 5.17 (1H, dm), 4.77 (2H, br s), 4.53 (4H, m), 3.44 and 3.41 (2H, 2 × s), 3.13 (1H, m), 2.34 (8H, br s), 2.14 and 2.12 (3H, 2 × s), 1.15 (6H, d) | MS: [M + H]+ 450 |
| 5 | | (4-Allyloxy-2-hydroxy-5-isopropyl-phenyl)-[5-(4-methyl-piperazin-1-ylmethyl)-1,3-dihydro-isoindol-2-yl]-methanone | 4-Allyloxy-2-hydroxy-5-isopropyl-benzoic acid | 1H NMR (DMSO-d6) [mixture of rotamers] 10.28 and 10.23 (1H, 2 × br s), 7.35-7.18 (3H, br m), 7.13 (1H, br s), 6.50 (1H, s), 6.09 (1H, m), 5.44 (1H, dm), 5.30 (1H, dm), 4.78 (4H, br s), 4.58 (2H, m), 3.45 (2H, br s), 3.18 (1H, m), 2.40 (8H, br s), 2.21 (3H, br s), 1.18 (6H, d) | MS: [M + H]+ 450 |

-continued

| Example | Compound | Chemical Name | Substituted benzoic acid precursor | N.M.R. Data | M.S. |
|---|---|---|---|---|---|
| 6 | 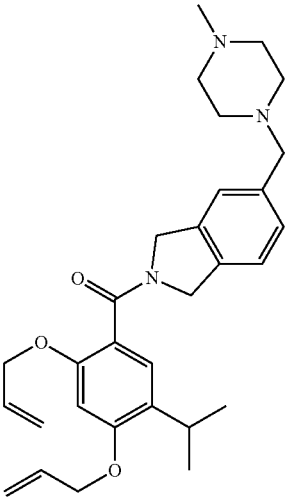 [SMILES: C=CCOc1cc(OCC=C)c(C(C)C)cc1C(=O)N1Cc2ccc(CN3CCN(C)CC3)cc2C1] | (2,4-Bis-allyloxy-5-isopropyl-phenyl)-[5-(4-methyl-piperazin-1-ylmethyl)-1,3-dihydro-isoindol-2-yl)-methanone | 2,4-Bis-allyloxy-5-isopropyl-benzoic acid | 1H NMR (DMSO-d6) [mixture of rotamers] 7.31 (1H, m), 7.24-7.17 (2H, m), 7.06 (1H, s), 6.72 (1H, s), 6.11 (1H, m), 5.98 (1H, m), 5.47 (1H, dm), 5.35-5.28 (2H, m), 5.17 (1H, dm), 4.78 (2H, br s), 4.64 (4H, m), 4.52 and 4.50 (2H, 2 × s), 3.44 and 3.41 (2H, 2 × s), 3.21 (1H, m), 2.33 (8H, br s), 2.14 and 2.12 (3H, 2 × s), 1.17 (6H, d) | MS: [M + H]+ 490 |
| 7 | 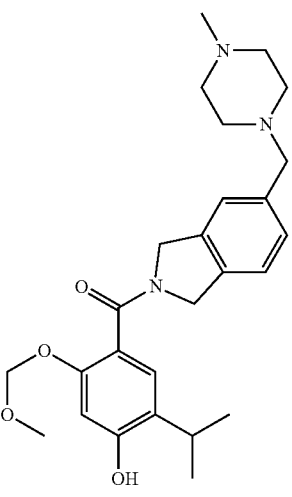 [SMILES: COCOc1cc(O)c(C(C)C)cc1C(=O)N1Cc2ccc(CN3CCN(C)CC3)cc2C1] | [4-Hydroxy-5-isopropyl-2-(methoxymethyloxy)-phenyl]-[5-(4-methyl-piperazin-1-ylmethyl)-1,3-dihydro-isoindol-2-yl]-methanone | 4-Hydroxy-5-isopropyl-2-(methoxymethyloxy)-benzoic acid | 1H NMR (DMSO-d6) [mixture of rotamers] 9.68 (1H, s), 7.32 (1H, m), 7.24-7.17 (2H, m), 7.01 (1H, s), 6.69 (1H, s), 5.13 (2H, s), 4.77 (2H, br s), 4.54 and 4.53 (2H, 2 × s), 3.45 and 3.43 (2H, 2 × s), 3.34 (3H, s), 3.12 (1H, m), 2.31 (8H, br s), 2.14 and 2.12 (3H, 2 × s), 1.14 (6H, d) | MS: [M + H]+ 454 |

-continued

| Example | Compound | Chemical Name | Substituted benzoic acid precursor | N.M.R. Data | M.S. |
|---|---|---|---|---|---|
| 8 | | [2-Hydroxy-5-isopropyl-4-(methoxymethyl-oxy)-phenyl]-[5-(4-methyl-piperazin-1-ylmethyl)-1,3-dihydro-isoindol-2-yl]-methanone | 2-Hydroxy-5-isopropyl-4-(methoxy-methyloxy)-benzoic acid | 1H NMR (DMSO-d6) [mixture of rotamers] 10.12 and 10.07 (1H, 2 × br s), 7.35-7.20 (3H, br m), 7.12 (1H, br s), 6.67 (1H, s), 5.23 (2H, s), 4.80-4.65 (4H, br m), 3.42 (5H, s), 3.18 (1H, m), 2.36 (8H, br s), 2.15 (3H, s), 1.18 (6H, d) | MS: [M + H]+ 454 |
| 9 | | [5-Isopropyl-2,4-bis-(methoxymethyl-oxy)-phenyl]-[5-(4-methyl-piperazin-1-ylmethyl)-1,3-dihydro-isoindol-2-yl]-methanone | 2,4-Bis-(methoxymethyl-oxy)-5-isopropyl-benzoic acid | 1H NMR (DMSO-d6) [mixture of rotamers] 7.31 (1H, m), 7.24-7.16 (2H, m), 7.14 (1H, s), 6.91 (1H, s), 5.27 (2H, s), 5.18 (2H, s), 4.78 (2H, br s), 4.55 and 4.53 (2H, 2 × s), 3.44 (6H, s), 3.44 and 3.41 (2H, 2 × s), 3.23 (1H, m), 2.34 (8H, br s), 2.16 and 2.14 (3H, 2 × s), 1.19 (6H, d) | MS: [M + H]+ 498 |

Example 10

Preparation of diethyl-carbamic acid 5-diethylcarbamoyloxy-2-isopropyl-4-[5-(4-methyl-piperazin-1-ylmethyl)-1,3-dihydro-isoindole-2-carbonyl]-cyclohexa-1,3-dienyl ester

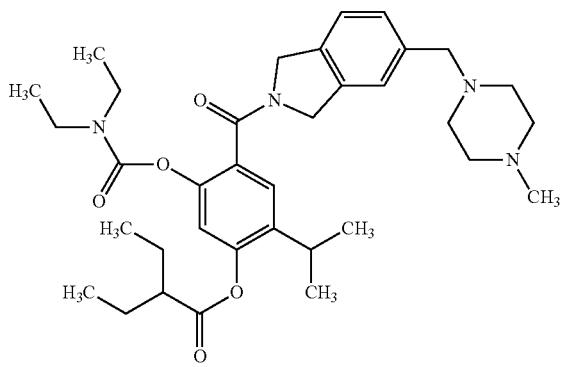 [SMILES: CCC(CC)C(=O)Oc1cc(OC(=O)N(CC)CC)c(C(=O)N2Cc3ccc(CN4CCN(C)CC4)cc3C2)cc1C(C)C]

To a solution of (2,4-dihydroxy-5-isopropyl-phenyl)-[5-(4-methyl-piperazin-1-ylmethyl)-1,3-dihydro-isoindol-2-yl]-methanone (1.0 g, 2.44 mmol) in THF (25 mL) containing $Et_3N$ (0.68 mL, 4.88 mmol) and N,N-4-dimethylaminopyridine (5 mg, 0.41 mmol) was added N,N-diethylcarbamoyl chloride (1.5 mL, 11.62 mmol). The solution was heated to 60° C. for 18 h when EtOAc (50 mL) and 10% aq $K_2CO_3$ (50 mL) were added. The organic phase was washed with saturated brine (30 mL) and the organic phase was separated and evaporated to a small volume. A solution of the residue in DCM was applied to a column containing silica gel and the product eluted successively with DCM followed by 0.2% aqueous ammonia in 5% MeOH in DCM. The fractions containing product were evaporated from DCM followed by diethyl ether to give the title compound as a foam 1.07 g. 1H NMR (400 MHz, DMSO-d6): 7.44 (1H, d), 7.37-7.30 (1H, m), 7.30-7.15 (2H, m), 7.01 (1H, s), 4.75 (2H, s), 4.61 (2H, d), 3.56-3.40 (4H, m), 3.33 (4H, d), 3.24 (3H, d), 3.19-3.09 (2H, m), 3.09-2.95 (2H, m), 2.85-2.56 (4H, m), 2.42 (3H, s), 1.38-0.76 (18H, m); m/z 608 (MH).

Examples 11 to 13

Examples 11 to 13 were prepared by a manner analogous to that described for Example 10.

| Example number | Chemical Structure | m/z (MH) | NMR |
|---|---|---|---|
| 11 | 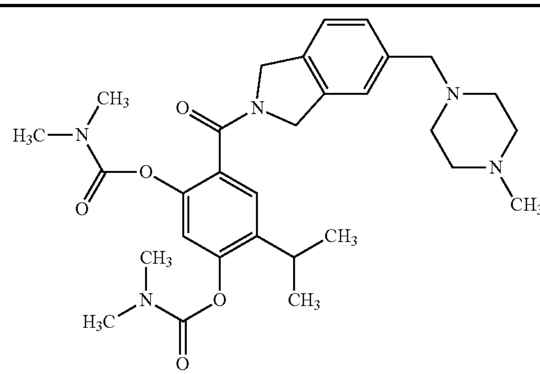 | 552 | 1H NMR (400 MHz, DMSO-d6): 7.43 (1H, d), 7.35-7.28 (1H, m), 7.26-7.16 (2H, m), 7.01 (1H, s), 4.77 (2H, d), 4.61 (2H, d), 3.43 (2H, d), 3.09 (3H, s), 3.08-3.02 (1H, m), 2.95 (3H, s), 2.88 (3H, s), 2.78 (3H, s), 2.44-2.21 (8H, m), 2.14 (3H, d), 1.20 (6H, dd). |
| 12 | 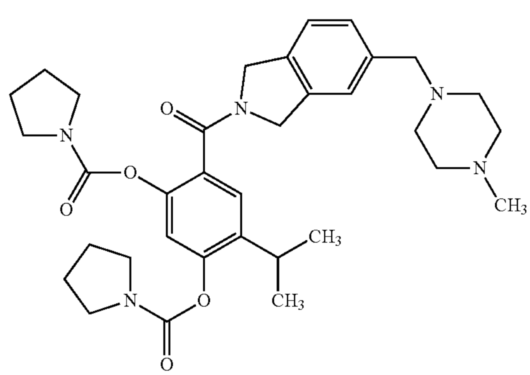 [SMILES: CC(C)c1cc(C(=O)N2Cc3ccc(CN4CCN(C)CC4)cc3C2)c(OC(=O)N2CCCC2)cc1OC(=O)N1CCCC1] | 604 | 1H NMR (400 MHz, DMSO-d6): 7.42 (1H, d), 7.36-7.30 (1H, m), 7.25-7.15 (2H, m), 7.06 (1H, s), 4.76 (2H, s), 4.61 (2H, d), 3.58-3.50 (2H, m), 3.44 (2H, d), 3.41-3.34 (2H, m), 3.31 (1H, m), 3.28-3.23 (1H, m), 3.18 (2H, t), 3.12-3.01 (1H, m), 2.33 (8H, s), 2.15 (3H, d), 2.01-1.84 (4H, m), 1.80-1.70 (4H, m), 1.20 (6H, d). |

| Example number | Chemical Structure | m/z (MH) | NMR |
|---|---|---|---|
| 13 | 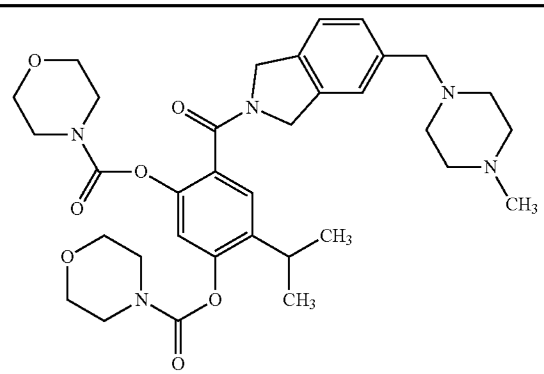 | 636 | 1H NMR (400 MHz, DMSO-d6): 7.47 (1H, d), 7.39-7.29 (1H, m), 7.28-7.16 (2H, m), 7.08 (1H, s), 4.78 (2H, s), 4.61 (2H, d), 3.67 (6H, s), 3.54-3.36 (10H, m), 3.36-3.21 (2H, m), 3.13-3.00 (1H, m), 2.33 (8H, s), 2.14 (3H, d), 1.27-1.16 (6H, m). |

Example 14

Diethyl-carbamic acid 5-hydroxy-4-isopropyl-2-[5-(4-methyl-piperazin-1-ylmethyl)-1,3-dihydro-isoindole-2-carbonyl]-phenyl ester and

Example 15

Diethyl-carbamic acid 5-hydroxy-2-isopropyl-4-[5-(4-methyl-piperazin-1-ylmethyl)-1,3-dihydro-isoindole-2-carbonyl]-phenyl ester

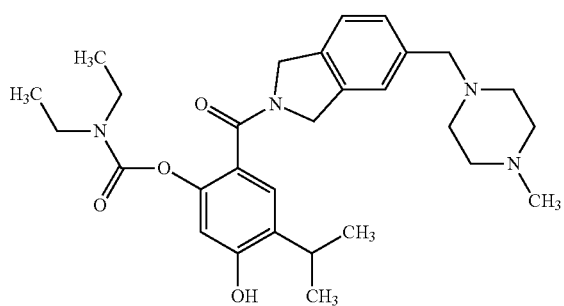

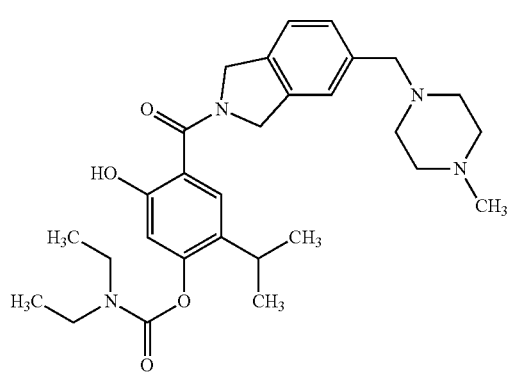

A solution of the product of Example 10 (0.826 g) dissolved in MeOH (36 mL) and 2M NaOH aq (4 mL) was heated at 60° C. for 24 h. The solution was cooled to RT and to this was added 5M-HCl (1.6 mL, to pH 6) and the solution evaporated to a small volume. The residue was partitioned between saturated brine and EtOAc and the organic layer was evaporated to an oil. The oil was purified by preparative hplc (basic method) to give the two separated isomeric mono-diethylcarbamoyl derivatives:

Diethyl-carbamic acid 5-hydroxy-4-isopropyl-2-[5-(4-methyl-piperazin-1-ylmethyl)-1,3-dihydro-isoindole-2-carbonyl]-phenyl ester (137 mg)

1H NMR (400 MHz, DMSO-d6): 9.86 (1H, s), 7.35-7.25 (1H, m), 7.25-7.12 (3H, m), 6.65 (1H, s), 4.71 (2H, s), 4.57 (2H, d), 3.43 (2H, d), 3.27-3.08 (5H, m), 2.32 (8H, s), 2.14 (3H, d), 1.18 (6H, d), 1.05-0.85 (6H, m), m/z 509 (MH) and Diethyl-carbamic acid 5-hydroxy-2-isopropyl-4-[5-(4-methyl-piperazin-1-ylmethyl)-1,3-dihydro-isoindole-2-carbonyl]-phenyl ester (292 mg)

1H NMR (400 MHz, DMSO-d6): 10.01 (1H, s), 7.37-7.27 (1H, m), 7.27-7.17 (2H, m), 7.15 (1H, d), 6.60 (1H, s), 4.79 (2H, s), 4.63 (2H, d), 3.44 (4H, m), 3.34 (2H, m), 3.01-2.87 (1H, m), 2.32 (8H, s), 2.14 (3H, d), 1.22 (3H, s), 1.15 (9H, d), m/z 509 (MH).

Examples 16 to 21

Examples 16 to 21 were prepared in a manner analogous to that described in Examples 14 and 15 by treating the diacylated derivatives (Examples 11, 12 and 13) with NaOH in MeOH (60° C. h, 3.5 h-24 h). The mixture of products was separated by preparative hplc.

| Example number | Chemical Structure | m/z (MH) | NMR | Preparative HPLC solvent conditions |
|---|---|---|---|---|
| 16 | 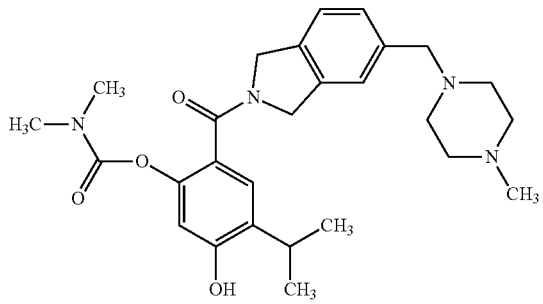<br>From Example 11 | 481 | 1H NMR (400 MHz, DMSO-d6): 9.88 (1H, s), 7.36-7.27 (1H, m), 7.27-7.13 (3H, m), 6.64 (1H, s), 4.74 (2H, s), 4.57 (2H, d), 3.46 (2H, d), 3.24-3.13 (1H, m), 2.85 (3H, s), 2.78 (3H, s), 2.61-2.30 (8H, m), 2.25 (3H, s), 1.18 (6H, d). | Acid* |
| 17 | 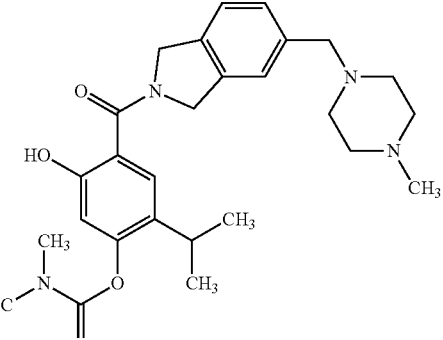<br>From Example 11 | 481 | 1H NMR (400 MHz, DMSO-d6): 10.01 (1H, d), 7.37-7.27 (1H, m), 7.27-7.11 (3H, m), 6.61 (1H, s), 4.79 (2H, s), 4.63 (2H, d), 3.50-3.41 (2H, m), 3.08 (3H, s), 3.01-2.86 (4H, m), 2.35 (8H, s), 2.17 (3H, d), 1.14 (6H, d). | Acid* |
| 18 | 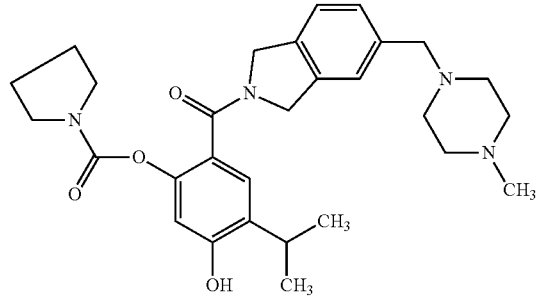 [SMILES: CC(C)c1cc(C(=O)N2Cc3ccc(CN4CCN(C)CC4)cc3C2)c(OC(=O)N2CCCC2)cc1O]<br>From Example 12 | 507 | 1H NMR (400 MHz, DMSO-d6): 9.88 (1H, s), 7.36-7.27 (1H, m), 7.27-7.12 (3H, m), 6.67 (1H, s), 4.73 (2H, s), 4.57 (2H, d), 3.43 (2H, d), 3.27 (2H, t), 3.23-3.09 (3H, m), 2.32 (8H, s), 2.14 (3H, d), 1.72 (4H, s), 1.18 (6H, d) | Basic |

-continued

| Example number | Chemical Structure | m/z (MH) | NMR | Preparative HPLC solvent conditions |
|---|---|---|---|---|
| 19 | 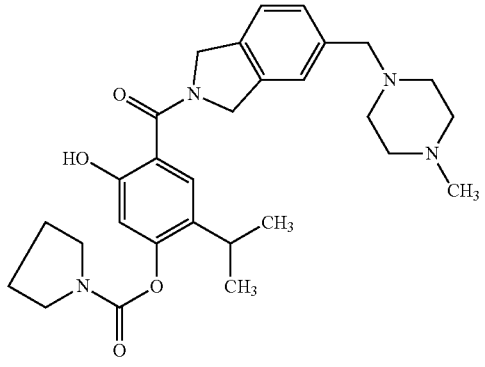 [SMILES: CC(C)c1cc(C(=O)N2Cc3ccc(CN4CCN(C)CC4)cc3C2)c(O)cc1OC(=O)N1CCCC1]<br>From Example 12 | 507 | 1H NMR (400 MHz, DMSO-d6): 9.95 (1H, s), 7.37-7.27 (1H, m), 7.27-7.17 (2H, m), 7.14 (1H, d), 4.79 (2H, s), 4.64 (2H, d), 3.53 (2H, t), 3.43 (2H, d), 3.40-3.34 (2H, m), 3.04-2.90 (1H, m), 2.32 (8H, s), 2.14 (3H, d), 1.98-1.81 (4H, m), 1.15 (6H, d). | Basic |
| 20 | 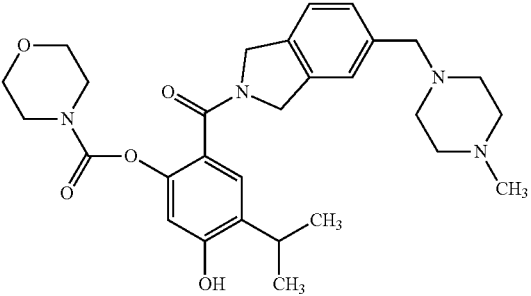 [SMILES: CC(C)c1cc(C(=O)N2Cc3ccc(CN4CCN(C)CC4)cc3C2)c(OC(=O)N2CCOCC2)cc1O]<br>From Example 13 | 523 | 1H NMR (400 MHz, DMSO-d6): 9.93(1H, s), 7.37-7.27 (1H, m), 7.26-7.14 (3H, m), 6.66 (1H, s), 4.74 (2H, s), 4.58 (2H, d), 3.53-3.25 (10H, m), 3.25-3.14 (1H, m), 2.32 (8H, s), 2.14 (3H, d), 1.19 (6H, d). | Basic |
| 21 | 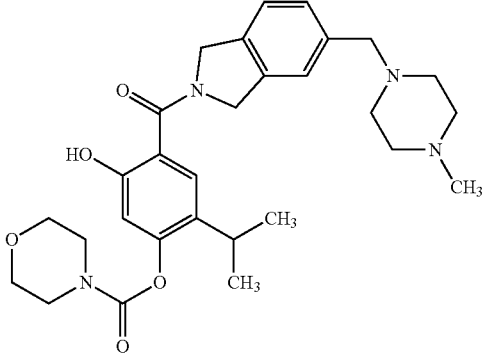 [SMILES: CC(C)c1cc(C(=O)N2Cc3ccc(CN4CCN(C)CC4)cc3C2)c(O)cc1OC(=O)N1CCOCC1]<br>From Example 13 | 523 | 1H NMR (400 MHz, DMSO-d6): 10.04 (1H, d), 7.37-7.26 (1H, m), 7.26-7.17 (2H, m), 7.16 (1H, d), 6.63 (1H, s), 4.79 (2H, s), 4.63 (2H, d), 3.65 (6H, d), 3.45 (4H, d), 3.00-2.88 (1H, m), 2.33 (8H, s), 2.14 (3H, d), 1.15 (6H, d). | Basic followed by acid* method |

*Isolation of the peaks from the preparative basic hplc method was by evaporation of solvent to give the free base. When the acidic hplc method was used, isolation was by evaporation followed by adsorption onto an SCX ion exchange column (2g, Stata) and subsequent elution with 2M NH₃ in MeOH.

Example 22

Carbonic acid tert-butyl ester 5-dimethylcarbamoyloxy-4-isopropyl-2,5-(4-methyl-piperazin-1-ylmethyl)-1,3-dihydro-isoindole-2-carbonyl-phenyl ester

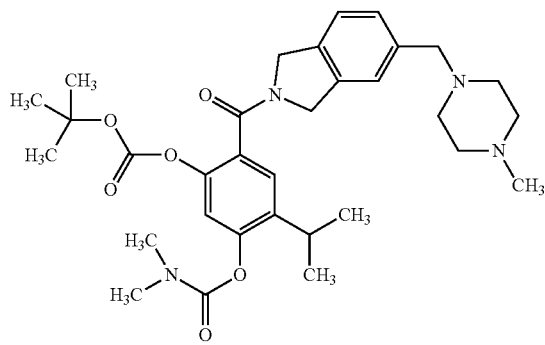 [SMILES: CC(C)c1cc(C(=O)N2Cc3ccc(CN4CCN(C)CC4)cc3C2)c(OC(=O)OC(C)(C)C)cc1OC(=O)N(C)C]

To a solution of dimethyl-carbamic acid 5-hydroxy-2-isopropyl-4-[5-(4-methyl-piperazin-1-ylmethyl)-1,3-dihydro-isoindole-2-carbonyl]-phenyl ester (Example 17, 50 mg) in THF (10 mL) was added di-t-butyl-dicarbonate (54.5 mg) and N,N-4-dimethylaminopyridine (1.25 mg). The solution was heated to 60° C. for 1 h, cooled to RT and evaporated to dryness. The residue was purified on silica gel and eluted with 0.2% aqueous ammonia in 5% MeOH in DCM. The fractions containing product were evaporated from DCM and diethylether to give the title compound as a foam (40 mg)

1H NMR (400 MHz, DMSO-d6): 7.51 (1H, d), 7.36-7.28 (1H, m), 7.26-7.17 (2H, m), 7.08 (1H, s), 4.77 (2H, s), 4.62 (2H, d), 3.44 (2H, d), 3.10 (3H, s), 3.05 (1H, dd), 2.95 (3H, s), 2.32 (8H, d), 2.14 (3H, d), 1.34 (9H, s), 1.21 (6H, dd).

The stereochemical assignment was confirmed by the observation of a nuclear Overhauser effect (nOe) between the butyl group and the isoindoline $CH_2N$.

Example 23

Carbonic acid 5-tert-butoxycarbonyloxy-4-isopropyl-2-[5-(4-methyl-piperazin-1-ylmethyl)-1,3-dihydro-isoindole-2-carbonyl]-phenyl ester tert-butyl ester

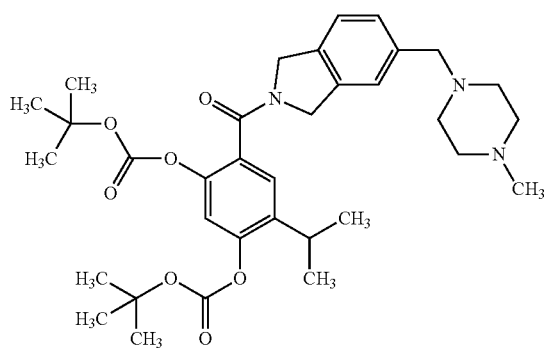 [SMILES: CC(C)c1cc(C(=O)N2Cc3ccc(CN4CCN(C)CC4)cc3C2)c(OC(=O)OC(C)(C)C)cc1OC(=O)OC(C)(C)C]

To a solution of (2,4-dihydroxy-5-isopropyl-phenyl)-[5-(4-methyl-piperazin-1-ylmethyl)-1,3-dihydro-isoindol-2-yl]-methanone (1 g, 2.44 mmol) in THF (25 mL) was added di-t-butyl-dicarbonate (1.17 g, 5.5 mmol) and N,N-4-dimethylaminopyridine (45 mg, 0.37 mmol). The solution was heated to 60° C. for 3 h then cooled to RT and evaporated to dryness. The residue was purified on silica gel eluting with DCM followed by 0.2% aqueous ammonia in 5% MeOH in DCM. The fractions containing product were evaporated to a foam to give the title compound (1.52 g). ¹H NMR (400 MHz, DMSO-d6): 7.58 (1H, d), 7.38-7.28 (1H, m), 7.28-7.15 (3H, m), 4.77 (2H, s), 4.61 (2H, d), 3.44 (2H, d), 3.09-2.96 (1H, m), 2.47-2.17 (8H, m), 2.15 (3H, d), 1.52 (9H, s), 1.34 (9H, s), 1.21 (6H, dd); m/z 610 (MH)

Example 24

2,2-Dimethyl-propionic acid 5-(2,2-dimethyl-propionyloxy)-2-isopropyl-4-[5-(4-methyl-piperazin-1-ylmethyl)-1,3-dihydro-isoindole-2-carbonyl]-phenyl ester dihydrochloride

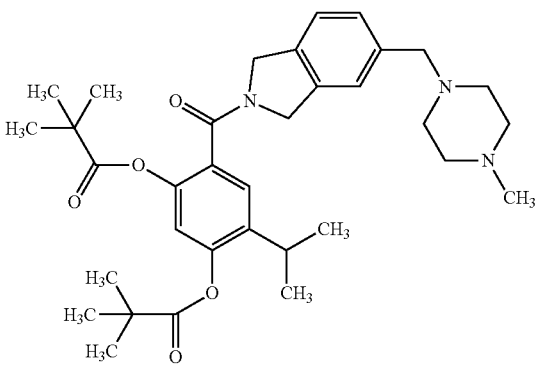 [SMILES: CC(C)c1cc(C(=O)N2Cc3ccc(CN4CCN(C)CC4)cc3C2)c(OC(=O)C(C)(C)C)cc1OC(=O)C(C)(C)C]

To a solution of (2,4-dihydroxy-5-isopropyl-phenyl)-[5-(4-methyl-piperazin-1-ylmethyl)-1,3-dihydro-isoindol-2-yl]-methanone (0.546 g, 1.33 mmol) in THF (10 mL) was added $Et_3N$ (0.464 mL), pivaloyl chloride (0.492 mL, 3.99 mmol) and N,N-4-dimethylaminopyridine (15 mg, 0.123 mmol). The solution was stirred at RT for 5 h then the solvent was removed by evaporation. The residue was partitioned between EtOAc and saturated $NaHCO_3$ and the organic phase was washed with saturated brine and dried ($Na_2SO_4$). The solvent was evaporated to give an oil which was dissolved in diethyl ether and EtOAc and to this solution was added 4M HCl in dioxan (0.67 mL, 2.68 mmol). The suspension was evaporated and dried under vacuum to give the title compound as a foam (0.835 g). ¹H NMR (400 MHz, DMSO-d6): 7.64-7.42 (3H, m), 7.39 (1H, d), 7.06 (1H, s), 4.78 (2H, s), 4.61 (2H, s), 3.44 (10H, s), 3.07-2.95 (1H, m), 2.79 (3H, s), 1.35 (9H, s), 1.20 (6H, d), 1.18-1.15 (9H, m); m/z 578 (MH).

Example 25

Isobutyric acid 5-isobutyryloxy-2-isopropyl-4-[5-(4-methyl-piperazin-1-ylmethyl)-1,3-dihydro-isoindole-2-carbonyl]-phenyl ester

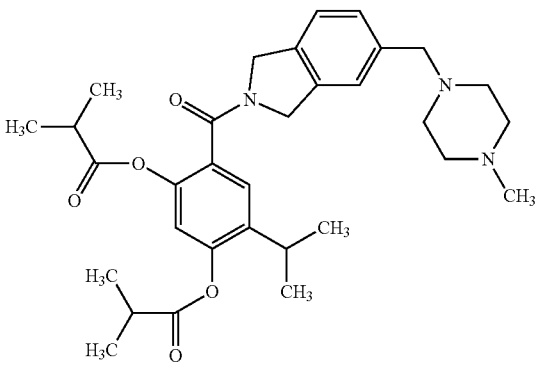 [SMILES: CC(C)C(=O)Oc1cc(OC(=O)C(C)C)c(C(C)C)cc1C(=O)N1Cc2ccc(CN3CCN(C)CC3)cc2C1]

The title compound was prepared in a manner analogous to that described for Example 24 using isobutyryl chloride. $^1$H NMR (400 MHz, DMSO-d6): 7.53 (1H, d), 7.38-7.28 (1H, m), 7.28-7.16 (2H, m), 7.07 (1H, s), 4.75 (2H, s), 4.58 (2H, d), 3.44 (2H, d), 3.07-2.95 (1H, m), 2.95-2.83 (1H, m), 2.72-2.64 (1H, m), 2.48-2.18 (8H, m), 2.15 (3H, d), 1.28 (6H, d), 1.23-1.17 (6H, m), 1.08 (6H, d); m/z 510 (MH).

Biological Activity

Example 26

Isothermal Titration Calorimetry

The ability of the parent phenolic compounds of the pro-drug compounds of the invention to bind to human Hsp90 proteins may be determined using isothermal titration calorimetry.

Isothermal titration calorimetry (ITC) experiments were performed with a VP-ITC titration calorimeter (Microcal Inc., Northampton, Mass., USA). Cloning, expression, and purification of the Human Hsp90α N-terminal domain were performed according to published methods (Jez, J. M. et al, *Chem. Biol.* 2003 April; 10(4):361-8.) Solutions of the human Hsp90α N-terminal domain and compound were prepared in a buffer comprising 25 mM Tris, 100 mM NaCl, 1 mM MgCl$_2$, 1 mM TCEP, 5% DMSO, pH 7.4. All solutions were filtered and degassed prior to a titration being carried out. The enthalpy change resulting from each injection of ligand was obtained through integration of the calorimetric signal. Data were analysed using Origin 7.0 (Microcal Software Inc., Northampton, Mass.). Heats of dilution were estimated using the final injections of each individual titration and subtracted before data fitting. Different ITC experimental formats were employed in order to obtain compound dissociation constants (Kd's) over a wide range of affinities. For weakly binding compounds a low c-value ITC method was used (Turnbull W. B. & Daranas A. H. *J. Am. Chem. Soc.* 2003 Dec. 3; 125(48): 14859-66) in which the protein was present at 10-20 μM in the calorimetric cell and the compound concentration was 1-20 mM in the injection syringe. In this type of experiment the stoichiometry parameter (N) was locked at 1 for data fitting. For Kd's in the 20-0.004 μM range the experiment was configured such that the binding site concentration divided by the Kd (c-value) was between 5 and 1000. For the majority of these experiments the protein concentration in the calorimetric cell was in the range 4-100 μM and the ligand concentration in the injection syringe ranged from 50-1500 μM. In rare cases where compound solubility was limiting, the compound solution was placed in the calorimetric cell and titrated with protein from the injection syringe, maintaining a c-value between 5 and 1000. Competition ITC experiments were used to access Kd's<4 nM by performing the titration in the presence of a weaker binding competitor according to the method described in Sigurskjold B. W. Anal Biochem. 2000 Jan. 15; 277(2):260-6.

Example 27

Anti-proliferative Activity

The anti-proliferative activities of the parent compounds of the pro-drugs of the invention may be determined by measuring the ability of the compounds to inhibition of cell growth in a number of cell lines such as the human colon cancer cell line HCT116 Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. Cell lines may be obtained from the ECACC (European Collection of cell Cultures).

The parent compound of the pro-drugs of Examples 1 to 25 i.e. (2,4-dihydroxy-5-isopropyl-phenyl)-[5-(4-methyl-piperazin-1-ylmethyl)-1,3-dihydro-isoindol-2-yl]-methanone, in the form of its L-lactate salt, was tested in anti-proliferative assays against one hundred cell lines by Oncodesign (Dijon, France). The IC$_{50}$ values against each cell line are set out in the table below and the figures in the table refer to nanomolar concentrations. The compounds were tested up to a concentration of 10,000 nanomolar.

| N° | Cell lines | Concentration of test compound (nanomolar) |
|---|---|---|
| BLOOD | | |
| 1 | ARH-77 | >10000 |
| 2 | BV-173 | 73 |
| 3 | CCRF-CEM | 107 |
| 4 | CCRF-CEM/VLB | >10000 |
| 5 | Daudi | 136 |
| 6 | EHEB | >10000 |
| 7 | HL-60 | 389 |
| 8 | HL-60/R10 | 847 |
| 9 | K-562 | 147 |
| 10 | K-562/Gleevec | 175 |
| 11 | KCL-22 | 24 |
| 12 | KG-1 | >10000 |
| 13 | LAMA-84 | 1098 |
| 14 | MC90 | 93 |
| 15 | NAMALWA | 93 |
| 16 | OCI-AML2 | >10000 |
| 17 | Raji | 881 |
| 18 | Ramos | 46 |
| 19 | RPMI 8226 | 10 |
| 20 | RPMI 8226/Dox40 | 213 |
| 21 | SUP-B15 | 37 |
| 22 | U-937 | 104 |
| BRAIN | | |
| 23 | CGL-1 | >10000 |
| 24 | CGL-3 | 75 |
| 25 | CGL-9 | 161 |
| BREAST | | |
| 26 | CAMA-1 | 22 |
| 27 | Evsa-T | 168 |
| 28 | HCC1954 | 28 |
| 29 | MCF-7 | >10000 |
| 30 | MCF-7/ras | 166 |
| 31 | MDA-MB-435 | 122 |
| 32 | MDA-MB-435S | 26 |
| 33 | ZR-75-1 | 131 |
| COLON | | |
| 34 | DLD-1 | 56 |
| 35 | HCT 116 | 38 |
| 36 | HCT-15 | >10000 |

| N° | Cell lines | Concentration of test compound (nanomolar) |
|---|---|---|
| 37 | LoVo | 51 |
| 38 | LS 174T | 159 |
| | CONNECTIVE TISSUE | |
| 39 | SW-872 | >10000 |
| | HEAD AND NECK | |
| 40 | BB30-HNSCC | 273 |
| 41 | BB49-HNSCC | 146 |
| 42 | FaDu | 29 |
| 43 | KB | 48 |
| 44 | KB3 | 48 |
| 45 | LB1617-HNSCC | 139 |
| 46 | LB771-HNSCC | 391 |
| | KIDNEY | |
| 47 | A-498 | 267 |
| 48 | BB64-RCC | >10000 |
| 49 | BB65-RCC | 1251 |
| 50 | Caki-1 | >10000 |
| 51 | LB1047-RCC | 58 |
| 52 | LB996-RCC | 158 |
| | LIVER | |
| 53 | Hep 3B2.1-7 | 95 |
| 54 | SK-HEP-1 | >10000 |
| | LUNG | |
| 55 | A-427 | 130 |
| 56 | Calu-1 | 270 |
| 57 | Calu-3 | >10000 |
| 58 | Calu-6 | 32 |
| 59 | LB11-SCLC/OC1 | 17 |
| 60 | LB12-SCLC/OC2 | 52 |
| 61 | LB13-SCLC/OC3 | 21 |
| 62 | LB37-NSCLC | 63 |
| 63 | LB61-NSCLC | >10000 |
| 64 | NCI-H1299 | 587 |
| 65 | NCI-H460 | 118 |
| 66 | NCI-H520 | 98 |
| 67 | NCI-H596 | 84 |
| 68 | NCI-H69 | 162 |
| 69 | NCI-H82 | >10000 |
| 70 | SK-MES-1 | 270 |
| | OVARY | |
| 71 | Caov-3 | 94 |
| 72 | IGROV-1 | 109 |
| 73 | IGROV-1/CDDP | 147 |
| 74 | NIH:OVCAR-3 | 45 |
| 75 | NIH:OVCAR-3/CPT20 | >10000 |
| 76 | PA-1 | >10000 |
| | PANCREAS | |
| 77 | BxPC-3 | 196 |
| 78 | Capan-2 | 144 |
| 79 | PANC-1 | 327 |
| | PROSTATE | |
| 80 | DU 145 | 85 |
| 81 | LNCaP-FGC | 78 |
| | SKIN | |
| 82 | A-375 | 1481 |
| 83 | A-375-SM | 340 |
| 84 | A-431 | 3799 |
| 85 | BB74-MEL | 162 |
| 86 | CMEL-5 | 130 |
| 87 | Hs 294T | 219 |
| 88 | LB1319-MEL | 35 |
| 89 | Malme-3M | 157 |
| 90 | SK-MEL-2 | 138 |
| 91 | SK-MEL-5 | 185 |
| 92 | UZG4-MEL | 180 |
| | STOMACH | |
| 93 | AGS | 66 |
| 94 | Hs 746T | 34 |
| 95 | KATO III | 162 |
| | THYROID | |
| 96 | FTC-238 | 26 |
| | URINARY BLADDER | |
| 97 | J82 | 20 |
| 98 | LB796-BLC | 83 |
| 99 | LB831-BLC | 149 |
| 100 | T24 | 852 |

The results demonstrate that (2,4-dihydroxy-5-isopropyl-phenyl)-[5-(4-methyl-piperazin-1-ylmethyl)-1,3-dihydro-isoindol-2-yl]-methanone has potent anti-proliferative activity against a wide range of different cell lines.

Pharmaceutical Formulations

Example 28

(i) Tablet Formulation

A tablet composition containing a compound of the invention is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the invention with 100 mg lactose and filling the resulting mixture into standard opaque hard gelatin capsules.

(iii) Injectable Formulation I

A parenteral composition for administration by injection may be prepared by dissolving a compound of the invention (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the invention (e.g. in salt form) (2 mg/ml) and mannitol (50 mg/ml), sterile filtering the solution and filling into sealable 1 ml vials or ampoules.

(v) Injectable Formulation III

A formulation for i.v. delivery by injection or infusion may be prepared by dissolving the compound of formula (I) (e.g. in a salt form) in water at 20 mg/ml. The vial is then sealed and sterilised by autoclaving.

(vi) Injectable formulation IV

A formulation for i.v. delivery by injection or infusion may be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the invention with pharmaceutical grade corn oil to give a concentration of 5 mg/ml. The composition is sterilised and filled into a suitable container.

(viii) Lyophilised formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) 2% Topical Gel Formulation

| | % w/w |
|---|---|
| Compound | 2.00 |
| Hydroxypropyl Methyl cellulose (Methocel F4M) | 2.50 |
| Polyethyleneoxide (Polyox WSR-205) | 0.25 |
| Propylene glycol | 10.00 |
| Methylparaben | 0.15 |
| Propylparaben | 0.05 |
| Purified Water to | 100.00 |

Example 29

Plasma Stability Studies

The ease with which pro-drug compounds of the invention may be converted to the active moiety may be assessed by measuring the in vitro plasma stability of the compounds. The method is based on the ability of plasma enzymes to metabolise compounds to the active moiety. Compounds are added to plasma and incubated at 37° C. for approximately 1 hour. Aliquots of plasma are removed at timed intervals and the compound extracted by the addition of acetonitrile containing an internal standard. All extracts are then analysed for parent compound, the active moiety and the internal standard using a compound specific LCMS-MS assay. Stability is measured by comparison of the peak area ratio of the parent compound and internal standard at time zero with the peak area ratio of the parent compound and internal standard in the incubated samples. Generation of the active moiety in samples is also assessed.

Example 30

Investigation of Whole Blood and Liver Homogenate Stability

The breakdown of a prodrug in vivo could occur in one or more of several different compartments including for example, but not limited to blood/plasma, liver, stomach, target tissue (e.g. tumour). The preferred location for optimum formation of the parent drug will depend on the disposition in vivo of the pro-drug and parent and an understanding of the optimum concentrations of each required in the circulation to maximise exposure to the active moiety in the target tissue. The potential for pro-drug molecules to deliver the active parent drug may be assessed in vitro by measuring the breakdown of a pro-drug in the presence of relevant body fluids. For the purpose of gaining a preliminary understanding of the stability of compounds of the invention to enzymatic hydrolysis in two such bodily compartments, compound turnover has been studied following incubation in whole blood and liver homogenate from mice and humans. The data obtained from these studies provide a preliminary understanding of which of the prodrugs are better able to deliver parent compound (i.e. are more rapidly broken down to parent compound) in these compartments. Further studies could also determine stability in other compartments (e.g. in the target tumours by measuring stability in tumour lysates). For these studies, human whole blood was collected from 3 male healthy volunteers in lithium heparin tubes. The blood was pooled and stored at room temperature for a maximum of 2 hours prior to initiation of incubations. Mouse blood was collected from 70 male mice, strain: Balb/c into lithium heparin tubes and pooled.

Mouse livers were obtained from 20 male mice, strain: Balb/c from stock animals. Human liver tissue was obtained from 3 individuals sourced from a UK human tissue bank. The livers were stored frozen. The livers were defrosted and then homogenised to form a homogenate of approximately 30% (w/v) in phosphate buffer, 100 mM, pH 7.4 (referred to as 'buffer'). Homogenates were kept on ice until use.

Each incubation consisted of a volume of 1 mL. Test compound dosing solutions were then spiked into each homogenate at a final compound concentration of 1 µM. Incubations were performed in the atmosphere in a shaking water bath at 37° C.

An aliquot of incubation samples was removed into an equal volume of ice-cold acetonitrile at various time points. Samples (whole blood/homogenate+acetonitrile) were centrifuged and aliquots of the supernatant were analysed by UPLC-MS/MS.

The compound X (2,4-dihydroxy-5-isopropyl-phenyl)-[5-(4-methyl-piperazin-1-ylmethyl)-1,3-dihydro-isoindol-2-yl]-methanone) and the compounds of Examples 1 to 24 were incubated in both whole blood and liver homogenate by Quotient Bioresearch (Rushden, UK). The percentage remaining of parent compound following incubation in whole blood/liver homogenate from human and mouse are set out in the table below.

| | Percentage remaining | | | |
|---|---|---|---|---|
| Example Number | Mouse blood | Human blood | Mouse Liver | Human Liver |
| X | 102% | 100% | 112% | 94% |
| 1 | 104% | 100% | 104% | 99% |
| 2 | 129% | 122% | 100% | 85% |
| 3 | 100% | 107% | 93% | 79% |
| 4 | 106% | 109% | 63% | 92% |
| 5 | 124% | 115% | 86% | 81% |
| 6 | 125% | 105% | 75% | 94% |
| 7 | 104%* | 109% | 115% | 92% |
| 8 | 104% | 114% | 79% | 102% |
| 9 | 105%* | 111% | 82% | 98% |
| 10 | 93% | 108% | 60% | 56% |
| 11 | 38% | 93% | 1% | 31% |
| 12 | 37% | 110% | 1% | 43% |
| 13 | 0% | 76% | 0% | 0% |
| 14 | 94% | 94% | 89% | 88% |
| 15 | 58% | 123% | 26% | 35% |
| 16 | 91% | 104% | 82% | 73% |
| 17 | 24% | 90% | 0% | 0% |
| 18 | 103%* | 110% | 80% | 65% |
| 19 | 79%* | 102% | 0% | 0% |
| 20 | 16% | 97% | 45% | 23% |
| 21 | 0% | 82% | 0% | 0% |
| 22 | 0% | 18% | 0% | 6% |
| 23 | 0% | 26% | 0% | 1% |
| 24 | 0% | 11% | 0% | 2% |

*For these incubations the percentage remaining stated is at 60 mins not 120 mins as stated.

Example 31

Mouse Pharmacokinetics

Balb/c mice are dosed with a prodrug by oral gavage. A single administration of one of the 24 examples is given and a dose volume of 10 mL/kg is used for PO doses.

Blood samples are collected in lithium heparin coated tubes at selected time points.

Plasma is isolated by centrifugation and frozen before analysis.

Plasma samples are prepared by liquid-liquid extraction with Acetonitrile containing internal standard. Quantification is by comparison with a standard calibration line constructed with each compound and using a LC-MS/MS method specific to each compound. Animals that had been dosed one of the 24 examples were analysed for prodrug and compound X (2,4-dihydroxy-5-isopropyl-phenyl)-[5-(4-methyl-piperazin-1-ylmethyl)-1,3-dihydro-isoindol-2-yl]-methanone). Pharmacokinetics parameters are calculated using WinNonLin® non compartmental analysis software.

The plasma $AUC_{0.25-2hrs}$ after PO administration of selected examples are set out in the table below. For examples 16, 17 and 11, plasma $AUC_{0.25-2hrs}$ was determined following a single dose of 120 µmoles/kg or 240 µmoles/kg. Accordingly, the compound of example 17 afforded optimal exposure of the active pharmaceutical agent relative to the starting dose.

| Example | Dose level (µmoles/kg) | $AUC_{0.25-2hrs}$ Example | Compound X |
|---|---|---|---|
| 16 | 120 | 280 | 73 |
| 17 | 120 | 1534 | 298 |
| 11 | 240 | 13512 | 247 |

In separate studies, examples 17 and 11 were shown to be well tolerated upon administration of four consecutive daily doses at 120 µmoles/kg or 240 µmoles/kg respectively.

Example 32

Determination of Antifungal Activity

The antifungal activity of the active parent compounds of the prodrug compounds of the invention is determined using the following protocol.

The compounds are tested against a panel of fungi including *Candida parapsilosis, Candida tropicalis, Candida albicans*-ATCC 36082 and *Cryptococcus neoformans*. The test organisms are maintained on Sabour and Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 µg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to 11 (concentration ranges are 64 to 0.125 µg/ml). Well 1 serves as a sterility control and blank for the spectrophotometric assays. Well 12 serves as a growth control. The microtitre plates are inoculated with 10 µl in each of well 2 to 11 (final inoculum size is $10^4$ organisms/ml). Inoculated plates are incubated for 48 hours at 35° C. The MIC values are determined spectrophotometrically by measuring the absorbance at 420 nm (Automatic Microplate Reader, DuPont Instruments, Wilmington, Del.) after agitation of the plates for 2 minutes with a vortex-mixer (Vorte-Genie 2 Mixer, Scientific Industries, Inc., Bolemia, N.Y.). The MIC endpoint is defined as the lowest drug concentration exhibiting approximately 50% (or more) reduction of the growth compared with the control well. With the turbidity assay this is defined as the lowest drug concentration at which turbidity in the well is <50% of the control (IC50). Minimal Cytolytic Concentrations (MCC) are determined by sub-culturing all wells from the 96-well plate onto a Sabourand Dextrose Agar (SDA) plate, incubating for 1 to 2 days at 35° C. and then checking viability.

Example 33

Methods Of Testing For Pain Reducing Or Pain Preventing Activity (I) Inflammatory Hyperalgesia Test Mechanical hyperalgesia may be examined in a rat model of inflammatory pain. Paw withdrawal thresholds to an increasing pressure stimulus are measured by the Randal-Sellito technique using an analgesymeter (Ugo Basile, Milan), in naïve animals prior to an intraplantar injection of complete Freund's complete adjuvant (FCA) into the left hind paw. 24 h later paw withdrawal thresholds are measured again prior to (predose) and then from 10 min to 6 h following drug or vehicle administration. Reversal of hyperalgesia in the ipsilateral paw is calculated according to the formula:

$$\% \text{ reversal} = \frac{\text{postdose threshold} - \text{predose threshold}}{\text{naive threshold} - \text{predose threshold}} \times 100$$

(ii) Neuropathic Hyperalgesia Test

Mechanical hyperalgesia may be examined in a rat model of neuropathic pain induced by partial ligation of the left sciatic nerve. Approximately 14 days following surgery mechanical withdrawal thresholds of both the ligated (ipsilateral) and non-ligated (contralateral) paw are measured prior to (predose) and then from 10 min to 6 h following drug or vehicle administration. Reversal of hyperalgesia at each time point is calculated according to the formula:

$$\% \text{ reversal} = \frac{\text{ipsilateral threshold postdose} - \text{ipsilateral threshold predose}}{\text{contralateral threshold predose} - \text{ipsilateral threshold predose}} \times 100$$

All experiments are carried out using groups of 6 animals. Stock concentrations of drugs are dissolved in distilled water and subsequent dilutions were made in 0.9% saline for subcutaneous administration in a volume of 4 mlkg$^{-1}$. All drugs are made up in plastic vials and kept in the dark.

Statistical analysis are carried out on withdrawal threshold readings (g) using ANOVA with repeated measures followed by Tukey's HSD test. Efficacy refers to the maximal reversal of hyperalgesia observed at the doses used.

(iii) Testing the Effects of the Active Parent Compounds of the Prodrug Compounds of the Invention in a Rat Model of Bone Cancer Pain Adult female rats are given intra-tibial injections of MRMZ-1 rat mammary gland carcinoma cells (3 µl, $10^7$ cells/ml). The animals typically gradually develop mechanical hyperalgesia, mechanical allodynia (skin sensitivity to non-noxious stimuli) and hind limb sparing, beginning on day 12-14 following cell injection. A compound of formula (0) (e.g. at a dose of 10 and 30 µg/kg s.c.) is administered 3 times a week from the day of cell injection, and the extent of inhibition of hind limb sparing and mechanical allodynia is determined in comparison to vehicle-treated controls.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention is further described by the following numbered paragraphs:

1. A compound of the formula (1a):

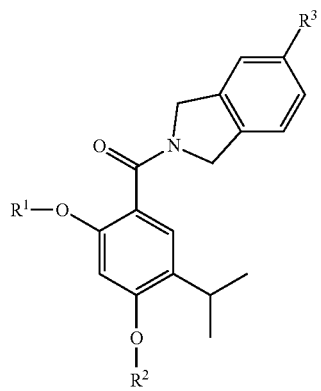

(1a)

or a salt, solvate, N-oxide or tautomer thereof;

wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;

$R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;

$R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and $R^3$ is a group D:

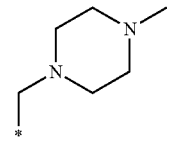

D wherein the asterisk denotes the point of attachment to the isoindoline ring;

but excluding the compound acetic acid 5-acetoxy-4-isopropyl-2-[5-(4-methyl-piperazin-1-ylmethyl)-1,3-dihydro-isoindole-2-carbonyl]-phenyl ester.

2. A compound according to paragraph 1 of the formula (1b):

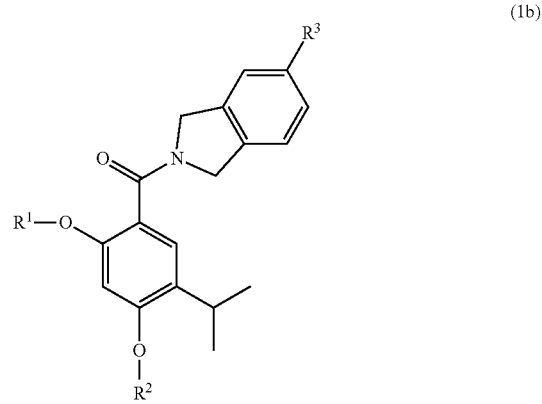

(1b)

or a salt, solvate, N-oxide or tautomer thereof;

wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;

$R^{1a}$ and $R^{2a}$ are the same or different and each is selected from hydrogen, $C_{1-2}$ alkyl, $C_{2-3}$ alkenyl and $C_{2-3}$ alkynyl wherein the $C_{1-2}$ alkyl is optionally substituted by methoxy;

$R^{1b}$ and $R^{2b}$ are the same or different and are selected from hydrogen and $C(O)NR^4R^5$, wherein $R^4$ and $R^5$ are both $C_{1-4}$ alkyl; or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; or $R^{1b}$ and $R^{2b}$ are the same or different and are selected from hydrogen and $C(O)R^{6a}$, wherein $R^{6a}$ is $C_{2-4}$ alkyl; or $R^{1b}$ and $R^{2b}$ are the same or different and are selected from hydrogen and $C(O)R^6$ where $R^6$ is selected from methyl, ethyl, propyl, isopropyl, butyl, 1-methylpropyl, 2-methylpropyl and tert-butyl; or one of $R^{1b}$ and $R^{2b}$ is $C(O)NR^{4a}R^{5a}$ where $R^{4a}$ and $R^{5a}$ are both $C_{1-4}$ alkyl, and the other of $R^{1b}$ and $R^{2b}$ is selected from $C(O)R^6$ and $C(O)OR^6$; and $R^3$ is a group D:

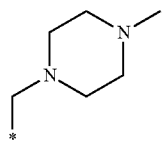

wherein the asterisk denotes the point of attachment to the isoindoline ring.

3. A compound according to paragraph 2 of the formula (1c):

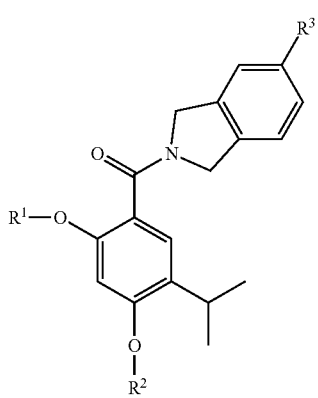

or a salt, solvate, N-oxide or tautomer thereof;
wherein $R^1$ is $R^{1b}$ and $R^2$ is $R^{2b}$; provided that at least one of $R^1$ and $R^2$ is other than hydrogen;
$R^{1b}$ and $R^{2b}$ are the same or different and are selected from hydrogen and $C(O)NR^4R^5$, wherein $R^4$ and $R^5$ are both $C_{1-4}$ alkyl; or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and
$R^3$ is a group D:

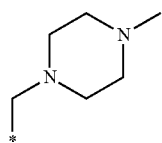

wherein the asterisk denotes the point of attachment to the isoindoline ring.

4. A compound according to paragraph 1 wherein $R^1$ is $R^{1a}$ and $R^2$ is $R^{2a}$.

5. A compound according to paragraph 4 wherein $R^{1a}$ and $R^{2a}$ are the same or different and each is selected from hydrogen, $C_{1-2}$ alkyl, $C_{2-3}$ alkenyl and $C_{2-3}$ alkynyl wherein the $C_{1-2}$ alkyl is optionally substituted by methoxy.

6. A compound according to paragraph 5 wherein $R^{1a}$ and $R^{2a}$ are each selected from hydrogen, methyl, methoxymethyl and allyl.

7. A compound according to paragraph 6 wherein $R^{1a}$ and $R^{2a}$ are each selected from hydrogen and methyl.

8. A compound according to paragraph 6 wherein $R^{1a}$ and $R^{2a}$ are each selected from hydrogen and methoxymethyl.

9. A compound according to paragraph 6 wherein $R^{1a}$ and $R^{2a}$ are each selected from hydrogen and allyl.

10. A compound according to paragraph 1 or claim 2 wherein $R^1$ is $R^{1b}$ and $R^2$ is $R^{2b}$.

11. A compound according to paragraph 3 or claim 10 wherein $R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl.

12. A compound according to paragraph 11 wherein $R^{1b}$ and $R^{2b}$ are the same or different and are selected from hydrogen and $C(O)NR^4R^5$.

13. A compound according to paragraph 12 wherein $R^4$ and $R^5$ are both $C_{1-3}$ alkyl.

14. A compound according to paragraph 13 wherein $R^4$ and $R^5$ are both selected from methyl and ethyl.

15. A compound according to paragraph 14 wherein $R^4$ and $R^5$ are both methyl.

16. A compound according to paragraph 11 wherein $R^{1b}$ and $R^{2b}$ are the same or different and are selected from hydrogen and $C(O)R^6$.

17. A compound according to paragraph 116 wherein $R^6$ is selected from methyl, ethyl, propyl, isopropyl, butyl, 1-methylpropyl, 2-methylpropyl and tert-butyl.

18. A compound according to paragraph 17 wherein $R^6$ is $C_{2-4}$ alkyl.

19. A compound according to paragraph 18 wherein $R^6$ is $C_{3-4}$ alkyl.

20. A compound according to paragraph 19 wherein $R^6$ is tert-butyl or isopropyl.

21. A compound according to paragraph 11 wherein $R^{1b}$ and $R^{2b}$ are the same or different and are selected from hydrogen and $C(O)OR^6$.

22. A compound according to paragraph 21 wherein $R^6$ is selected from methyl, ethyl, propyl, isopropyl, butyl, 1-methylpropyl, 2-methylpropyl and tert-butyl.

23. A compound according to paragraph 22 wherein $R^6$ is $C_{2-4}$ alkyl.

24. A compound according to paragraph 23 wherein $R^6$ is $C_{3-4}$ alkyl.

25. A compound according to paragraph 24 wherein $R^6$ is tert-butyl or isopropyl.

26. A compound according to paragraph 11 wherein one of $R^{1b}$ and $R^{2b}$ is $C(O)NR^4R^5$ where $R^4$ and $R^5$ are both $C_{1-4}$ alkyl, and the other of $R^{1b}$ and $R^{2b}$ is selected from $C(O)R^6$ and $C(O)OR^6$ where $R^6$ is as defined in any one of claims 17 to 25.

27. A compound according to paragraph 3 or claim 10 wherein $R^{1b}$ and $R^{2b}$ are the same or different and each is hydrogen or a group $C(O)NR^4R^5$, where $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups.

28. A compound according to paragraph 27 wherein the saturated heterocyclic ring is selected from azetidine, pyrrolidine, pyrrolidone, piperidine, piperidone, azepine, piperazine, 4-methylpiperazine, morpholine and thiomorpholine.

29. A compound according to paragraph 27 wherein $NR^4R^5$ forms a 5 or 6 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups.

30. A compound according to paragraph 29 wherein the saturated heterocyclic ring is selected from pyrrolidine, piperidine, piperazine, 4-methylpiperazine and morpholine.

31. A compound according to paragraph 30 wherein the saturated heterocyclic ring is pyrrolidine.

32. A compound according to paragraph 30 wherein the saturated heterocyclic ring is morpholine.

33. A compound according to any one of paragraphs 1 to 32 wherein one of $R^1$ and $R^2$ is other than hydrogen and the other is hydrogen.

34. A compound according to paragraph 33 wherein $R^2$ is other than hydrogen.

35. A compound according to any one of paragraphs 1 to 32 wherein $R^1$ and $R^2$ are both other than hydrogen.

36. A compound according to paragraph 1 which is selected from:
(4-hydroxy-5-isopropyl-2-methoxy-phenyl)-[5-(4-methyl-piperazin-1-ylmethyl)-1,3-dihydro-isoindol-2-yl]-methanone;
(2-hydroxy-5-isopropyl-4-methoxy-phenyl)-[5-(4-methyl-piperazin-1-ylmethyl)-1,3-dihydro-isoindol-2-yl]-methanone;
(5-isopropyl-2,4-dimethoxy-phenyl)-[5-(4-methyl-piperazin-1-ylmethyl)-1,3-dihydro-isoindol-2-yl]-methanone;
(2-allyloxy-4-hydroxy-5-isopropyl-phenyl)-[5-(4-methyl-piperazin-1-ylmethyl)-1,3-dihydro-isoindol-2-yl]-methanone;
(4-allyloxy-2-hydroxy-5-isopropyl-phenyl)-[5-(4-methyl-piperazin-1-ylmethyl)-1,3-dihydro-isoindol-2-yl]-methanone;
(2,4-bis-allyloxy-5-isopropyl-phenyl)-[5-(4-methyl-piperazin-1-ylmethyl)-1,3-dihydro-isoindol-2-yl]-methanone;
[4-hydroxy-5-isopropyl-2-(methoxymethyloxy)-phenyl]-[5-(4-methyl-piperazin-1-ylmethyl)-1,3-dihydro-isoindol-2-yl]-methanone;
[2-hydroxy-5-isopropyl-4-(methoxymethyloxy)-phenyl]-[5-(4-methyl-piperazin-1-ylmethyl)-1,3-dihydro-isoindol-2-yl]-methanone;
[5-isopropyl-2,4-bis-(methoxymethyloxy)-phenyl]-[5-(4-methyl-piperazin-1-ylmethyl)-1,3-dihydro-isoindol-2-yl]-methanone;
diethyl-carbamic acid 5-diethylcarbamoyloxy-2-isopropyl-4-[5-(4-methyl-piperazin-1-ylmethyl)-1,3-dihydro-isoindole-2-carbonyl]-phenyl ester;
dimethyl-carbamic acid 5-dimethylcarbamoyloxy-2-isopropyl-4-[5-(4-methyl-piperazin-1-ylmethyl)-1,3-dihydro-isoindole-2-carbonyl]-phenyl ester;
2-[2,4-bis-(pyrrolidin-1-ylcarbonyloxy)-5-isopropyl-benzoyl]-5-(4-methyl-piperazin-1-ylmethyl)-1,3-dihydro-isoindole;
2-[2,4-bis-(morpholin-4-ylcarbonyloxy)-5-isopropyl-benzoyl]-5-(4-methyl-piperazin-1-ylmethyl)-1,3-dihydro-isoindole; diethyl-carbamic acid 5-hydroxy-4-isopropyl-2-[5-(4-methyl-piperazin-1-ylmethyl)-1,3-dihydro-isoindole-2-carbonyl]-phenyl ester;
diethyl-carbamic acid 5-hydroxy-2-isopropyl-4-[5-(4-methyl-piperazin-1-ylmethyl)-1,3-dihydro-isoindole-2-carbonyl]-phenyl ester;
dimethyl-carbamic acid 5-hydroxy-4-isopropyl-2-[5-(4-methyl-piperazin-1-ylmethyl)-1,3-dihydro-isoindole-2-carbonyl]-phenyl ester;
dimethyl-carbamic acid 5-hydroxy-2-isopropyl-4-[5-(4-methyl-piperazin-1-ylmethyl)-1,3-dihydro-isoindole-2-carbonyl]-phenyl ester;
2-[2-(pyrrolidin-1-ylcarbonyloxy)-4-hydroxy-5-isopropyl-benzoyl]-5-(4-methyl-piperazin-1-ylmethyl)-1,3-dihydro-isoindole;
2-[4-(pyrrolidin-1-ylcarbonyloxy)-2-hydroxy-5-isopropyl-benzoyl]-5-(4-methyl-piperazin-1-ylmethyl)-1,3-dihydro-isoindole;
2-[2-(morpholin-4-ylcarbonyloxy)-4-hydroxy-5-isopropyl-benzoyl]-5-(4-methyl-piperazin-1-ylmethyl)-1,3-dihydro-isoindole;
2-[4-(morpholin-4-ylcarbonyloxy)-2-hydroxy-5-isopropyl-benzoyl]-5-(4-methyl-piperazin-1-ylmethyl)-1,3-dihydro-isoindole;
carbonic acid tert-butyl ester 5-dimethylcarbamoyloxy-4-isopropyl-2-[5-(4-methyl-piperazin-1-ylmethyl)-1,3-dihydro-isoindole-2-carbonyl]-phenyl ester;
carbonic acid 5-tert-butoxycarbonyloxy-4-isopropyl-2-[5-(4-methyl-piperazin-1-ylmethyl)-1,3-dihydro-isoindole-2-carbonyl]-phenyl ester tert-butyl ester;
2,2-dimethyl-propionic acid 5-(2,2-dimethyl-propionyloxy)-2-isopropyl-4-[5-(4-methyl-piperazin-1-ylmethyl)-1,3-dihydro-isoindole-2-carbonyl]-phenyl ester;
isobutyric acid 5-isobutyryloxy-2-isopropyl-4-[5-(4-methyl-piperazin-1-ylmethyl)-1,3-dihydro-isoindole-2-carbonyl]-phenyl ester;
and salts, solvates, tautomers and N-oxides thereof.

37. Dimethyl-carbamic acid 5-hydroxy-2-isopropyl-4-[5-(4-methyl-piperazin-1-ylmethyl)-1,3-dihydro-isoindole-2-carbonyl]-phenyl ester.

38. A compound of the formula (1), (1a), (1b), (1c), (2), (3), (4) or (5) and any Embodiment, group, sub-group or preference thereof as described herein, 39. A compound according to any one of paragraphs 1 to 38 in the form of a salt, solvate, tautomer or N-oxide 40. A compound according to any one of paragraphs 1 to 38 in the form of a salt, solvate or tautomer.

41. A compound according to any one of paragraphs 1 to 40 for use in medicine.

A compound according to any one of claims 1 to 40 for use:
(i) as an inhibitor of Hsp90; or
(ii) in the prophylaxis or treatment of a disease state or condition mediated by Hsp90; or
(iii) in treating a disease or condition comprising or arising from abnormal cell growth in a mammal; or
(iv) in treating cancer; or
(v) in the treatment of a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, neuroblastoma, glioma (a High grade glioma) or schwannoma; melanoma (e.g. malignant or metastatic melanoma); seminoma; teratocarcinoma; osteosarcoma; keratoacanthoma; thyroid follicular cancer; or Kaposi's sarcoma. A further example of a tumour of mesenchymal origin is Ewing's sarcoma; or (vi) in the treatment of a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, gall bladder, ovary, pancreas e.g. exocrine pancreatic carcinoma, stomach, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, glioma (a High grade glioma); melanoma (e.g. malignant or metastatic melanoma); osteosarcoma; or thyroid follicular cancer. A further example of a tumour of mesenchymal origin is Ewing's sarcoma; or (vii) in the treatment of a cancer selected from metastatic breast cancer which is HER2 positive; adenocarcinoma of the prostate; metastatic melanoma; non-small cell carcinoma of the lung (NSCLC); small cell carcinoma of the lung (SCLC); high grade gliomas; gastrointestinal stromal tumors (GIST); colorectal cancer; glioblastoma; melanoma; metastatic thyroid cancer; prostate cancer; and rectal cancer; or (viii) the treatment of a cancer selected from colorectal cancer; glioblastoma; melanoma; metastatic thyroid cancer; prostate cancer; and rectal cancer.

42. The use of a compound as defined in any one of paragraphs 1 to 40 for the manufacture of a medicament for any one or more uses as defined in paragraph 41.

43. A pharmaceutical composition comprising a compound according to any one of paragraphs 1 to 40 and a pharmaceutically acceptable carrier.

44. A pharmaceutical composition according to paragraph 43 which is adapted for oral administration.

45. A pharmaceutical composition according to paragraph 44 which is in the form of a tablet or capsule.

46. A method for the treatment of a disease state, condition or cancer as defined in paragraph 41 in a patient in need thereof (e.g. a mammal such as a human), which method comprises adiminstering to the said patient a therapeutically effective amount of a compound as defined in any one of paragraphs 1 to 40.

47. A compound of the formula (1a):

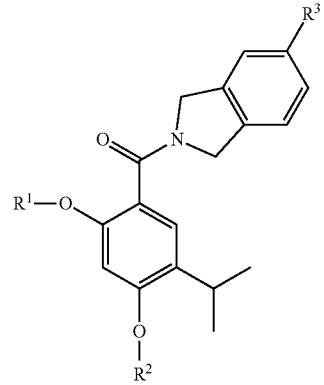

(1a)

or a salt, solvate, N-oxide or tautomer thereof; wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen; $R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is optionally substituted by $C_{1-2}$ alkoxy;

$R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and $R^3$ is a group D:

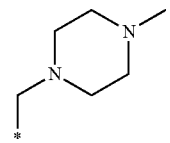

D wherein the asterisk denotes the point of attachment to the isoindoline ring;

but excluding the compound acetic acid 5-acetoxy-4-isopropyl-2-[5-(4-methyl-piperazin-1-ylmethyl)-1,3-dihydro-isoindole-2-carbonyl]-phenyl ester.

48. A compound according to paragraph 47 of the formula (1b):

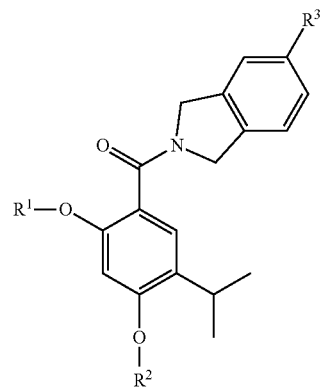

(1b)

or a salt, solvate, N-oxide or tautomer thereof;

wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;

$R^{1a}$ and $R^{2a}$ are the same or different and each is selected from hydrogen, $C_{1-2}$ alkyl, $C_{2-3}$ alkenyl and $C_{2-3}$ alkynyl wherein the $C_{1-2}$ alkyl is optionally substituted by methoxy;

$R^{1b}$ and $R^{2b}$ are the same or different and are selected from hydrogen and $C(O)NR^4R^5$, wherein $R^4$ and $R^5$ are both $C_{1-4}$ alkyl; or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; or $R^{1b}$ and $R^{2b}$ are the same or different and are selected from hydrogen and $C(O)R^{6a}$, wherein $R^{ha}$ is $C_{2-4}$ alkyl; or $R^{1b}$ and $R^{2b}$ are the same or different and are selected from hydrogen and $C(O)R^6$ where $R^6$ is selected from methyl, ethyl, propyl, isopropyl, butyl, 1-methylpropyl, 2-methylpropyl and tert-butyl; or one of $R^{1b}$ and $R^{2b}$ is $C(O)NR^{4a}R^{5a}$ where $R^{4a}$ and $R^{5a}$ are both $C_{1-4}$ alkyl, and the other of $R^{1b}$ and $R^{2b}$ is selected from $C(O)R^6$ and $C(O)OR^6$; and $R^3$ is a group D:

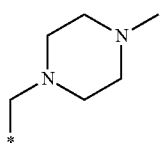

wherein the asterisk denotes the point of attachment to the isoindoline ring.

49. A compound according to paragraph 48 of the formula (1c):

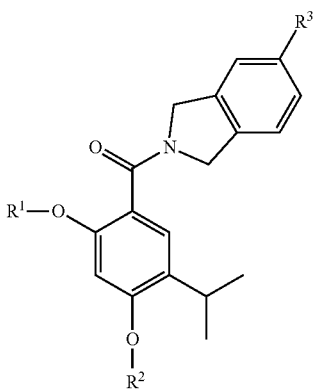

or a salt, solvate, N-oxide or tautomer thereof;

wherein $R^1$ is $R^{1b}$ and $R^2$ is $R^{2b}$; provided that at least one of $R^1$ and $R^2$ is other than hydrogen;

$R^{1b}$ and $R^{2b}$ are the same or different and are selected from hydrogen and $C(O)NR^4R^5$, wherein $R^4$ and $R^5$ are both $C_{1-4}$ alkyl; or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and $R^3$ is a group D:

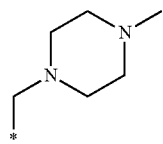

wherein the asterisk denotes the point of attachment to the isoindoline ring.

50. A compound according to paragraph 47 wherein $R^1$ is $R^{1a}$ and $R^2$ is $R^{2a}$ and $R^{1a}$ and $R^{2a}$ are each selected from hydrogen, methyl, methoxymethyl and allyl.

51. A compound according to paragraph 47 or paragraph 48 wherein $R^1$ is $R^{1b}$ and $R^2$ is $R^{2b}$ and $R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl.

52. A compound according to paragraph 47 wherein $R^6$ is selected from methyl, ethyl, propyl, isopropyl, butyl, 1-methylpropyl, 2-methylpropyl and tert-butyl.

53. A compound according to paragraph 52 wherein $R^6$ is $C_{2-4}$ alkyl.

54. A compound according to paragraph 51 wherein:
$R^{1b}$ and $R^{2b}$ are the same or different and are selected from hydrogen and $C(O)OR^6$; and
$R^6$ is tert-butyl or isopropyl.

55. A compound according to paragraph 49 or paragraph 51 wherein $R^{1b}$ and $R^{2b}$ are the same or different and each is hydrogen or a group $C(O)NR^4R^5$, where $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups.

56. A compound according to paragraph 55 wherein the saturated heterocyclic ring is selected from pyrrolidine, piperidine, piperazine, 4-methylpiperazine and morpholine.

57. A compound according to paragraph 47 which is selected from:
(4-hydroxy-5-isopropyl-2-methoxy-phenyl)-[5-(4-methyl-piperazin-1-ylmethyl)-1,3-dihydro-isoindol-2-yl]-methanone;
(2-hydroxy-5-isopropyl-4-methoxy-phenyl)-[5-(4-methyl-piperazin-1-ylmethyl)-1,3-dihydro-isoindol-2-yl]-methanone;
(5-isopropyl-2,4-dimethoxy-phenyl)-[5-(4-methyl-piperazin-1-ylmethyl)-1,3-dihydro-isoindol-2-yl]-methanone;
(2-allyloxy-4-hydroxy-5-isopropyl-phenyl)-[5-(4-methyl-piperazin-1-ylmethyl)-1,3-dihydro-isoindol-2-yl]-methanone;
(4-allyloxy-2-hydroxy-5-isopropyl-phenyl)-[5-(4-methyl-piperazin-1-ylmethyl)-1,3-dihydro-isoindol-2-yl]-methanone;
(2,4-bis-allyloxy-5-isopropyl-phenyl)-[5-(4-methyl-piperazin-1-ylmethyl)-1,3-dihydro-isoindol-2-yl]-methanone;
[4-hydroxy-5-isopropyl-2-(methoxymethyloxy)-phenyl]-[5-(4-methyl-piperazin-1-ylmethyl)-1,3-dihydro-isoindol-2-yl]-methanone;
[2-hydroxy-5-isopropyl-4-(methoxymethyloxy)-phenyl]-[5-(4-methyl-piperazin-1-ylmethyl)-1,3-dihydro-isoindol-2-yl]-methanone;

[5-isopropyl-2,4-bis-(methoxymethyloxy)-phenyl]-[5-(4-methyl-piperazin-1-ylmethyl)-1,3-dihydro-isoindol-2-yl]-methanone;

diethyl-carbamic acid 5-diethylcarbamoyloxy-2-isopropyl-4-[5-(4-methyl-piperazin-1-ylmethyl)-1,3-dihydro-isoindole-2-carbonyl]-phenyl ester;

dimethyl-carbamic acid 5-dimethylcarbamoyloxy-2-isopropyl-4-[5-(4-methyl-piperazin-1-ylmethyl)-1,3-dihydro-isoindole-2-carbonyl]-phenyl ester;

2-[2,4-bis-(pyrrolidin-1-ylcarbonyloxy)-5-isopropyl-benzoyl]-5-(4-methyl-piperazin-1-ylmethyl)-1,3-dihydro-isoindole;

2-[2,4-bis-(morpholin-4-ylcarbonyloxy)-5-isopropyl-benzoyl]-5-(4-methyl-piperazin-1-ylmethyl)-1,3-dihydro-isoindole;

diethyl-carbamic acid 5-hydroxy-4-isopropyl-2-[5-(4-methyl-piperazin-1-ylmethyl)-1,3-dihydro-isoindole-2-carbonyl]-phenyl ester;

diethyl-carbamic acid 5-hydroxy-2-isopropyl-4-[5-(4-methyl-piperazin-1-ylmethyl)-1,3-dihydro-isoindole-2-carbonyl]-phenyl ester;

dimethyl-carbamic acid 5-hydroxy-4-isopropyl-2-[5-(4-methyl-piperazin-1-ylmethyl)-1,3-dihydro-isoindole-2-carbonyl]-phenyl ester;

dimethyl-carbamic acid 5-hydroxy-2-isopropyl-4-[5-(4-methyl-piperazin-1-ylmethyl)-1,3-dihydro-isoindole-2-carbonyl]-phenyl ester;

2-[2-(pyrrolidin-1-ylcarbonyloxy)-4-hydroxy-5-isopropyl-benzoyl]-5-(4-methyl-piperazin-1-ylmethyl)-1,3-dihydro-isoindole;

2-[4-(pyrrolidin-1-ylcarbonyloxy)-2-hydroxy-5-isopropyl-benzoyl]-5-(4-methyl-piperazin-1-ylmethyl)-1,3-dihydro-isoindole;

2-[2-(morpholin-4-ylcarbonyloxy)-4-hydroxy-5-isopropyl-benzoyl]-5-(4-methyl-piperazin-1-ylmethyl)-1,3-dihydro-isoindole;

2-[4-(morpholin-4-ylcarbonyloxy)-2-hydroxy-5-isopropyl-benzoyl]-5-(4-methyl-piperazin-1-ylmethyl)-1,3-dihydro-isoindole;

carbonic acid tert-butyl ester 5-dimethylcarbamoyloxy-4-isopropyl-2-[5-(4-methyl-piperazin-1-ylmethyl)-1,3-dihydro-isoindole-2-carbonyl]-phenyl ester;

carbonic acid 5-tert-butoxycarbonyloxy-4-isopropyl-2-[5-(4-methyl-piperazin-1-ylmethyl)-1,3-dihydro-isoindole-2-carbonyl]-phenyl ester tert-butyl ester;

2,2-dimethyl-propionic acid 5-(2,2-dimethyl-propionyloxy)-2-isopropyl-4-[5-(4-methyl-piperazin-1-ylmethyl)-1,3-dihydro-isoindole-2-carbonyl]-phenyl ester;

isobutyric acid 5-isobutyryloxy-2-isopropyl-4-[5-(4-methyl-piperazin-1-ylmethyl)-1,3-dihydro-isoindole-2-carbonyl]-phenyl ester;

and salts, solvates, tautomers and N-oxides thereof.

58. Dimethyl-carbamic acid 5-hydroxy-2-isopropyl-4-[5-(4-methyl-piperazin-1-ylmethyl)-1,3-dihydro-isoindole-2-carbonyl]-phenyl ester.

59. A pharmaceutical composition comprising a compound according to any one of paragraphs 47 to 58 and a pharmaceutically acceptable carrier.

60. A method for the treatment of a disease state, condition or cancer in a patient in need thereof (e g a mammal such as a human), which method comprises adiminstering to the said patient a therapeutically effective amount of a compound as defined in any one of paragraphs 47 to 58 or a pharmaceutical composition according to paragraph 59, wherein the disease state, condition or cancer is selected from:

(i) a disease state or condition mediated by Hsp90; or (ii) a disease or condition comprising or arising from abnormal cell growth in a mammal; or (iii) cancer; or (iv) a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, neuroblastoma, glioma (a High grade glioma) or schwannoma; melanoma (e.g. malignant or metastatic melanoma); seminoma; teratocarcinoma; osteosarcoma; keratoacanthoma; thyroid follicular cancer; or Kaposi's sarcoma. A further example of a tumour of mesenchymal origin is Ewing's sarcoma; or (v) a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, gall bladder, ovary, pancreas e.g. exocrine pancreatic carcinoma, stomach, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkitt's lymphoma; a hematopoieitic tumour of myeloid lineage, including acute myeloid leukaemia, chronic myeloid leukaemias, myelogenous leukaemias, and Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or rhabdomyosarcoma; a tumour of the central or peripheral nervous system, for example astrocytoma, glioma (a High grade glioma); melanoma (e.g. malignant or metastatic melanoma); osteosarcoma; or thyroid follicular cancer. A further example of a tumour of mesenchymal origin is Ewing's sarcoma; or (vi) a cancer selected from metastatic breast cancer which is HER2 positive; adenocarcinoma of the prostate; metastatic melanoma; non-small cell carcinoma of the lung (NSCLC); small cell carcinoma of the lung (SCLC); high grade gliomas; gastrointestinal stromal tumors (GIST); colorectal cancer; glioblastoma; melanoma; metastatic thyroid cancer; prostate cancer; and rectal cancer; or (vii) a cancer selected from colorectal cancer; glioblastoma; melanoma; metastatic thyroid cancer; prostate cancer; and rectal cancer.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A combination of a compound of the formula (1 a):

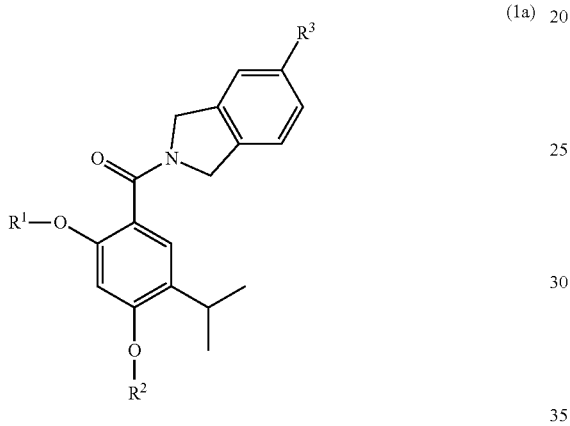

(1a)

or a salt, N-oxide or tautomer thereof;
wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;
$R^{1a}$ and $R^{2a}$ are the same or different and each is selected from hydrogen, $C_{1-4}$ alkyl, $C_{2-4}$ alkenyl and $C_{2-4}$ alkynyl wherein the $C_{1-4}$ alkyl is substituted by $C_{1-2}$ alkoxy;
$R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl, or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and
$R^3$ is a group D:

D wherein the asterisk denotes the point of attachment to the isoindoline ring;
but excluding the compound acetic acid 5-acetoxy-4-isopropyl-2-[5-(4-methyl-piperazin-1-ylmethyl)-1,3-dihydro-isoindole-2-carbonyl]-phenyl ester;

with another therapeutic agent or ancillary agent selected from:
topoisomerase I inhibitors
antimetabolites
tubulin targeting agents
DNA binder and topoisomerase II inhibitors
alkylating Agents
monoclonal Antibodies.
anti-Hormones
signal Transduction Inhibitors
proteasome Inhibitors
cytokines and retinoids
chromatin targeted therapies;
anti-emetic agents and agents that prevent or decrease the duration of chemotherapy-associated neutropenia and prevent complications that arise from reduced levels of red blood cells or white blood cells;
agents that inhibit bone resorption;
agents that suppress inflammatory responses;
agents used to reduce blood levels of growth hormone and IGF-I in acromegaly patients;
agents used as an antidote to drugs that decrease levels of folic acid, or folinic acid itself.

2. The combination according to claim 1, wherein the compound of formula (1a) is represented by formula (1b):

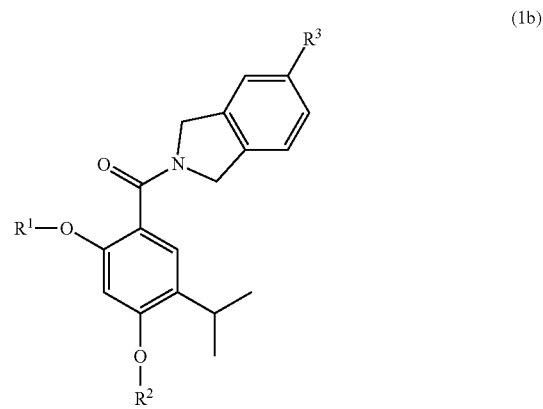

(1b)

or a salt, N-oxide or tautomer thereof;
wherein either $R^1$ is $R^{1a}$ and $R^2$ is $R^{2a}$; or $R^1$ is $R^{1b}$ and $R^2$ is $R^{2b}$; provided that in each case at least one of $R^1$ and $R^2$ is other than hydrogen;
$R^{1a}$ and $R^{2a}$ are the same or different and each is selected from hydrogen, $C_{1-2}$ alkyl, $C_{2-3}$ alkenyl and $C_{2-3}$ alkynyl wherein the $C_{1-2}$ alkyl is substituted by methoxy;
$R^{1b}$ and $R^{2b}$ are the same or different and are selected from hydrogen and $C(O)NR^4R^5$, wherein $R^4$ and $R^5$ are both $C_{1-4}$ alkyl; or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; or
$R^{1b}$ and $R^{2b}$ are the same or different and are selected from hydrogen and $C(O)R^{6a}$, wherein $R^{6a}$ is $C_{2-4}$ alkyl; or
$R^{1b}$ and $R^{2b}$ are the same or different and are selected from hydrogen and $C(O)R^6$ where $R^6$ is selected from methyl, ethyl, propyl, isopropyl, butyl, 1-methylpropyl, 2-methylpropyl and tent-butyl; or
one of $R^{1b}$ and $R^{2b}$ is $C(O)NR^{4a}R^{5a}$ where $R^{4a}$ and $R^{5a}$ are both $C_{1-4}$ alkyl, and the other of $R^{1b}$ and $R^{2b}$ is selected from $C(O)R^6$ and $C(O)OR^6$; and $R^3$ is a group D:

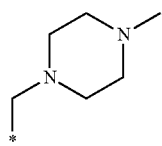

wherein the asterisk denotes the point of attachment to the isoindoline ring.

3. The combination according to claim 1, wherein the compound of formula (1a) is represented by formula (1c):

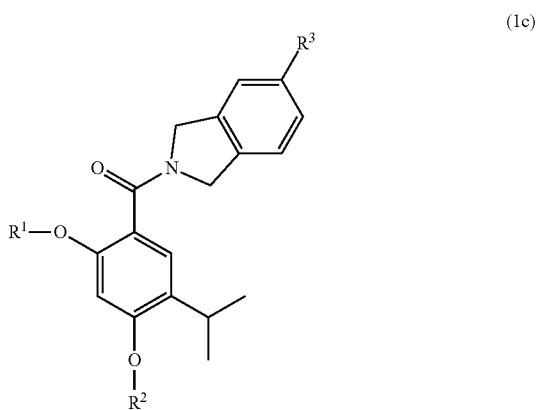

(1c)

or a salt, N-oxide or tautomer thereof;
wherein $R^1$ is $R^{1b}$ and $R^2$ is $R^{2b}$; provided that at least one of $R^1$ and $R^2$ is other than hydrogen;
$R^{1b}$ and $R^{2b}$ are the same or different and are selected from hydrogen and $C(O)NR^4R^5$, wherein $R^4$ and $R^5$ are both $C_{1-4}$ alkyl; or $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups; and
$R^3$ is a group D:

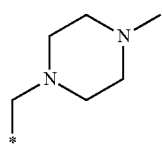

wherein the asterisk denotes the point of attachment to the isoindoline ring.

4. The combination according to claim 1, wherein $R^1$ is $R^{1b}$ and $R^2$ is $R^{2b}$ and $R^{1b}$ and $R^{2b}$ are the same or different and are selected from hydrogen, $C(O)NR^4R^5$, $C(O)R^6$ and $C(O)OR^6$ where $R^6$ is $C_{1-4}$ alkyl, $R^4$ and $R^5$ are both $C_{1-4}$ alkyl 5. The combination according to claim 4, wherein:
$R^{1b}$ and $R^{2b}$ are the same or different and are selected from hydrogen and $C(O)OR^6$; and
$R^6$ is tert-butyl or isopropyl.

6. The combination according to claim 3 or claim 4, wherein $R^{1b}$ and $R^{2b}$ are the same or different and each is hydrogen or a group $C(O)NR^4R^5$ where $NR^4R^5$ forms a 4 to 7 membered saturated heterocyclic ring optionally containing a second heteroatom ring member selected from O, N or S and oxidised forms of N and S, the heterocyclic ring being optionally substituted by one or two $C_{1-4}$ alkyl groups and/or one or two oxo groups.

7. The combination according to claim 6, wherein the saturated heterocyclic ring is selected from pyrrolidine, piperidine, piperazine, 4-methylpiperazine and morpholine.

8. The combination according to claim 1, wherein $R^6$ is selected from methyl, ethyl, propyl, isopropyl, butyl, 1-methylpropyl, 2-methylpropyl and tert-butyl.

9. The combination according to claim 8, wherein $R^6$ is $C_{2-4}$ alkyl.

10. The combination according to claim 1, wherein the compound of formula (1a) is selected from:
(2-allyloxy-4-hydroxy-5-isopropyl-phenyl)-[5-(4-methyl-piperazin-1-ylmethyl)-1,3-dihydro-isoindol-2-yl]-methanone;
(4-allyloxy-2-hydroxy-5-isopropyl-phenyl)-[5-(4-methyl-piperazin-1-ylmethyl)-1,3-dihydro-isoindol-2-yl]-methanone;
(2,4-bis-allyloxy-5-isopropyl-phenyl)-[5-(4-methyl-piperazin-1-ylmethyl)-1,3-dihydro-isoindol-2-yl]-methanone;
[4-hydroxy-5-isopropyl-2-(methoxymethyloxy)-phenyl]-[5-(4-methyl-piperazin-1-ylmethyl)-1,3-dihydro-isoindol-2-yl]-methanone;
[2-hydroxy-5-isopropyl-4-(methoxymethyloxy)-phenyl]-[5-(4-methyl-piperazin-1-ylmethyl)-1,3-dihydro-isoindol-2-yl]-methanone;
[5-isopropyl-2,4-bis-(methoxymethyloxy)-phenyl]-[5-(4-methyl-piperazin-1-ylmethyl)-1,3-dihydro-isoindol-2-yl]-methanone;
diethyl-carbamic acid 5-diethylcarbamoyloxy-2-isopropyl-4-[5-(4-methyl-piperazin-1-ylmethyl)-1,3-dihydro-isoindole-2-carbonyl]-phenyl ester;
dimethyl-carbamic acid 5-dimethylcarbamoyloxy-2-isopropyl-4-[5-(4-methyl-piperazin-1-ylmethyl)-1,3-dihydro-isoindole-2-carbonyl]-phenyl ester;
2-[2,4-bis-(pyrrolidin-1-ylcarbonyloxy)-5-isopropyl-benzoyl]-5-(4-methyl-piperazin-1-ylmethyl)-1,3-dihydro-isoindole;
2-[2,4-bis-(morpholin-4-ylcarbonyloxy)-5-isopropyl-benzoyl]-5-(4-methyl-piperazin-1-ylmethyl)-1,3-dihydro-isoindole;
diethyl-carbamic acid 5-hydroxy-4-isopropyl-2-[5-(4-methyl-piperazin-1-ylmethyl)-1,3-dihydro-isoindole-2-carbonyl]-phenyl ester;
diethyl-carbamic acid 5-hydroxy-2-isopropyl-4-[5-(4-methyl-piperazin-1-ylmethyl)-1,3-dihydro-isoindole-2-carbonyl]phenyl ester;
dimethyl-carbamic acid 5-hydroxy-4-isopropyl-2-[5-(4-methyl-piperazin-1-ylmethyl)-1,3-dihydro-isoindole-2-carbonyl]-phenyl ester;
dimethyl-carbamic acid 5-hydroxy-2-isopropyl-4-[5-(4-methyl-piperazin-1-ylmethyl)-1,3-dihydro-isoindole-2-carbonyl]-phenyl ester;
2-[2-(pyrrolidin-1-ylcarbonyloxy)-4-hydroxy-5-isopropyl-benzoyl]-5-(4-methyl-piperazin-1-ylmethyl)-1,3-dihydro-isoindole;
2-[4-(pyrrolidin-1-ylcarbonyloxy)-2-hydroxy-5-isopropyl-benzoyl]-5-(4-methyl-piperazin-1-ylmethyl)-1,3-dihydro-isoindole;
2-[2-(morpholin-4-ylcarbonyloxy)-4-hydroxy-5-isopropyl-benzoyl]-5-(4-methyl-piperazin-1-ylmethyl)-1,3-dihydro-isoindole;

2-[4-(morpholin-4-ylcarbonyloxy)-2-hydroxy-5-isopropyl-benzoyl]-5-(4-methyl-piperazin-1-ylmethyl)-1,3-dihydro-isoindole;

carbonic acid tert-butyl ester 5-dimethylcarbamoyloxy-4-isopropyl-2-[5-(4-methyl-piperazin-1-ylmethyl)-1,3-dihydro-isoindole-2-carbonyl]-phenyl ester;

carbonic acid 5-tert-butoxycarbonyloxy-4-isopropyl-2-[5-(4-methyl-piperazin-1-ylmethyl)-1,3-dihydro-isoindole-2-carbonyl]-phenyl ester tert-butyl ester;

2,2-dimethyl-propionic acid 5-(2,2-dimethyl-propionyloxy)-2-isopropyl-4-[5-(4-methyl-piperazin-1-ylmethyl)-1,3-dihydro-isoindole-2-carbonyl]-phenyl ester;

isobutyric acid 5-isobutyryloxy-2-isopropyl-4-[5-(4-methyl-piperazin-1-ylmethyl)-1,3-dihydro-isoindole-2-carbonyl]-phenyl ester;

and salts, tautomers and N-oxides thereof.

11. A combination, comprising dimethyl-carbamic acid 5-hydroxy-2-isopropyl-4-[5-(4-methyl-piperazin-1-ylmethyl)-1,3-dihydro-isoindole-2-carbonyl]-phenyl ester; with another therapeutic agent or ancillary agent selected from:

topoisomerase I inhibitors,
antimetabolites,
tubulin targeting agents,
DNA binder and topoisomerase II inhibitors,
alkylating agents,
monoclonal antibodies,
anti-hormones,
signal transduction inhibitors,
proteasome inhibitors,
cytokines and retinoids,
chromatin targeted therapies,
anti-emetic agents and agents that prevent or decrease the duration of chemotherapy associated neutropenia and prevent complications that arise from reduced levels of red blood cells or white blood cells,
agents that inhibit bone resorption,
agents that suppress inflammatory responses,
agents used to reduce blood levels of growth hormone and IGF-I in acromegaly patients, and
agents used as an antidote to drugs that decrease levels of folic acid, or folinic acid itself.

12. A method for the treatment of a disease state, condition or a cancer in a patient in need thereof, which method comprises administering to the said patient a therapeutically effective amount of a combination as defined in claim 1, wherein the disease state, condition or cancer is selected from:

(i) a carcinoma of the bladder, breast, colon, kidney, epidermis, liver, lung, oesophagus, gall bladder, ovary, pancreas e.g. exocrine pancreatic carcinoma, stomach, cervix, thyroid, prostate, gastrointestinal system, or skin; a hematopoieitic tumour of lymphoid lineage; a hematopoieitic tumour of myeloid lineage; thyroid follicular cancer; a tumour of mesenchymal origin; a tumour of the central or peripheral nervous system; melanoma; seminoma; teratocarcinoma; osteosarcoma; keratoacanthoma; thyroid follicular cancer; or Kaposi's sarcoma; or (ii) colon adenocarcinoma; colon adenoma; adenocarcinoma, small cell lung cancer; non-small cell lung carcinomas; exocrine pancreatic carcinoma; gastrointestinal stromal tumours; squamous cell carcinoma; leukaemia; acute lymphocytic leukaemia; chronic lymphocytic leukaemia; B-cell lymphoma; diffuse large B cell lymphoma; T-cell lymphoma; Hodgkin's lymphoma; non-Hodgkin's lymphoma; hairy cell lymphoma; Burkitt's lymphoma acute myeloid leukaemia; chronic myeloid leukaemias; myelogenous leukaemias; Imatinib sensitive and refractory chronic myelogenous leukaemias; myelodysplastic syndrome; Bortezomib sensitive and refractory multiple myeloma; myeloproliferative disease; promyelocytic leukaemia; fibrosarcoma; rhabdomyosarcoma; astrocytoma; glioma; a High grade glioma; malignant or metastatic melanoma; or Ewing's sarcoma; or (iii) a cancer selected from metastatic breast cancer which is HER2 positive; adenocarcinoma of the prostate; metastatic melanoma; non-small cell carcinoma of the lung (NSCLC); small cell carcinoma of the lung (SCLC); high grade gliomas; gastrointestinal stromal tumors (GIST); colorectal cancer; glioblastoma; melanoma; metastatic thyroid cancer; prostate cancer; and rectal cancer; or (iv) a cancer selected from colorectal cancer; glioblastoma; melanoma; metastatic thyroid cancer; prostate cancer; and rectal cancer.

* * * * *